US007704947B2

(12) United States Patent
Currie et al.

(10) Patent No.: US 7,704,947 B2
(45) Date of Patent: *Apr. 27, 2010

(54) METHODS AND COMPOSITIONS FOR THE TREATMENT OF GASTROINTESTINAL DISORDERS

(75) Inventors: Mark G. Currie, Sterling, MA (US); Shalina Mahajan-Miklos, Stanford, CA (US); Thea Norman, San Diego, CA (US); G. Todd Milne, Brookline, MA (US)

(73) Assignee: Ironwood Pharmaceuticals, Inc., Cambridge, MA (US)

( * ) Notice: Subject to any disclaimer, the term of this patent is extended or adjusted under 35 U.S.C. 154(b) by 51 days.

This patent is subject to a terminal disclaimer.

(21) Appl. No.: 11/930,696

(22) Filed: Oct. 31, 2007

(65) Prior Publication Data
US 2009/0005534 A1   Jan. 1, 2009

Related U.S. Application Data

(62) Division of application No. 10/766,735, filed on Jan. 28, 2004, now abandoned.

(60) Provisional application No. 60/443,098, filed on Jan. 28, 2003, provisional application No. 60/471,288, filed on May 15, 2003, provisional application No. 60/519,460, filed on Nov. 12, 2003.

(51) Int. Cl.
    C07K 7/08   (2006.01)
(52) U.S. Cl. .......................................... 514/2; 530/327
(58) Field of Classification Search ........................ None
    See application file for complete search history.

(56) References Cited

U.S. PATENT DOCUMENTS

| | | | |
|---|---|---|---|
| 5,140,102 A | 8/1992 | Currie | 530/326 |
| 5,395,490 A | 3/1995 | Hoff | 204/132 |
| 5,489,670 A | 2/1996 | Currie et al. | 530/326 |
| 5,969,097 A | 10/1999 | Wiegand et al. | 530/326 |
| 6,060,037 A | 5/2000 | Waldman | 424/1.65 |
| 7,304,036 B2 | 12/2007 | Currie et al. | |
| 7,371,727 B2 * | 5/2008 | Currie et al. | 514/14 |
| 2003/0073628 A1 | 4/2003 | Shailubhai et al. | 514/12 |
| 2003/0232013 A1 | 12/2003 | Siechman et al. | 424/1.69 |
| 2004/0121961 A1 | 6/2004 | Masferrer | 514/15 |
| 2004/0152868 A1 | 8/2004 | Larsen et al. | 530/317 |
| 2004/0258687 A1 | 12/2004 | Waldman et al. | 424/143.1 |
| 2004/0266989 A1 | 12/2004 | Currie et al. | 530/326 |
| 2005/0032684 A1 | 2/2005 | Cetin et al. | 514/12 |
| 2006/0281682 A1 | 12/2006 | Currie et al. | |
| 2008/0227685 A1 | 9/2008 | Currie et al. | |
| 2009/0062207 A1 | 3/2009 | Currie et al. | |
| 2009/0191611 A1 | 7/2009 | Currie et al. | |

FOREIGN PATENT DOCUMENTS

| | | |
|---|---|---|
| EP | 1012188 | 6/2000 |
| WO | WO 99/14239 | 3/1999 |
| WO | WO 01/25266 | 4/2001 |
| WO | WO 02/062369 | 8/2002 |
| WO | WO 02/078683 | 10/2002 |
| WO | WO 02/079235 | 10/2002 |
| WO | WO 02/098912 | 12/2002 |
| WO | WO 03/072125 | 9/2003 |
| WO | WO03/072754 | 9/2003 |
| WO | WO2004/069165 | 8/2004 |
| WO | WO 2004/071436 | 8/2004 |
| WO | WO2005/087797 | 9/2005 |

OTHER PUBLICATIONS

Amarante et al., "The κ-opioid agonist (±)-bremazocine elicits peripheral antinociception by activation of the L-arginine/nitric oxide/cyclic GMP pathway" *European Journal of Pharmacology*, vol. 454: pp. 19-23 (2002).
Arita et al., "Purification and characterization of a heat-stable enterotoxin of Vibrio mimicus" *FEMS Microbiology Letters*, vol. 79/1: pp. 105-110 (1991).
Chan et al., "Amino Acid Sequence of Heat-stable Enterotoxin Produced by *Escherichia coli* Pathogenic for Man" *The Journal of Biological Chemistry*, vol. 256, No. 15: pp. 7744-7746 (1981).
Forte et al., "Lymphoguanylin: Cloning and Characterization of a Unique Member of the Guanylin Peptide Family" *Endocrinology*, vol. 140, No. 4: pp. 1800-1806 (1999).
Giannela, "*Escherichia coli* heat-stable enterotoxins, guanylins, and their receptors: What are they and what do they do?" *The Journal of Laboratory and Clinical Medicine*, vol. 125, No. 2: pp. 173-181 (1995).
Gualillo et al., "Ghrelin, a widespread hormone: insights into molecular and cellular regulation of its expression and mechanism of action" *FEBS Letters*, vol. 552: pp. 105-109 (2003).
Guarino et al., "Citrobacter freundii Produces an 18-Amino-Acid Heat-Stable Enterotoxin Identical to the 18-Amino-Acid *Escherichia coli* Heat-Stable Enterotoxin (ST la)" *Infection and Immunity*, vol. 57, No. 2: pp. 649-652 (1989).
Huang et al., "Nucleotide sequence of a gene encoding the novel Yersinia enterocolitica heat-stable enterotoxin that includes a pro-region-like sequence in its mature toxin molecule" *Microbial Pathogenesis*, vol. 22: pp. 89-97 (1997).

(Continued)

*Primary Examiner*—Christopher R. Tate
*Assistant Examiner*—Roy Teller
(74) *Attorney, Agent, or Firm*—Honigman Miller Schwartz and Cohn LLP; Kelly T. Murphy; Johnathan P. O'Brien

(57) ABSTRACT

The present invention features compositions and related methods for treating IBS and other gastrointestinal disorders and conditions (e.g., gastrointestinal motility disorders, functional gastrointestinal disorders, gastroesophageal reflux disease (GERD), Crohn's disease, ulcerative colitis, Inflammatory bowel disease, functional heartburn, dyspepsia (including functional dyspepsia or nonulcer dyspepsia), gastroparesis, chronic intestinal pseudo-obstruction (or colonic pseudo-obstruction), and disorders and conditions associated with constipation, e.g., constipation associated with use of opiate pain killers, post-surgical constipation, and constipation associated with neuropathic disorders as well as other conditions and disorders using peptides and other agents that activate the guanylate cyclase C (GC-C) receptor.

16 Claims, 19 Drawing Sheets

OTHER PUBLICATIONS

Figure 1A:
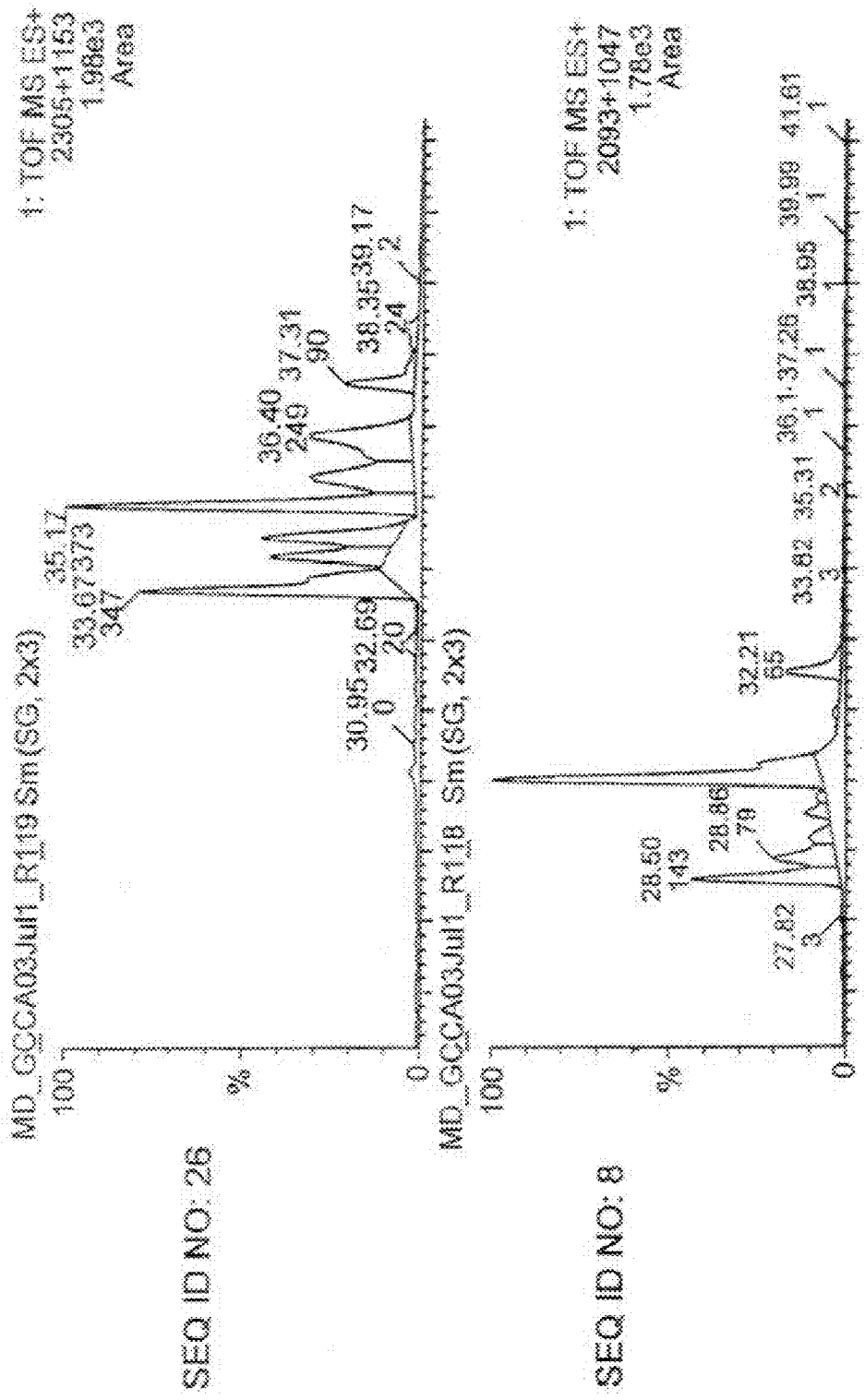

Jain et al., "Sildenafil-induced peripheral analgesia and activation of the nitric oxide-cyclic GMP pathway" *Brain Research*, vol. 909: pp. 170-178 (2001).

Kim et al., "Changes in ghrelin and ghrelin receptor expression according to feeding status" *NeuroReport*, vol. 14, No. 10: pp. 1317-1320 (2003).

Lazaro-lbanez et al., "Participation of the nitric oxide-cyclic GMP-ATP-sensitive K+ channel pathway in the antinociceptive action of ketorolac" *European Journal of Pharmacology*, vol. 426: pp. 39-44 (2001).

Moseley et al., "Isolation and Nucleotide Sequence Determination of a Gene Encoding a Heat-Stable Enterotoxin of *Escherichia coil*" *Infection and Immunity*, vol. 39, No. 3: pp. 1167-1174 (1983).

Nzegwu et al., "Luminal capsaicin inhibits fluid secretion induced by exterotoxin *E. coli* STa, but not by carbachol, in vivo in rat small and large intestines" *Experimental Physiology*, vol. 81, No. 2: pp. 313-315 (1996).

Rolfe et al., "Enterotoxin *Escherichia coli* STa activates a nitric oxide-dependent myenteric plexus secretory reflex in the rat ileum" *The Journal of Physiology*, vol. 475, No. 3: pp. 531-537 (1994).

Rolfe et al., "Vagotomy inhibits the jejunal fluid secretion activated by luminal ileal *Escherichia coli* STa in the rat in vivo" *GUT*, vol. 44: pp. 615-619 (1999).

Shailubhai, "Therapeutic applications of guanylate cyclase-C receptor agonists" *Drug Discovery & Development*, vol. 5, No. 2: pp. 261-268 (2002).

So et al., "Nucleotide Sequence of the Bacterial Transposon Tn1681 Encoding a Heat-Stable (ST) Toxin and Its Identification in Enterotoxigenic *Escherichia coli* Strains" *Proceedings of the National Academy of Science of the U.S.A.*, vol. 77, No. 7 [Part 2: Biological Sciences]: pp. 4011-4015 (1980).

Soares, et al., "Dibutyryl-cyclic GMP induces peripheral antinociception *via* activation of ATP-sensitive K+ channels in the Rat $PGE_2$-induced hyperalgesic paw" *British Journal of Pharmacology*, vol. 134: pp. 127-131 (2001).

Takao et al., "Amino acid sequence of heat-stable enterotoxin produced by *Vibrio cholerae* non-01" *FEBS*), vol. 193, No. 2: pp. 250-254 (1985).

Takao et al., "Isolation, primary structure and synthesis of heat-stable enterotoxin produced by *Yersinia enterocolitica*" *European Journal of Biochemistry*, vol. 152, No. 1: pp. 199-206 (1985).

Vaandrager et al., "Structure and function of the heat-stable enterotoxin receptor/guanylyl cyclase C" *Molecular and Cellular Biochemistry*, vol. 230, Nos. 1&2: pp. 73-83 (2002).

GenBank Accession No. QHECIB; GI:69638; Aimoto et al., Jun. 18, 1999.

GenBank Accession No. P01559; GI:123711; So et al., Oct. 25, 2004.

GenBank Accession No. AAA24653; GI:147878; Sekizaki et al., Apr. 26, 1993.

GenBank Accession No. P01560; GI:123707; Chan et al., Jun. 15, 2004.

GenBank Accession No. AAA27561; GI:295439; Ogawa et al., Jun. 12, 1993.

GenBank Accession No. P04429; GI:123712; Ogawa et al., Jun. 15, 2004.

GenBank Accession No. S34671; GI:421286; Rossolini et al., Apr. 12, 1995.

GenBank Accession No. CAA52209; GI:395161; Guglielmetti et al., Jul. 27, 2995.

GenBank Accession No. A54534; GI:628844; Arita et al., May 3, 1996.

GenBank Accession No. AAL02159; GI:15592919; Teixeira et al., Sep. 13, 2001.

GenBank Accession No. AAA18472; GI:487395; Mikulskis et al., May 26, 1994.

GenBank Accession No. S25659; GI:282047; Takao et al., Oct. 15, 1999.

GenBank Accession No. P74977; GI:3913874; Ramamurthy et al., Jun. 15, 2004.

GenBank Accession No. BAA23656; GI:2662339; Huang et al., Feb. 13, 1999.

GenBank Accession No. P31518; GI:399947; Ibrahim et al., Mar. 15, 2004.

GenBank Accession No. P07965; GI:3915589; Stieglitz et al., Jun. 15, 2004.

Camilleri, "Management of the Irritable Bowel Syndrome" Gastroenterology 120:652-668, 2001.

Drossman, D.A., "The functional gastrointestinal disorders and the Rome II process" Gut 45:Supp. 11:111-113, 1999.

Drossman, D.A., "Psychosocial aspects of the functional gastrointestinal disorders" Gut 45:Supp. 11:1125-1130, 1999.

Drossman et al., "U.S. Householder Survey of Functional Gastrointestinal Disorders" Digestive Diseases and Sciences 38(9):1569-1580, 1993.

Ringel, et al., "Irritable Bowel Syndrome" Annu. Rev. Med. 52:319-38, 2001.

Santos-Neto, et al., "Guanylin and its Lysine-Containing Analogue in the Isolated Perfused Rat Kideny" Pharmacol. & Toxicol. 92:114-120, 2003.

Talley, et al., "Irritable Bowel Syndrome.In a Community: Symptom Subgroups, Risk.." Am. J. of Epidemiology 142(1):76-83, 1995.

Talley, et al., "Medical Costs in Community Subjects with Irritable Bowel Syndrome" Gastroenterology 109(6):1736-1741, 1995.

Abandonment for U.S. Appl. No. 10/766,735 dated Nov. 28, 2007.

Abandonment for U.S. Appl. No. 10/845,895 dated Mar. 09, 2009.

Office Action for U.S. Appl. No. 11/054,071 dated Jul. 6, 2009.

Notice of Allowance for U.S. Appl. No. 11/949,340 dated Sep. 3, 2009.

Forte, L., "Uroguanylin and guanylin peptides; pharmacology and experimental therapeutics", Pharmacology & Therapeutics, vol. 104, (2004), pp. 137-162.

\* cited by examiner

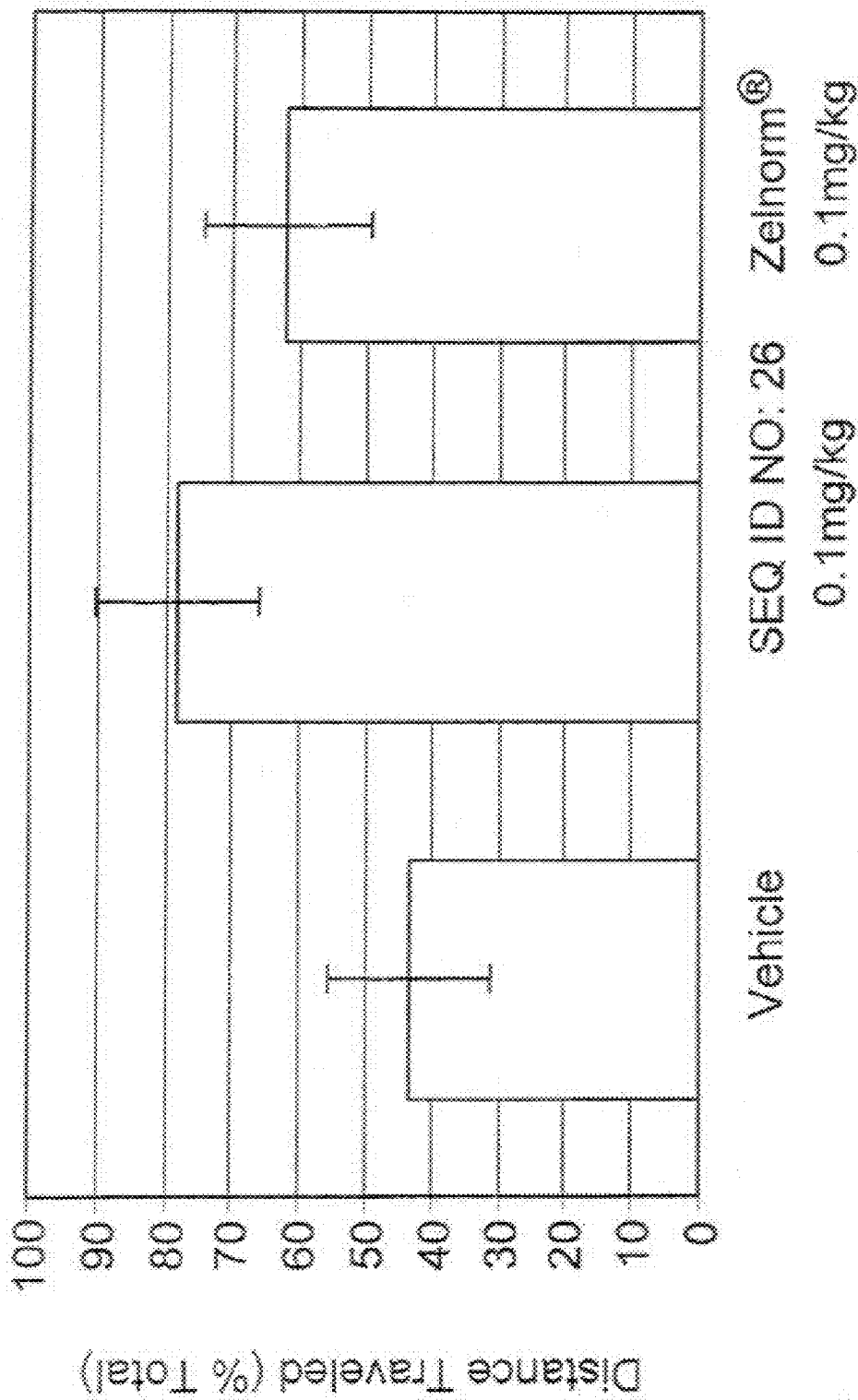

```
SEQUENCE LISTING

<160> NUMBER OF SEQ ID NOS: 125

<210> SEQ ID NO 1
<211> LENGTH: 19
<212> TYPE: PRT
<213> ORGANISM: Escherichia coli

<400> SEQUENCE: 1

Asn Ser Ser Asn Tyr Cys Cys Glu Leu Cys Cys Asn Pro Ala Cys Thr
1               5                   10                  15

Gly Cys Tyr

<210> SEQ ID NO 2
<211> LENGTH: 18
<212> TYPE: PRT
<213> ORGANISM: Escherichia coli

<400> SEQUENCE: 2

Asn Thr Phe Tyr Cys Cys Glu Leu Cys Cys Asn Pro Ala Cys Ala Gly
1               5                   10                  15

Cys Tyr

<210> SEQ ID NO 3
<211> LENGTH: 18
<212> TYPE: PRT
<213> ORGANISM: Escherichia coli

<400> SEQUENCE: 3

Asn Thr Phe Tyr Cys Cys Glu Leu Cys Cys Tyr Pro Ala Cys Ala Gly
1               5                   10                  15

Cys Asn

<210> SEQ ID NO 4
<211> LENGTH: 18
<212> TYPE: PRT
<213> ORGANISM: Citrobacter freundii

<400> SEQUENCE: 4

Asn Thr Phe Tyr Cys Cys Glu Leu Cys Cys Asn Pro Ala Cys Ala Gly
1               5                   10                  15

Cys Tyr

<210> SEQ ID NO 5
<211> LENGTH: 30
<212> TYPE: PRT
<213> ORGANISM: Yersinia enterocolitica

<400> SEQUENCE: 5

Gln Ala Cys Asp Pro Pro Ser Pro Pro Ala Glu Val Ser Ser Asp Trp
1               5                   10                  15

Asp Cys Cys Asp Val Cys Cys Asn Pro Ala Cys Ala Gly Cys
                20                  25                  30
```

<210> SEQ ID NO 6
<211> LENGTH: 30
<212> TYPE: PRT
<213> ORGANISM: Yersinia enterocolitica

<400> SEQUENCE: 6

```
Asn Thr Phe Tyr Cys Cys Glu Leu Cys Cys Asn Pro Ala Cys Ala Pro
1               5                   10                  15

Cys Tyr

<210> SEQ ID NO 12
<211> LENGTH: 13
<212> TYPE: PRT
<213> ORGANISM: Vibrio cholerae

<400> SEQUENCE: 12

Ile Asp Cys Cys Glu Ile Cys Cys Asn Pro Ala Cys Phe
1               5                   10

<210> SEQ ID NO 13
<211> LENGTH: 14
<212> TYPE: PRT
<213> ORGANISM: Vibrio cholerae

<400> SEQUENCE: 13

Ile Asp Cys Cys Glu Ile Cys Cys Asn Pro Ala Cys Phe Gly
1               5                   10

<210> SEQ ID NO 14
<211> LENGTH: 17
<212> TYPE: PRT
<213> ORGANISM: Vibrio mimicus

<400> SEQUENCE: 14

Ile Asp Cys Cys Glu Ile Cys Cys Asn Pro Ala Cys Phe Gly Cys Leu
1               5                   10                  15

Asn

<210> SEQ ID NO 15
<211> LENGTH: 17
<212> TYPE: PRT
<213> ORGANISM: Vibrio mimicus

<400> SEQUENCE: 15

Ile Asp Arg Cys Glu Ile Cys Cys Asn Pro Ala Cys Phe Gly Cys Leu
1               5                   10                  15

Asn

<210> SEQ ID NO 16
<211> LENGTH: 16
<212> TYPE: PRT
<213> ORGANISM: Yersinia enterocolitica

<400> SEQUENCE: 16

Asp Trp Asp Cys Cys Asp Val Cys Cys Asn Pro Ala Cys Ala Gly Cys
1               5                   10                  15

<210> SEQ ID NO 17
<211> LENGTH: 16
<212> TYPE: PRT
<213> ORGANISM: Yersinia enterocolitica

<400> SEQUENCE: 17

Asp Trp Asp Cys Cys Asp Val Cys Cys Asn Pro Ala Cys Ala Gly Cys
1               5                   10                  15

<210> SEQ ID NO 18
<211> LENGTH: 17
```

```
<212> TYPE: PRT
<213> ORGANISM: Yersinia enterocolitica

<400> SEQUENCE: 18

Asn Asp Asp Trp Cys Cys Glu Val Cys Asn Pro Ala Cys Ala Gly
1               5                   10                  15

Cys

<210> SEQ ID NO 19
<211> LENGTH: 16
<212> TYPE: PRT
<213> ORGANISM: Yersinia enterocolitica

<400> SEQUENCE: 19

Trp Asp Trp Cys Cys Glu Leu Cys Cys Asn Pro Ala Cys Phe Gly Cys
1               5                   10                  15

<210> SEQ ID NO 20
<211> LENGTH: 72
<212> TYPE: PRT
<213> ORGANISM: Escherichia coli

<400> SEQUENCE: 20

Met Lys Lys Leu Met Leu Ala Ile Phe Ile Ser Val Leu Ser Phe Pro
1               5                   10                  15

Ser Phe Ser Gln Ser Thr Glu Ser Leu Asp Ser Ser Lys Glu Lys Ile
            20                  25                  30

Thr Leu Glu Thr Lys Lys Cys Asp Val Val Lys Asn Asn Ser Glu Lys
        35                  40                  45

Lys Ser Glu Asn Met Asn Asn Thr Phe Tyr Cys Cys Glu Leu Cys Cys
    50                  55                  60

Asn Pro Ala Cys Ala Gly Cys Tyr
65                  70

<210> SEQ ID NO 21
<211> LENGTH: 72
<212> TYPE: PRT
<213> ORGANISM: Escherichia coli

<400> SEQUENCE: 21

Met Lys Lys Ser Ile Leu Phe Ile Phe Leu Ser Val Leu Ser Phe Ser
1               5                   10                  15

Pro Phe Ala Gln Asp Ala Lys Pro Val Glu Ser Ser Lys Glu Lys Ile
            20                  25                  30

Thr Leu Glu Ser Lys Lys Cys Asn Ile Ala Lys Lys Ser Asn Lys Ser
        35                  40                  45

Gly Pro Glu Ser Met Asn Ser Ser Asn Tyr Cys Cys Glu Leu Cys Cys
    50                  55                  60

Asn Pro Ala Cys Thr Gly Cys Tyr
65                  70

<210> SEQ ID NO 22
<211> LENGTH: 71
<212> TYPE: PRT
<213> ORGANISM: Yersinia enterocolitica

<400> SEQUENCE: 22

Met Lys Lys Ile Val Phe Val Leu Val Leu Met Leu Ser Ser Phe Gly
1               5                   10                  15

Ala Phe Gly Gln Glu Thr Val Ser Gly Gln Phe Ser Asp Ala Leu Ser
```

-continued

```
                 20                  25                  30

Thr Pro Ile Thr Ala Glu Val Tyr Lys Gln Ala Cys Asp Pro Leu
        35                  40                  45

Pro Pro Ala Glu Val Ser Ser Asp Trp Asp Cys Cys Asp Val Cys Cys
    50                  55                  60

Asn Pro Ala Cys Ala Gly Cys
65                  70
```

<210> SEQ ID NO 23
<211> LENGTH: 54
<212> TYPE: PRT
<213> ORGANISM: Artificial Sequence
<220> FEATURE:
<223> OTHER INFORMATION: Synthetically generated amino terminal leader
      sequence

<400> SEQUENCE: 23

```
Met Lys Lys Ser Ile Leu Phe Ile Phe Leu Ser Val Leu Ser Phe Ser
1               5                   10                  15

Pro Phe Ala Gln Asp Ala Lys Pro Val Glu Ser Ser Lys Glu Lys Ile
            20                  25                  30

Thr Leu Glu Ser Lys Lys Cys Asn Ile Ala Lys Lys Ser Asn Lys Ser
        35                  40                  45

Gly Pro Glu Ser Met Asn
    50
```

<210> SEQ ID NO 24
<211> LENGTH: 53
<212> TYPE: PRT
<213> ORGANISM: Artificial Sequence
<220> FEATURE:
<223> OTHER INFORMATION: Synthetically generated peptide

<400> SEQUENCE: 24

```
Met Lys Lys Ser Ile Leu Phe Ile Phe Leu Ser Val Leu Ser Phe Ser
1               5                   10                  15

Pro Phe Ala Gln Asp Ala Lys Pro Ala Gly Ser Ser Lys Glu Lys Ile
            20                  25                  30

Thr Leu Glu Ser Lys Lys Cys Asn Ile Val Lys Lys Ser Asn Lys Ser
        35                  40                  45

Gly Pro Glu Ser Met
    50
```

<210> SEQ ID NO 25
<211> LENGTH: 53
<212> TYPE: PRT
<213> ORGANISM: Escherichia coli

<400> SEQUENCE: 25

```
Met Lys Lys Ser Ile Leu Phe Ile Phe Leu Ser Val Leu Ser Phe Ser
1               5                   10                  15

Pro Phe Ala Gln Asp Ala Lys Pro Ala Gly Ser Ser Lys Glu Lys Ile
            20                  25                  30

Thr Leu Glu Ser Lys Lys Cys Asn Ile Val Lys Lys Asn Asn Glu Ser
        35                  40                  45

Ser Pro Glu Ser Met
    50
```

<210> SEQ ID NO 26
<211> LENGTH: 19

```
<212> TYPE: PRT
<213> ORGANISM: Artificial Sequence
<220> FEATURE:
<223> OTHER INFORMATION: Syntheticaly generated peptide

<400> SEQUENCE: 26

Asn Ser Ser Asn Tyr Cys Cys Glu Leu Cys Cys Asn Pro Ala Cys Thr
1               5                   10                  15

Gly Cys Tyr

<210> SEQ ID NO 27
<211> LENGTH: 19
<212> TYPE: PRT
<213> ORGANISM: Artificial Sequence
<220> FEATURE:
<223> OTHER INFORMATION: Syntheticaly generated peptide

<400> SEQUENCE: 27

Asn Ser Ser Asn Tyr Cys Cys Glu Leu Cys Cys Asn Pro Ala Cys Trp
1               5                   10                  15

Gly Cys Tyr

<210> SEQ ID NO 28
<211> LENGTH: 19
<212> TYPE: PRT
<213> ORGANISM: Artificial Sequence
<220> FEATURE:
<223> OTHER INFORMATION: Syntheticaly generated peptide

<400> SEQUENCE: 28

Asn Ser Ser Asn Tyr Cys Cys Glu Tyr Cys Cys Asn Pro Ala Cys Thr
1               5                   10                  15

Gly Cys Tyr

<210> SEQ ID NO 29
<211> LENGTH: 14
<212> TYPE: PRT
<213> ORGANISM: Artificial Sequence
<220> FEATURE:
<223> OTHER INFORMATION: Syntheticaly generated peptide

<400> SEQUENCE: 29

Cys Cys Glu Leu Cys Cys Asn Pro Ala Cys Thr Gly Cys Tyr
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Syntheticaly generated peptide

<400> SEQUENCE: 30

Cys Cys Glu Leu Cys Cys Asn Pro Ala Cys Trp Gly Cys Tyr
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Syntheticaly generated peptide

<400> SEQUENCE: 31

Cys Cys Glu Tyr Cys Cys Asn Pro Ala Cys Thr Gly Cys Tyr
```

```
<210> SEQ ID NO 32
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 32

Asn Cys Cys Glu Leu Cys Cys Asn Pro Ala Cys Thr Gly Cys Tyr
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 33

Asn Cys Cys Glu Leu Cys Cys Asn Pro Ala Cys Trp Gly Cys Tyr
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 34

Asn Cys Cys Glu Phe Cys Cys Asn Pro Ala Cys Thr Gly Cys Tyr
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 35

Asn Cys Cys Glu Tyr Cys Cys Asn Pro Ala Cys Thr Gly Cys Tyr
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 36

Asn Cys Cys Glu Trp Cys Cys Asn Pro Ala Cys Thr Gly Cys Tyr
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 37

Asn Cys Cys Glu Arg Cys Cys Asn Pro Ala Cys Thr Gly Cys Tyr
1               5                   10                  15
```

<210> SEQ ID NO 38
<211> LENGTH: 15
<212> TYPE: PRT
<213> ORGANISM: Artificial Sequence
<220> FEATURE:
<223> OTHER INFORMATION: Syntheticaly generated peptide

<400> SEQUENCE: 38

Asn Cys Cys Glu Lys Cys Cys Asn Pro Ala Cys Thr Gly Cys Tyr
1               5                   10                  15

<210> SEQ ID NO 39
<211> LENGTH: 21
<212> TYPE: PRT
<213> ORGANISM: Artificial Sequence
<220> FEATURE:
<223> OTHER INFORMATION: Syntheticaly generated peptide

<400> SEQUENCE: 39

Asn Ser Ser Asn Tyr Cys Cys Glu Leu Cys Cys Asn Pro Ala Cys Thr
1               5                   10                  15

Gly Cys Tyr Asp Phe
            20

<210> SEQ ID NO 40
<211> LENGTH: 21
<212> TYPE: PRT
<213> ORGANISM: Artificial Sequence
<220> FEATURE:
<223> OTHER INFORMATION: Syntheticaly generated peptide

<400> SEQUENCE: 40

Asn Ser Ser Asn Tyr Cys Cys Glu Leu Cys Cys Asn Pro Ala Cys Trp
1               5                   10                  15

Gly Cys Tyr Asp Phe
            20

<210> SEQ ID NO 41
<211> LENGTH: 21
<212> TYPE: PRT
<213> ORGANISM: Artificial Sequence
<220> FEATURE:
<223> OTHER INFORMATION: Syntheticaly generated peptide

<400> SEQUENCE: 41

Asn Ser Ser Asn Tyr Cys Cys Glu Phe Cys Cys Asn Pro Ala Cys Thr
1               5                   10                  15

Gly Cys Tyr Asp Phe
            20

<210> SEQ ID NO 42
<211> LENGTH: 21
<212> TYPE: PRT
<213> ORGANISM: Artificial Sequence
<220> FEATURE:
<223> OTHER INFORMATION: Syntheticaly generated peptide

<400> SEQUENCE: 42

Asn Ser Ser Asn Tyr Cys Cys Glu Tyr Cys Cys Asn Pro Ala Cys Thr
1               5                   10                  15

Gly Cys Tyr Asp Phe
            20

-continued

<210> SEQ ID NO 43
<211> LENGTH: 21
<212> TYPE: PRT
<213> ORGANISM: Artificial Sequence
<220> FEATURE:
<223> OTHER INFORMATION: Syntheticaly generated peptide

<400> SEQUENCE: 43

Asn Ser Ser Asn Tyr Cys Cys Glu Trp Cys Cys Asn Pro Ala Cys Thr
1               5                   10                  15

Gly Cys Tyr Asp Phe
            20

<210> SEQ ID NO 44
<211> LENGTH: 21
<212> TYPE: PRT
<213> ORGANISM: Artificial Sequence
<220> FEATURE:
<223> OTHER INFORMATION: Syntheticaly generated peptide

<400> SEQUENCE: 44

Asn Ser Ser Asn Tyr Cys Cys Glu Arg Cys Cys Asn Pro Ala Cys Thr
1               5                   10                  15

Gly Cys Tyr Asp Phe
            20

<210> SEQ ID NO 45
<211> LENGTH: 21
<212> TYPE: PRT
<213> ORGANISM: Artificial Sequence
<220> FEATURE:
<223> OTHER INFORMATION: Syntheticaly generated peptide

<400> SEQUENCE: 45

Asn Ser Ser Asn Tyr Cys Cys Glu Lys Cys Cys Asn Pro Ala Cys Thr
1               5                   10                  15

Gly Cys Tyr Asp Phe
            20

<210> SEQ ID NO 46
<211> LENGTH: 16
<212> TYPE: PRT
<213> ORGANISM: Artificial Sequence
<220> FEATURE:
<223> OTHER INFORMATION: Syntheticaly generated peptide

<400> SEQUENCE: 46

Cys Cys Glu Leu Cys Cys Asn Pro Ala Cys Thr Gly Cys Tyr Asp Phe
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Syntheticaly generated peptide

<400> SEQUENCE: 47

Cys Cys Glu Leu Cys Cys Asn Pro Ala Cys Trp Gly Cys Tyr Asp Phe
1               5                   10                  15

<210> SEQ ID NO 48
<211> LENGTH: 16
<212> TYPE: PRT
<213> ORGANISM: Artificial Sequence
<220> FEATURE:

<223> OTHER INFORMATION: Syntheticaly generated peptide

<400> SEQUENCE: 48

Cys Cys Glu Phe Cys Cys Asn Pro Ala Cys Thr Gly Cys Tyr Asp Phe
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Syntheticaly generated peptide

<400> SEQUENCE: 49

Cys Cys Glu Tyr Cys Cys Asn Pro Ala Cys Thr Gly Cys Tyr Asp Phe
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Syntheticaly generated peptide

<400> SEQUENCE: 50

Cys Cys Glu Trp Cys Cys Asn Pro Ala Cys Thr Gly Cys Tyr Asp Phe
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Syntheticaly generated peptide

<400> SEQUENCE: 51

Cys Cys Glu Arg Cys Cys Asn Pro Ala Cys Thr Gly Cys Tyr Asp Phe
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Syntheticaly generated peptide

<400> SEQUENCE: 52

Cys Cys Glu Lys Cys Cys Asn Pro Ala Cys Thr Gly Cys Tyr Asp Phe
1               5                   10                  15

<210> SEQ ID NO 53
<211> LENGTH: 17
<212> TYPE: PRT
<213> ORGANISM: Artificial Sequence
<220> FEATURE:
<223> OTHER INFORMATION: Syntheticaly generated peptide

<400> SEQUENCE: 53

Asn Cys Cys Glu Leu Cys Cys Asn Pro Ala Cys Thr Gly Cys Tyr Asp
1               5                   10                  15

Phe

<210> SEQ ID NO 54
<211> LENGTH: 17
<212> TYPE: PRT
<213> ORGANISM: Artificial Sequence
<220> FEATURE:
<223> OTHER INFORMATION: Syntheticaly generated peptide

<400> SEQUENCE: 54

Asn Cys Cys Glu Leu Cys Cys Asn Pro Ala Cys Trp Gly Cys Tyr Asp
1               5                   10                  15

Phe

<210> SEQ ID NO 55
<211> LENGTH: 17
<212> TYPE: PRT
<213> ORGANISM: Artificial Sequence
<220> FEATURE:
<223> OTHER INFORMATION: Syntheticaly generated peptide

<400> SEQUENCE: 55

Asn Cys Cys Glu Phe Cys Cys Asn Pro Ala Cys Thr Gly Cys Tyr Asp
1               5                   10                  15

Phe

<210> SEQ ID NO 56
<211> LENGTH: 17
<212> TYPE: PRT
<213> ORGANISM: Artificial Sequence
<220> FEATURE:
<223> OTHER INFORMATION: Syntheticaly generated peptide

<400> SEQUENCE: 56

Asn Cys Cys Glu Tyr Cys Cys Asn Pro Ala Cys Thr Gly Cys Tyr Asp
1               5                   10                  15

Phe

<210> SEQ ID NO 57
<211> LENGTH: 17
<212> TYPE: PRT
<213> ORGANISM: Artificial Sequence
<220> FEATURE:
<223> OTHER INFORMATION: Syntheticaly generated peptide

<400> SEQUENCE: 57

Asn Cys Cys Glu Trp Cys Cys Asn Pro Ala Cys Thr Gly Cys Tyr Asp
1               5                   10                  15

Phe

<210> SEQ ID NO 58
<211> LENGTH: 17
<212> TYPE: PRT
<213> ORGANISM: Artificial Sequence
<220> FEATURE:
<223> OTHER INFORMATION: Syntheticaly generated peptide

<400> SEQUENCE: 58

Asn Cys Cys Glu Arg Cys Cys Asn Pro Ala Cys Thr Gly Cys Tyr Asp
1               5                   10                  15

Phe

<210> SEQ ID NO 59
<211> LENGTH: 17
<212> TYPE: PRT
<213> ORGANISM: Artificial Sequence
<220> FEATURE:
<223> OTHER INFORMATION: Syntheticaly generated peptide

<400> SEQUENCE: 59

```
Asn Cys Cys Glu Lys Cys Cys Asn Pro Ala Cys Thr Gly Cys Tyr Asp
1               5                   10                  15
Phe
```

<210> SEQ ID NO 60
<211> LENGTH: 42
<212> TYPE: DNA
<213> ORGANISM: Artificial Sequence
<220> FEATURE:
<223> OTHER INFORMATION: Synthetically generated oligonucleotide

<400> SEQUENCE: 60
cacaccatat gaagaaatca atattattta tttttctttc tg            42

<210> SEQ ID NO 61
<211> LENGTH: 46
<212> TYPE: DNA
<213> ORGANISM: Artificial Sequence
<220> FEATURE:
<223> OTHER INFORMATION: Synthetically generated oligonucleotide

<400> SEQUENCE: 61
cacacctcga gttaggtctc catgctttca ggaccacttt tattac        46

<210> SEQ ID NO 62
<211> LENGTH: 69
<212> TYPE: DNA
<213> ORGANISM: Artificial Sequence
<220> FEATURE:
<223> OTHER INFORMATION: Synthetically generated oligonucleotide

<400> SEQUENCE: 62
gcatgaatag tagcaattac tgctgtgaat tgtgttgtaa tcctgcttgt accgggtgct    60
attaataac                                                            69

<210> SEQ ID NO 63
<211> LENGTH: 69
<212> TYPE: DNA
<213> ORGANISM: Artificial Sequence
<220> FEATURE:
<223> OTHER INFORMATION: Synthetically generated oligonucleotide

<400> SEQUENCE: 63
tcgagttatt aatagcaccc ggtacaagca ggattacaac acaattcaca gcagtaattg    60
ctactattc                                                            69

<210> SEQ ID NO 64
<211> LENGTH: 69
<212> TYPE: DNA
<213> ORGANISM: Artificial Sequence
<220> FEATURE:
<223> OTHER INFORMATION: Synthetically generated oligonucleotide

<400> SEQUENCE: 64
gcatgaatag tagcaattac tgctgtgaat attgttgtaa tcctgcttgt accgggtgct    60
attaataac                                                            69

<210> SEQ ID NO 65
<211> LENGTH: 69
<212> TYPE: DNA
<213> ORGANISM: Artificial Sequence
<220> FEATURE:
<223> OTHER INFORMATION: Synthetically generated oligonucleotide -continued

```
<400> SEQUENCE: 65
tcgagttatt aatagcaccc ggtacaagca ggattacaac aatattcaca gcagtaattg    60
ctactattc                                                            69

<210> SEQ ID NO 66
<211> LENGTH: 21
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 9
<223> OTHER INFORMATION: Xaa = one of any amino acid;
<220> FEATURE:
<221> NAME/KEY: VARIANT
<222> LOCATION: 20, 21
<223> OTHER INFORMATION: Xaa 20 = Asp, Xaa21 = Phe

<400> SEQUENCE: 66

Asn Ser Ser Asn Tyr Cys Cys Glu Xaa Cys Cys Asn Pro Ala Cys Thr
1               5                   10                  15

Gly Cys Tyr Xaa Xaa
            20

<210> SEQ ID NO 67
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 67

Gln Ser Ser Asn Tyr Cys Cys Glu Tyr Cys Cys Asn Pro Ala Cys Thr
1               5                   10                  15

Gly Cys Tyr

<210> SEQ ID NO 68
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 68

Asn Thr Ser Asn Tyr Cys Cys Glu Tyr Cys Cys Asn Pro Ala Cys Thr
1               5                   10                  15

Gly Cys Tyr

<210> SEQ ID NO 69
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 69

Asn Leu Ser Asn Tyr Cys Cys Glu Tyr Cys Cys Asn Pro Ala Cys Thr
1               5                   10                  15

Gly Cys Tyr

<210> SEQ ID NO 70
<211> LENGTH: 19
```

<212> TYPE: PRT
<213> ORGANISM: Artificial Sequence
<220> FEATURE:
<223> OTHER INFORMATION: Synthetically generated peptide

<400> SEQUENCE: 70

Asn Ile Ser Asn Tyr Cys Cys Glu Tyr Cys Cys Asn Pro Ala Cys Thr
1               5                   10                  15

Gly Cys Tyr

<210> SEQ ID NO 71
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 71

Asn Ser Ser Gln Tyr Cys Cys Glu Tyr Cys Cys Asn Pro Ala Cys Thr
1               5                   10                  15

Gly Cys Tyr

<210> SEQ ID NO 72
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 72

Ser Ser Asn Tyr Cys Cys Glu Tyr Cys Cys Asn Pro Ala Cys Thr Gly
1               5                   10                  15

Cys Tyr

<210> SEQ ID NO 73
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 73

Gln Ser Ser Gln Tyr Cys Cys Glu Tyr Cys Cys Asn Pro Ala Cys Thr
1               5                   10                  15

Gly Cys Tyr

<210> SEQ ID NO 74
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 74

Ser Ser Gln Tyr Cys Cys Glu Tyr Cys Cys Asn Pro Ala Cys Thr Gly
1               5                   10                  15

Cys Tyr

<210> SEQ ID NO 75
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 75

Asn Ser Ser Asn Tyr Cys Cys Glu Ala Cys Cys Asn Pro Ala Cys Thr
1               5                   10                  15

Gly Cys Tyr

<210> SEQ ID NO 76
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 76

Asn Ser Ser Asn Tyr Cys Cys Glu Arg Cys Cys Asn Pro Ala Cys Thr
1               5                   10                  15

Gly Cys Tyr

<210> SEQ ID NO 77
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 77

Asn Ser Ser Asn Tyr Cys Cys Glu Asn Cys Cys Asn Pro Ala Cys Thr
1               5                   10                  15

Gly Cys Tyr

<210> SEQ ID NO 78
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 78

Asn Ser Ser Asn Tyr Cys Cys Glu Asp Cys Cys Asn Pro Ala Cys Thr
1               5                   10                  15

Gly Cys Tyr

<210> SEQ ID NO 79
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 79

Asn Ser Ser Asn Tyr Cys Cys Glu Cys Cys Cys Asn Pro Ala Cys Thr
1               5                   10                  15

Gly Cys Tyr

<210> SEQ ID NO 80
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 80

Asn Ser Ser Asn Tyr Cys Cys Glu Gln Cys Cys Asn Pro Ala Cys Thr

<210> SEQ ID NO 81
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 81

Asn Ser Ser Asn Tyr Cys Cys Glu Glu Cys Cys Asn Pro Ala Cys Thr
1               5                   10                  15

Gly Cys Tyr

<210> SEQ ID NO 82
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 82

Asn Ser Ser Asn Tyr Cys Cys Glu Gly Cys Cys Asn Pro Ala Cys Thr
1               5                   10                  15

Gly Cys Tyr

<210> SEQ ID NO 83
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 83

Asn Ser Ser Asn Tyr Cys Cys Glu His Cys Cys Asn Pro Ala Cys Thr
1               5                   10                  15

Gly Cys Tyr

<210> SEQ ID NO 84
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 84

Asn Ser Ser Asn Tyr Cys Cys Glu Ile Cys Cys Asn Pro Ala Cys Thr
1               5                   10                  15

Gly Cys Tyr

<210> SEQ ID NO 85
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 85

Asn Ser Ser Asn Tyr Cys Cys Glu Lys Cys Cys Asn Pro Ala Cys Thr
1               5                   10                  15

Gly Cys Tyr

-continued

```
<210> SEQ ID NO 86
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 86

Asn Ser Ser Asn Tyr Cys Cys Glu Met Cys Cys Asn Pro Ala Cys Thr
1               5                   10                  15

Gly Cys Tyr

<210> SEQ ID NO 87
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 87

Asn Ser Ser Asn Tyr Cys Cys Glu Phe Cys Cys Asn Pro Ala Cys Thr
1               5                   10                  15

Gly Cys Tyr

<210> SEQ ID NO 88
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 88

Asn Ser Ser Asn Tyr Cys Cys Glu Pro Cys Cys Asn Pro Ala Cys Thr
1               5                   10                  15

Gly Cys Tyr

<210> SEQ ID NO 89
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 89

Asn Ser Ser Asn Tyr Cys Cys Glu Ser Cys Cys Asn Pro Ala Cys Thr
1               5                   10                  15

Gly Cys Tyr

<210> SEQ ID NO 90
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 90

Asn Ser Ser Asn Tyr Cys Cys Glu Thr Cys Cys Asn Pro Ala Cys Thr
1               5                   10                  15

Gly Cys Tyr

<210> SEQ ID NO 91
<211> LENGTH: 19
<212> TYPE: PRT
```

```
<213> ORGANISM: Artificial Sequence
<220> FEATURE:
<223> OTHER INFORMATION: Synthetically generated peptide

<400> SEQUENCE: 91

Asn Ser Ser Asn Tyr Cys Cys Glu Trp Cys Cys Asn Pro Ala Cys Thr
1               5                   10                  15

Gly Cys Tyr

<210> SEQ ID NO 92
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 92

Asn Ser Ser Asn Tyr Cys Cys Glu Val Cys Cys Asn Pro Ala Cys Thr
1               5                   10                  15

Gly Cys Tyr

<210> SEQ ID NO 93
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 93

Cys Cys Glu Ala Cys Cys Asn Pro Ala Cys Thr Gly Cys Tyr
1               5                   10

<210> SEQ ID NO 94
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 94

Cys Cys Glu Arg Cys Cys Asn Pro Ala Cys Thr Gly Cys Tyr
1               5                   10

<210> SEQ ID NO 95
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 95

Cys Cys Glu Asn Cys Cys Asn Pro Ala Cys Thr Gly Cys Tyr
1               5                   10

<210> SEQ ID NO 96
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 96

Cys Cys Glu Asp Cys Cys Asn Pro Ala Cys Thr Gly Cys Tyr
1               5                   10
```

<210> SEQ ID NO 97
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 97

Cys Cys Glu Cys Cys Cys Asn Pro Ala Cys Thr Gly Cys Tyr
1               5                   10

<210> SEQ ID NO 98
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 98

Cys Cys Glu Gln Cys Cys Asn Pro Ala Cys Thr Gly Cys Tyr
1               5                   10

<210> SEQ ID NO 99
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 99

Cys Cys Glu Glu Cys Cys Asn Pro Ala Cys Thr Gly Cys Tyr
1               5                   10

<210> SEQ ID NO 100
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 100

Cys Cys Glu Gly Cys Cys Asn Pro Ala Cys Thr Gly Cys Tyr
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 101

Cys Cys Glu His Cys Cys Asn Pro Ala Cys Thr Gly Cys Tyr
1               5                   10

<210> SEQ ID NO 102
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 102

Cys Cys Glu Ile Cys Cys Asn Pro Ala Cys Thr Gly Cys Tyr
1               5                   10

<210> SEQ ID NO 103

```
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 103

Cys Cys Glu Lys Cys Cys Asn Pro Ala Cys Thr Gly Cys Tyr
1               5                   10

<210> SEQ ID NO 104
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 104

Cys Cys Glu Met Cys Cys Asn Pro Ala Cys Thr Gly Cys Tyr
1               5                   10

<210> SEQ ID NO 105
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 105

Cys Cys Glu Phe Cys Cys Asn Pro Ala Cys Thr Gly Cys Tyr
1               5                   10

<210> SEQ ID NO 106
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 106

Cys Cys Glu Pro Cys Cys Asn Pro Ala Cys Thr Gly Cys Tyr
1               5                   10

<210> SEQ ID NO 107
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 107

Cys Cys Glu Ser Cys Cys Asn Pro Ala Cys Thr Gly Cys Tyr
1               5                   10

<210> SEQ ID NO 108
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 108

Cys Cys Glu Thr Cys Cys Asn Pro Ala Cys Thr Gly Cys Tyr
1               5                   10

<210> SEQ ID NO 109
<211> LENGTH: 14
```

```
<212> TYPE: PRT
<213> ORGANISM: Artificial Sequence
<220> FEATURE:
<223> OTHER INFORMATION: Synthetically generated peptide

<400> SEQUENCE: 109

Cys Cys Glu Trp Cys Cys Asn Pro Ala Cys Thr Gly Cys Tyr
1               5                   10

<210> SEQ ID NO 110
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 110

Cys Cys Glu Val Cys Cys Asn Pro Ala Cys Thr Gly Cys Tyr
1               5                   10

<210> SEQ ID NO 111
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 111

Gln His Asn Pro Arg
1               5

<210> SEQ ID NO 112
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 112

Val Gln His Asn Pro Arg
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 113

Val Arg Gln His Asn Pro Arg
1               5

<210> SEQ ID NO 114
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 114

Val Arg Gly Gln His Asn Pro Arg
1               5

<210> SEQ ID NO 115
<211> LENGTH: 9
<212> TYPE: PRT
```

<213> ORGANISM: Artificial Sequence
<220> FEATURE:
<223> OTHER INFORMATION: Synthetically generated peptide

<400> SEQUENCE: 115

Val Arg Gly Pro Gln His Asn Pro Arg
1               5

<210> SEQ ID NO 116
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 116

Val Arg Gly Pro Arg Gln His Asn Pro Arg
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 117

Val Arg Gly Pro Arg Arg Gln His Asn Pro Arg
1               5                   10

<210> SEQ ID NO 118
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 118

Arg Gln His Asn Pro Arg
1               5

<210> SEQ ID NO 119
<211> LENGTH: 21
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 2, 3, 4, 5, 8, 9, 12, 13, 14, 16, 17, 19, 20, 21
<223> OTHER INFORMATION: Xaa = one of any amino acid

<400> SEQUENCE: 119

Xaa Xaa Xaa Xaa Xaa Cys Cys Xaa Xaa Cys Cys Xaa Xaa Xaa Cys Xaa
1               5                   10                  15

Xaa Cys Xaa Xaa Xaa
            20

<210> SEQ ID NO 120
<211> LENGTH: 21
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 8
<223> OTHER INFORMATION: Xaa = Glu or Asp

```
<220> FEATURE:
<221> NAME/KEY: VARIANT
<222> LOCATION: 9
<223> OTHER INFORMATION: Xaa = Leu, Ile, Val, Trp, Tyr or Phe
<220> FEATURE:
<221> NAME/KEY: VARIANT
<222> LOCATION: 16
<223> OTHER INFORMATION: Xaa =  Thr, Ala, or Trp
<220> FEATURE:
<221> NAME/KEY: VARIANT
<222> LOCATION: 19
<223> OTHER INFORMATION: Xaa = Trp, Tyr, Or Leu

<400> SEQUENCE: 120

Asn Ser Ser Asn Tyr Cys Cys Xaa Xaa Cys Cys Asn Pro Ala Cys Xaa
1               5                   10                  15

Gly Cys Xaa Asp Phe
            20

<210> SEQ ID NO 121
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 121

Asn Ser Ser Asn Tyr
1               5

<210> SEQ ID NO 122
<211> LENGTH: 30
<212> TYPE: PRT
<213> ORGANISM: Yersinia enterocolitica

<400> SEQUENCE: 122

Gln Ala Cys Asp Pro Pro Leu Pro Pro Ala Glu Val Ser Ser Asp Trp
1               5                   10                  15

Asp Cys Cys Asp Val Cys Cys Asn Pro Ala Cys Ala Gly Cys
            20                  25                  30

<210> SEQ ID NO 123
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 123

Lys Lys Lys Lys Lys Lys
1               5

<210> SEQ ID NO 124
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 124

Asp Lys Lys Lys Lys Lys Lys
1               5

<210> SEQ ID NO 125
<211> LENGTH: 14
<212> TYPE: PRT
<213> ORGANISM: Artificial Sequence
```

-continued

```
<220> FEATURE:
<223> OTHER INFORMATION: Synthetically generated peptide
<220> FEATURE:
<221> NAME/KEY: VARIANT
<222> LOCATION: 4
<223> OTHER INFORMATION: Xaa = Phe, Trp or Tyr

<400> SEQUENCE: 125

Cys Cys Glu Xaa Cys Cys Asn Pro Ala Cys Thr Gly Cys Tyr
1               5                   10
```

METHODS AND COMPOSITIONS FOR THE TREATMENT OF GASTROINTESTINAL DISORDERS

CLAIM OF PRIORITY

This application is a divisional of U.S. application Ser. No. 10/766,735, filed Jan. 28, 2004, now abandoned and claims priority under 35 USC §119(e) to U.S. Provisional Patent Application Ser. No. 60/443,098, filed on Jan. 28, 2003; U.S. Provisional Patent Application Ser. No. 60/471,288, filed on May 15, 2003 and U.S. Provisional Patent Application Ser. No. 60/519,460, filed on Nov. 12, 2003, the entire contents of which are hereby incorporated by reference.

TECHNICAL FIELD

This invention relates to methods and compositions for treating various disorders, including gastrointestinal disorders, obesity, congestive heart failure and benign prostatic hyperplasia.

BACKGROUND

Irritable bowel syndrome (IBS) is a common chronic disorder of the intestine that affects 20 to 60 million individuals in the US alone (Lehman Brothers, Global Healthcare-Irritable bowel syndrome industry update, September 1999). IBS is the most common disorder diagnosed by gastroenterologists (28% of patients examined) and accounts for 12% of visits to primary care physicians (Camilleri 2001, Gastroenterology 120:652-668). In the US, the economic impact of IBS is estimated at $25 billion annually, through direct costs of health care use and indirect costs of absenteeism from work (Talley 1995, Gastroenterology 109:1736-1741). Patients with IBS have three times more absenteeism from work and report a reduced quality of life. Sufferers may be unable or unwilling to attend social events, maintain employment, or travel even short distances (Drossman 1993, Dig Dis Sci 38:1569-1580). There is a tremendous unmet medical need in this population since few prescription options exist to treat IBS.

Patients with IBS suffer from abdominal pain and a disturbed bowel pattern. Three subgroups of IBS patients have been defined based on the predominant bowel habit: constipation-predominant (c-IBS), diarrhea-predominant (d-IBS) or alternating between the two (a-IBS). Estimates of individuals who suffer from c-IBS range from 20-50% of the IBS patients with 30% frequently cited. In contrast to the other two subgroups that have a similar gender ratio, c-IBS is more common in women (ratio of 3:1), (Talley et al. 1995, Am J Epidemiol 142:76-83).

The definition and diagnostic criteria for IBS have been formalized in the "Rome Criteria" (Drossman et al. 1999, Gut 45:Suppl II: 1-81), which are well accepted in clinical practice. However, the complexity of symptoms has not been explained by anatomical abnormalities or metabolic changes. This has led to the classification of IBS as a functional-GI disorder, which is diagnosed on the basis of the Rome criteria and limited evaluation to exclude organic disease. (Ringel et al. 2001, Annu Rev Med 52: 319-338). IBS is considered to be a "biopsychosocial" disorder resulting from a combination of three interacting mechanisms: altered bowel motility, an increased sensitivity of the intestine or colon to pain stimuli (visceral sensitivity) and psychosocial factors (Camilleri 2001, Gastroenterology 120:652-668). Recently, there has been increasing evidence for a role of inflammation in etiology of IBS. Reports indicate that subsets of IBS patients have small but significant increases in colonic inflammatory and mast cells, increased inducible nitric oxide (NO) and synthase (iNOS) and altered expression of inflammatory cytokines (reviewed by Talley 2000, Medscape Coverage of DDW week).

SUMMARY

The present invention features compositions and related methods for treating IBS and other gastrointestinal disorders and conditions (e.g., gastrointestinal motility disorders, functional gastrointestinal disorders, gastroesophageal reflux disease (GERD), Crohn's disease, ulcerative colitis, Inflammatory bowel disease, functional heartburn, dyspepsia (including functional dyspepsia or nonulcer dyspepsia), gastroparesis, chronic intestinal pseudo-obstruction (or colonic pseudo-obstruction), and disorders and conditions associated with constipation, e.g., constipation associated with use of opiate pain killers, post-surgical constipation, and constipation associated with neuropathic disorders as well as other conditions and disorders. The compositions feature peptides that activate the guanylate cyclase C (GC-C) receptor.

The present invention also features compositions and related methods for treating obesity, congestive heart failure and benign prostatic hyperplasia, (BPH).

Without being bound by any particular theory, in the case of IBS and other gastrointestinal disorders the peptides are useful because they can increase gastrointestinal motility.

Without being bound by any particular theory, in the case of IBS and other gastrointestinal disorders the peptides are, useful, in part, because they can decrease inflammation.

Without being bound by any particular theory, in the case of IBS and other gastrointestinal disorders the peptides are also useful because they can decrease gastrointestinal pain or visceral pain.

The invention features pharmaceutical compositions comprising certain peptides that are capable of activating the guanylate-cyclase C (GC-C) receptor. Also within the invention are pharmaceutical compositions comprising a peptide of the invention as well as combination compositions comprising a peptide of the invention and a second therapeutic agent, e.g., an agent for treating constipation (e.g., SPI-0211; Sucampo Pharmaceuticals, Inc.; Bethesda, Md.) or some other gastrointestinal disorder. Examples of a second therapeutic agent include: acid reducing agents such as proton pump inhibitors and H2 receptor blockers, pro-motility agents such as 5HT receptor agonists (e.g. Zelnorm®), anti-inflammatory agents, antispasmodics, antidepressants, centrally-acting analgesic agents such as opiod receptor agonists, opiod receptor antagonists, agents for the treatment of Inflammatory bowel disease, Crohn's disease and ulcerative colitis (e.g., Traficet-EN™ (ChemoCentryx, Inc.; San Carlos, Calif.) agents that treat gastrointestinal or visceral pain and cGMP phosphodiesterase inhibitors (motapizone, zaprinast, and suldinac sulfone). Thus, for example, the pharmaceutical compositions can include an analgesic agent, selected from the group consisting of: Ca channel blockers (e.g., ziconotide), 5HT receptor antagonists (for example 5HT3, 5HT4 and 5HT1 receptor antagonists), opioid receptor agonists (e.g., loperamide, fedotozine, and fentanyl, naloxone, naltrexone, methyl nalozone, nalmefene, cypridime, beta funaltrexamine, naloxonazine, naltrindole, and nor-binaltorphimine, morphine, diphenyloxylate, enkephalin pentapeptide, and trimebutine), NK1 receptor antagonists (e.g., ezlopitant and SR-14033), CCK receptor agonists (e.g., loxiglumide), NK1 receptor antagonists, NK3 receptor antagonists (e.g., talnetant, osanetant (SR-142801)), norepinephrine-serotonin-reuptake inhibitors (NSRI; e.g., milnacipran), vanilloid and cannabanoid receptor agonists (e.g., arvanil), sialorphin, sialorphin-related peptides comprising the amino acid sequence QHNPR (SEQ ID NO:111) for example, VQHNPR (SEQ ID NO:112); VRQHNPR (SEQ ID NO:113); VRGQHNPR (SEQ ID NO:114); VRGPQHNPR (SEQ ID NO:115); VRGPRQHNPR, (SEQ ID NO:116); VRGPRRQHNPR (SEQ ID NO:117); and RQHNPR (SEQ ID NO:118), compounds or peptides that are inhibitors of neprilysin, frakefamide (H-Tyr-D-Ala-Phe(F)-Phe-NH$_2$; WO 01/019849 A1), loperamide, Tyr-Arg (kyotorphin), CCK receptor agonists (caerulein), conotoxin peptides, peptide analogs of thymulin, loxiglumide, dexloxiglumide (the R-isomer of loxiglumide) (WO 88/05774) and other analgesic peptides or compounds can be used with or linked to the peptides of the invention.

The invention includes methods for treating various gastrointestinal disorders by administering a peptide that acts as a partial or complete agonist of the GC-C receptor. The peptide includes at least six cysteines that form three disulfide bonds. In certain embodiments the disulfide bonds are replaced by other covalent cross-links and in some cases the cysteines are substituted by other residues to provide for alternative covalent cross-links. The peptides may also include at least one trypsin or chymotrypsin cleavage site and/or carboxy-terminal analgesic peptide or small molecule, e.g., AspPhe or some other analgesic peptide. When present within the peptide, the analgesic peptide or small molecule may be preceded by a chymotrypsin or trypsin cleavage site that allows release of the analgesic peptide or small molecule. The peptides and methods of the invention are also useful for treating pain and inflammation associated with various disorders, including gastrointestinal disorders. Certain peptides include a functional chymotrypsin or trypsin cleavage site located so as to allow inactivation of the peptide upon cleavage. Certain peptides having a functional cleavage site undergo cleavage and gradual inactivation in the digestive tract, and this is desirable in some circumstances. In certain peptides, a functional chymotrypsin site is altered, increasing the stability of the peptide in vivo.

The invention includes methods for treating other disorders such as congestive heart failure and benign prostatic hyperplasia by administering a peptide or small molecule (parenterally or orally) that acts as an agonist of the GC-C receptor. Such agents can be used in combination with natriuretic peptides (e.g., atrial natriuretic peptide, brain natriuretic peptide or C-type naturetic peptide), a diuretic, or an inhibitor of angiotensin converting enzyme.

The invention features methods and compositions for increasing intestinal motility. Intestinal motility involves spontaneous coordinated dissentions and contractions of the stomach, intestines, colon and rectum to move food through the gastrointestinal tract during the digestive process.

In certain embodiments the peptides include either one or two or more contiguous negatively charged amino acids (e.g., Asp or Glu) or one or two or more contiguous positively charged residues (e.g., Lys or Arg) or one or two, or more contiguous positively or negatively charged amino acids at the carboxy terminus. In these embodiments all of the flanking amino acids at the carboxy terminus are either positively or negatively charged. In other embodiments the carboxy terminal charged amino acids are preceded by a Leu. For example the following amino acid sequences can be added to the carboxy terminus of the peptide: Asp; Asp Lys; Lys Lys Lys Lys Lys Lys (SEQ ID NO:123); Asp Lys Lys Lys Lys Lys Lys (SEQ ID NO:124); Leu Lys Lys; and Leu Asp. It is also possible to simply add Leu at the carboxy terminus.

In a first aspect, the invention features a peptide comprising, consisting of, or consisting essentially of the amino acid sequence (1): $Xaa_1$ $Xaa_2$ $Xaa_3$ $Xaa_4$ $Xaa_5$ $Cys_6$ $Cys_7$ $Xaa_8$ $Xaa_9$ $Cys_{10}$ $Cys_{11}$ $Xaa_{12}$ $Xaa_{13}$ $Xaa_{14}$ $Cys_{15}$ $Xaa_{16}$ $Xaa_{17}$ $Cys_{18}$ $Xaa_{19}$ $Xaa_{20}$ $Xaa_{21}$ (SEQ ID NO:119) wherein: $Xaa_1$ $Xaa_2$ $Xaa_3$ $Xaa_4$ $Xaa_5$ is Asn Ser Ser Asn Tyr (SEQ ID NO:121) or is missing or $Xaa_1$ $Xaa_2$ $Xaa_3$ $Xaa_4$ is missing. In certain embodiments $Xaa_8$, $Xaa_9$, $Xaa_{12}$, $Xaa_{13}$, $Xaa_{14}$, $Xaa_{17}$, and $Xaa_{19}$ can be any amino acid. In certain embodiments $Xaa_5$ is Asn, Trp, Tyr, Asp, or Phe. In other embodiments, $Xaa_5$ can also be Thr or Ile. In other embodiments $Xaa_5$ is Tyr, Asp or Trp. In some embodiments $Xaa_8$ is Glu, Asp, Gln, Gly or Pro. In other embodiments $Xaa_8$ is Glu; in some embodiments $Xaa_9$ is Leu, Ile, Val, Ala, Lys, Arg, Trp, Tyr or Phe in some embodiments. $Xaa_9$ is Leu, Ile, Val, Lys, Arg, Trp, Tyr or Phe.

In certain embodiments, an amino acid can be replace by a non-naturally occurring amino acid or a naturally or non-naturally occurring amino acid analog. For example, an aromatic amino acid can be replaced by 3,4-dihydroxy-L-phenylalanine, 3-iodo-L-tyrosine, triiodothyronine, L-thyroxine, phenylglycine (Phg) or nor-tyrosine (norTyr). Phg and norTyr and other amino acids including Phe and Tyr can be substituted by, e.g., a halogen, —CH3, —OH, —CH$_2$NH$_3$, —C(O) H, —CH$_2$CH$_3$, —CN, —CH$_2$CH$_2$CH$_3$, —SH, or another group.

In some embodiments $Xaa_{12}$ is Asn, Tyr, Asp or Ala. In other embodiments $Xaa_{12}$ is Asn. In some embodiments $Xaa_{13}$ is Ala, Pro or Gly, and in other embodiments it is Pro. In some embodiments $Xaa_{14}$ is Ala, Leu, Ser, Gly, Val, Glu, Gln, Ile, Leu, Lys, Arg, or Asp, and in other embodiments it is Ala or Gly, and in still other embodiments it is Ala. In some embodiments $Xaa_{16}$ is Thr, Ala, Asn, Lys, Arg, Trp; $Xaa_{17}$ is Gly, Pro or Ala; $Xaa_{19}$ is selected from Trp, Tyr, Phe, Asn and Leu or $Xaa_{19}$ is selected from Trp, Tyr, and Phe or $Xaa_{19}$ is selected from Leu, Ile and Val; or $Xaa_{19}$ is His or $Xaa_{19}$ is selected from Trp, Tyr, Phe, Asn, Ile, Val, His and Leu; and $Xaa_{20}$ $Xaa_{21}$ is AspPhe or is missing or $Xaa_{20}$ is Asn or Glu and $Xaa_{21}$ is missing or $Xaa_{19}$ $Xaa_{20}$ $Xaa_{21}$ is missing. The invention also features methods for treating a gastrointestinal disorder (e.g., a gastrointestinal motility disorder, a functional gastrointestinal disorder, gastroesophageal reflux disease, functional heartburn, dyspepsia, functional dyspepsia, nonulcer dyspepsia, gastroparesis, chronic intestinal pseudo-obstruction, colonic pseudo-obstruction), obesity, congestive heart failure or benign prostatic hyperplasia by administering a composition comprising an aforementioned peptide When $Xaa_9$ is Trp, Tyr or Phe or when $Xaa_{16}$ is Trp the peptide has a potentially functional chymotrypsin cleavage site that is located at a position where cleavage will inactivate GC-C receptor binding by the peptide. When $Xaa_9$ is Lys or Arg or when $Xaa_{16}$ is Lys or Arg, the peptide has a potentially functional trypsin cleavage site that is located at a position where cleavage will inactivate GC-C receptor binding by the peptide.

When $Xaa_{19}$ is Trp, Tyr or Phe, the peptide has a chymotrypsin cleavage site that is located at a position where cleavage will liberate the portion of the peptide carboxy-terminal to $Xaa_{19}$. When $Xaa_{19}$ is Leu, Ile or Val, the peptide can have a chymotrypsin cleavage site that is located at a position where cleavage will liberate the portion of the peptide amino-terminal to $Xaa_{19}$. At relatively high pH the same effect is seen when $Xaa_{19}$ is His. When $Xaa_{19}$ is Lys or Arg, the peptide has a trypsin cleavage site that is located at a position where cleavage will liberate portion of the peptide carboxy-terminal to $Xaa_{19}$. Thus, if the peptide includes an analgesic peptide carboxy-terminal to $Xaa_{19}$, the peptide will be liberated in the digestive tract upon exposure to the appropriate protease. Among the analgesic peptides which can be included in the peptide are: AspPhe (as $Xaa_{20} Xaa_{21}$), endomorphin-1, endomorphin-2, nocistatin, dalargin, lupron, and substance P and other analgesic peptides described herein. These peptides can, for example, be used to replace $Xaa_{20} Xaa_{21}$.

When $Xaa_1$ or the amino-terminal amino acid of the peptide of the invention (e.g., $Xaa_2$ or $Xaa_3$) is Trp, Tyr or Phe, the peptide has a chymotrypsin cleavage site that is located at a position where cleavage will liberate the portion of the peptide amino-terminal to $Xaa_1$ (or $Xaa_2$ or $Xaa_3$) along with $Xaa_1$, $Xaa_2$ or $Xaa_3$. When $Xaa_1$ or the amino-terminal amino acid of the peptide of the invention (e.g., $Xaa_2$ or $Xaa_3$) is Lys or Arg, the peptide has a trypsin cleavage site that is located at a position where cleavage will liberate portion of the peptide, amino-terminal to $Xaa_1$ along with $Xaa_1$, $Xaa_2$ or $Xaa_3$). When $Xaa_1$ or the amino-terminal amino acid of the peptide of the invention is Leu, Ile or Val, the peptide can have a chymotrypsin cleavage site that is located at a position where cleavage will liberate the portion of the peptide amino-terminal to $Xaa_1$. At relatively high pH the same effect is seen when $Xaa_1$ is His. Thus, for example, if the peptide includes an analgesic peptide amino-terminal to $Xaa_1$, the peptide will be liberated in the digestive tract upon exposure to the appropriate protease. Among the analgesic peptides which can be included in the peptide are: AspPhe, endomorphin-1, endomorphin-2, nocistatin, dalargin, lupron, and substance p and other analgesic peptides described herein.

When fully folded, disulfide bonds are present between: $Cys_6$ and $Cys_{11}$; $Cys_7$ and $Cys_{15}$; and $Cys_{10}$ and $Cys_{18}$. The peptides of the invention bear some sequence similarity to ST peptides. However, they include amino acid changes and/or additions that improve functionality. These changes can, for example, increase or decrease activity (e.g., increase or decrease the ability of the peptide to stimulate intestinal motility), alter the ability of the peptide to fold correctly, the stability of the peptide, the ability of the peptide to bind the GC-C receptor and/or decrease toxicity. In some cases the peptides may function more desirably than wild-type ST peptide. For example, they may limit undesirable side effects such as diarrhea and dehydration.

In some embodiments one or both members of one or more pairs of Cys residues which normally form a disulfide bond can be replaced by homocysteine, 3-mercaptoproline (Kolodziej et al. 1996 Int J Pept Protein Res 48:274); β,β dimethylcysteine (Hunt et al. 1993 Int J Pept Protein Res 42:249) or diaminoproprionic acid (Smith et al. 1978 J Med Chem 21:117) to form alternative internal cross-links at the positions of the normal disulfide bonds.

In addition, one or more disulfide bonds can be replaced by alternative covalent cross-links, e.g., an amide bond, an ester linkage, an alkyl linkage, a thio ester linkage, a lactam bridge, a carbamoyl, linkage, a urea linkage, a thiourea linkage, a phosphonate ester linkage, an alkyl linkage, and alkenyl linkage, an ether, a thioether linkage, or amino linkage. For example, Ledu et al. (Proceedings Nat'l Acad. Sci. 100:11263-78, 2003) described, methods for preparing lactam and amide cross-links. Schafmeister et al. (J. Am. Chem. Soc. 122:5891, 2000) describes stable, all carbon cross-links. In some cases, the generation of such alternative cross-links requires, replacing the Cys residues with other residues such as Lys or Glu or non-naturally occurring amino acids.

In the case of a peptide comprising the sequence (I): $Xaa_1$ $Xaa_2$ $Xaa_3$ $Xaa_4$ $Xaa_5$ $Cys_6$ $Cys_7$ $Xaa_8$ $Xaa_9$ $Cys_{10}$ $Cys_{11}$ $Xaa_{12}$ $Xaa_{13}$ $Xaa_{14}$ $Cys_{15}$ $Xaa_{16}$ $Xaa_{17}$ $Cys_{18}$ $Xaa_{19}$ $Xaa_{20}$ $Xaa_{21}$ (SEQ ID NO:119) wherein: $Xaa_1$ $Xaa_2$ $Xaa_3$ $Xaa_4$ $Xaa_5$ is missing and/or the sequence $Xaa_{19}$ $Xaa_{20}$ $Xaa_{21}$ is missing, the peptide can still contain additional carboxyterminal or amino terminal amino acids or both. For example, the peptide can include an amino terminal sequence that facilitates recombinant production of the peptide and is cleaved prior to administration of the peptide to a patient. The peptide can also include other amino terminal or carboxyterminal amino acids. In some cases the additional amino acids protect the peptide, stabilize the peptide or alter the activity of the peptide. In some cases some or all of these additional amino acids are removed, prior to administration of the peptide to a patient. The peptide can include 1, 2, 3, 4, 5, 10, 15, 20, 25, 30, 40, 50, 60, 70 80, 90, 100 or more amino acids at its amino terminus or carboxy terminus or both. The number of flanking amino acids need not be the same. For example, there can be 10 additional amino acids at the amino terminus of the peptide and none at the carboxy terminus.

In one embodiment the peptide comprises the amino acid sequence (I): $Xaa_1$ $Xaa_2$ $Xaa_3$ $Xaa_4$ $Xaa_5$ $Cys_6$ $Cys_7$ $Xaa_8$ $Xaa_9$ $Cys_{10}$ $Cys_{11}$ $Xaa_{12}$ $Xaa_{13}$ $Xaa_{14}$ $Cys_{15}$ $Xaa_{16}$ $Xaa_{17}$ $Cys_{18}$ $Xaa_{19}$ $Xaa_{20}$ $Xaa_{21}$ (SEQ ID NO:119) wherein: $Xaa_1$ $Xaa_2$ $Xaa_3$ $Xaa_4$ $Xaa_5$ is missing; $Xaa_8$ is Glu; $Xaa_9$ is Leu, Ile, Lys, Arg, Trp, Tyr or Phe; $Xaa_{12}$ is Asn $Xaa_{13}$ is Pro $Xaa_{14}$ is Ala; $Xaa_{16}$ is Thr, Ala, Lys, Arg, Trp; $Xaa_{17}$ is Gly; $Xaa_{19}$ is Tyr or Leu; and $Xaa_{20}$ $Xaa_{21}$ is AspPhe or is missing. Where $Xaa_{20}$ $Xaa_{21}$ and/or $Xaa_1$ $Xaa_2$ $Xaa_3$ $Xaa_4$ $Xaa_5$ are missing, there may be additional flanking amino acids in some embodiments.

In a second aspect, the invention also features a therapeutic or prophylactic method comprising administering a peptide comprising the amino acid sequence (I): $Xaa_1$ $Xaa_2$ $Xaa_3$ $Xaa_4$ $Xaa_5$ $Cys_6$ $Cys_7$ $Xaa_8$ $Xaa_9$ $Cys_{10}$ $Cys_{11}$ $Xaa_{12}$ $Xaa_{13}$ $Xaa_{14}$ $Cys_{15}$ $Xaa_{16}$ $Xaa_{17}$ $Cys_{18}$ $Xaa_{19}$ $Xaa_{20}$ $Xaa_{21}$ (SEQ ID NO:120 wherein: $Xaa_1$ $Xaa_2$ $Xaa_3$ $Xaa_4$ $Xaa_5$ is Asn Ser Ser Asn, Tyr (SEQ ID NO:121) or is missing or $Xaa_1$ $Xaa_2$ $Xaa_3$ $Xaa_4$ is, missing and $Xaa_5$ is Asn, Trp, Tyr, Asp, Ile, Thr, or Phe; $Xaa_8$ is Glu, Asp, Gln, Gly or Pro; $Xaa_9$ is Leu, Ile, Val, Ala, Lys, Arg, Trp, Tyr or Phe; $Xaa_{12}$ is Asn, Tyr, Asp or Ala; $Xaa_{13}$ is Pro or Gly; $Xaa_{14}$ is Ala, Leu, Ser, Gly, Val, Glu, Gln, Ile, Leu, Lys, Arg, and Asp; $Xaa_{16}$ is Thr, Ala, Asn, Lys, Arg, Trp; $Xaa_{17}$ is Gly, Pro or Ala; $Xaa_{19}$ is Trp, Tyr, Phe or Leu; and $Xaa_{20}$ $Xaa_{21}$ is AspPhe or is missing or $Xaa_{20}$ is Asn or Glu and $Xaa_{21}$ is missing or $Xaa_{19}$ $Xaa_{20}$ $Xaa_{21}$ is missing.

In certain embodiments of the therapeutic or prophylactic methods: the peptide comprises the amino acid sequence (I): $Xaa_1$ $Xaa_2$ $Xaa_3$ $Xaa_4$ $Xaa_5$ $Cys_6$ $Cys_7$ $Xaa_8$ $Xaa_9$ $Cys_{10}$ $Cys_{11}$ $Xaa_{12}$ $Xaa_{13}$ $Xaa_{14}$ $Cys_{15}$ $Xaa_{16}$ $Xaa_{17}$ $Cys_{18}$ $Xaa_{19}$ $Xaa_{20}$ $Xaa_{21}$ (SEQ ID NO:119) wherein: $Xaa_1$ $Xaa_2$ $Xaa_3$ $Xaa_4$ $Xaa_5$ is missing; $Xaa_8$ is Glu; $Xaa_9$ is Leu, Ile, Lys, Arg, Trp, Tyr, or Phe; $Xaa_{12}$ is Asn; $Xaa_{13}$ is Pro; $Xaa_{14}$ is Ala; $Xaa_{16}$ is Thr, Ala, Lys, Arg, Trp or $Xaa_{16}$ is any amino acid or $Xaa_{16}$ is Thr, Ala, Lys, Arg, Trp or $Xaa_{16}$ is any non-aromatic amino acid; $Xaa_{17}$ is Gly; $Xaa_{19}$ is Tyr or Leu; and $Xaa_{20}$ $Xaa_{21}$ is AspPhe or is missing.

In certain embodiments, the invention features, a purified polypeptide comprising the amino acid sequence (II):

(SEQ ID NO:120)
$Xaa_1$ $Xaa_2$ $Xaa_3$ $Xaa_4$ $Xaa_5$ $Cys_6$ $Cys_7$ $Xaa_8$ $Xaa_9$ $Cys_{10}$ $Cys_{11}$ $Asn_{12}$ $Pro_{13}$ $Ala_{14}$ $Cys_{15}$ $Xaa_{16}$ $Gly_{17}$ $Cys_{18}$ $Xaa_{19}$ $Xaa_{20}$ $Xaa_{21}$ wherein $Xaa_1$ $Xaa_2$ $Xaa_3$ $Xaa_4$ $Xaa_5$ is Asn Ser Ser -continued

```
Asn Tyr or is missing or Xaa₁ Xaa₂ Xaa₃ Xaa₄ is missing and Xaa₅ is Asn;

Xaa₈ is Glu or Asp;

Xaa₉ is Leu, Ile, Val, Trp, Tyr or Phe;

Xaa₁₆ is Thr, Ala, Trp;

Xaa₁₉ is Trp, Tyr, Phe or Leu or is missing;
and

Xaa₂₀ Xaa₂₁ is AspPhe.
```

In various preferred embodiments the invention features a purified polypeptide comprising the amino acid sequence (II): Xaa$_1$ Xaa$_2$ Xaa$_3$ Xaa$_4$ Xaa$_5$ Cys$_6$ Cys$_7$ Xaa$_8$ Xaa$_9$ Cys$_{10}$ Cys$_{11}$ Asn$_{12}$ Pro$_{13}$ Ala$_{14}$ Cys$_{15}$ Xaa$_{16}$ Gly$_{17}$ Cys$_{18}$ Xaa$_{19}$ Xaa$_{20}$ Xaa$_{21}$ (SEQ ID NO:120) wherein, Xaa$_9$ is Leu, Ile or Val and Xaa$_{16}$ is Trp, Tyr or Phe; Xaa$_9$ is Trp, Tyr or Phe, and Xaa$_{16}$ is Thr or Ala; Xaa$_{19}$ is Trp, Tyr, Phe and Xaa$_{20}$ Xaa$_{21}$ is AspPhe; and Xaa$_1$ Xaa$_2$ Xaa$_3$ Xaa$_4$ is missing and Xaa$_5$ is Asn; the peptide comprises fewer than 50, 40, 30 or 25 amino acids; fewer than five amino acid precede Cys$_6$.

The peptides can be co-administered with or linked, e.g., covalently linked to any of a variety of other peptides including analgesic peptides or analgesic compounds. For example, a therapeutic peptide of the invention can be linked to an analgesic agent selected from the group consisting of: Ca channel blockers (e.g., ziconotide), complete or partial 5HT receptor antagonists, (for example 5HT3, 5HT4 and 5HT1 receptor antagonists), complete or partial 5HT receptor agonists including, 5HT3, 5HT4 (for example tegaserod, mosapride and renzapride) and 5HT1 receptor agonists, CRF receptor agonists (NBI-34041), β-3 adrenoreceptor agonists, opioid receptor agonists (e.g., loperamide, fedotozine, and fentanyl, naloxone, naltrexone, methyl nalozone, nalmefene, cypridime, beta funaltrexamine, naloxonazine, naltrindole, and nor-binaltorphimine, morphine, diphenyloxylate, enkephalin pentapeptide, asimadoline, and trimebutine), NK1 receptor antagonists (e.g., ezlopitant and SR-14033), CCK receptor agonists (e.g., loxiglumide), NK1 receptor antagonists, NK3 receptor antagonists (e.g., talnetant, osanetant (SR-14801)), norepinephrine-serotonin reuptake inhibitors (NSRI; e.g., milnacipran), vanilloid and cannabanoid receptor agonists (e.g., arvanil), sialorphin, sialorphin-related peptides comprising the amino acid sequence QHNPR (SEQ ID NO:111) for example, VQHNPR (SEQ ID NO:112); VRQHNPR (SEQ ID NO:113); VRGQHNPR (SEQ ID NO:114); VRGPQHNPR (SEQ ID NO:115); VRG-PRQHNPR (SEQ ID NO:116); VRGPRRQHNPR (SEQ ID NO:117); and RQHNPR (SEQ ID NO:118), compounds or peptides that are inhibitors of neprilysin, frakefamide (H-Tyr-D-Ala-Phe(F)-Phe-NH$_2$; WO 01/019849 A1), loperamide, Tyr-Arg (kyotorphin), CCK receptor agonists (caerulein), conotoxin peptides, peptide analogs of thymulin, loxiglumide, dexloxiglumide (the R-isomer of loxiglumide) (WO 88/05774) and other analgesic peptides or compounds can be used with or linked to the peptides of the invention.

Amino acid, non-amino acid, peptide and non-peptide spacers can be interposed between a peptide that is a GC-C receptor agonist and a peptide that has some other biological function, e.g., an analgesic peptide or a peptide used to treat obesity. The linker can be one that is cleaved from the flanking peptides in vivo or one that remains linked to the flanking peptides in vivo. For example, glycine, beta-alanine, glycyl-glycine, glycyl-beta-alanine, gamma-aminobutyric acid, 6-aminocaproic acid, L-phenylalanine, L-tryptophan and glycyl-L-valil-L-phenylalanine can be used as a spacer (Chaltin et al. 2003 Helvetica Chimica Acta 86:533-547; Caliceti et al. 1993 FARMCO 48:919-32) as can polyethylene glycols (Butterworth et al. 1987 J. Med. Chem 30:1295-302) and maleimide derivatives (King et al. 2002 Tetrahedron Lett. 43:1987-1990). Various other linkers are described in the literature (Nestler 1996 Molecular Diversity 2:35-42; Finn et al. 1984 Biochemistry 23:2554-8; Cook et al. 1994 Tetrahedron Lett. 35:6777-80; Brokx et al. 2002 Journal of Controlled Release 78:115-123; Griffin et al. 2003 J. Am. Chem. Soc. 125:6517-6531; Robinson et al. 1998 Proc. Natl. Acad. Sci. USA 95:5929-5934.

The peptides can include the amino acid sequence of a peptide that occurs naturally in a vertebrate (e.g., mammalian) species or in a bacterial species. In addition, the peptides can be partially or completely non-naturally occurring peptides. Also within the invention are peptidomimetics corresponding to the peptides of the invention. In various embodiments, the patient is suffering from a gastrointestinal disorder; the patient is suffering from a disorder selected from the group consisting of: a gastrointestinal motility disorder, irritable bowel syndrome, chronic constipation, a functional gastrointestinal disorder, gastroesophageal reflux disease, functional heartburn, dyspepsia, functional dyspepsia, non-ulcer dyspepsia, gastroparesis, chronic intestinal pseudo-obstruction, Crohn's disease, ulcerative colitis, Irritable bowel syndrome, colonic pseudo-obstruction, obesity, congestive heart failure, or benign prostatic hyperplasia; the composition is administered orally; the peptide comprises 30 or fewer amino acids, the peptide comprises 20 or fewer amino acids, and the peptide comprises no more than 5 amino acids prior to Cys$_6$; the peptide comprises 150, 140, 130, 120, 110, 100, 90, 80, 70, 60, 50, 40, or 30 or fewer amino acids. In other embodiments, the peptide comprises 20 or fewer amino acids. In other embodiments the peptide comprises no more than 20, 15, 10, or 5 peptides subsequent to Cys$_{18}$. In certain embodiments Xaa$_{19}$ is a chymotrypsin or trypsin cleavage site and an analgesic peptide is present immediately following Xaa$_{19}$.

In a third aspect, the invention features a method for treating a patient suffering from constipation. Clinically accepted criteria that define constipation range from the frequency of bowel movements, the consistency of feces and the ease of bowel movement. One common definition of constipation is less than three bowel movements per week. Other definitions include abnormally hard stools or defecation that requires excessive straining (Schiller 2001, Aliment Pharmacol Ther 15:749-763). Constipation may be idiopathic (functional constipation or slow transit constipation) or secondary to other causes including neurologic, metabolic or endocrine disorders. These disorders include diabetes mellitus, hypothyroidism, hyperthyroidism, hypocalcemia, Multiple Sclerosis, Parkinson's disease, spinal cord lesions, Neurofibromatosis, autonomic neuropathy, Chagas disease, Hirschsprung's disease and Cystic fibrosis. Constipation may also be the result of surgery (postoperative ileus) or due to the use of drugs such as analgesics (like opiods), antihypertensives, anticonvulsants, antidepressants, antispasmodics and antipsychotics.

The method comprising administering a composition comprising a purified polypeptide comprising the amino acid sequence (I): Xaa$_1$ Xaa$_2$ Xaa$_3$ Xaa$_4$ Xaa$_5$ Cys$_6$ Cys$_7$ Xaa$_8$ Xaa$_9$Cys$_{10}$ Cys$_{11}$ Xaa$_{12}$ Xaa$_{13}$ Xaa$_{14}$ Cys$_{15}$ Xaa$_{16}$ Xaa$_{17}$ Cys$_{18}$ Xaa$_{19}$ Xaa$_{20}$ Xaa$_{21}$ (SEQ ID NO:120 wherein: Xaa$_1$ Xaa$_2$ Xaa$_3$ Xaa$_4$ Xaa$_5$ is Asn, Ser Ser Asn Tyr (SEQ ID NO:121) or is missing or Xaa$_1$ Xaa$_2$ Xaa$_3$ Xaa$_4$ is missing and Xaa$_5$ is Asn, Trp, Tyr, Asp, Ile, Thr, or Phe; Xaa$_8$ is Glu, Asp, Gln, Gly or Pro; Xaa$_9$ is Leu, Ile, Val, Ala, Lys, Arg, Trp, Tyr or Phe; Xaa$_{12}$ is Asn, Tyr, Asp or Ala; Xaa$_{13}$ is Pro or Gly; Xaa$_{14}$ is Ala, Leu, Ser, Gly, Val, Glu, Gln, Ile, Leu, Lys, Arg, and Asp; Xaa$_{16}$ is Thr, Ala, Asn, Lys, Arg, Trp; Xaa$_{17}$ is Gly, Pro or Ala; Xaa$_{19}$ is Trp, Tyr, Phe or Leu; Xaa$_{19}$ is Lys or Arg; Xaa$_{20}$ Xaa$_{21}$ is AspPhe, or is missing or Xaa$_{20}$ is Asn or Glu and Xaa$_{21}$ is missing or Xaa$_{19}$ Xaa$_{20}$ Xaa$_{21}$ is missing.

In one embodiment of the method, the peptide comprises the amino acid sequence (I): Xaa$_1$ Xaa$_2$ Xaa$_3$ Xaa$_4$ Xaa$_5$ Cys$_6$ Cys$_7$ Xaa$_8$ Xaa$_9$ Cys$_{10}$ Cys$_{11}$ Xaa$_{12}$ Xaa$_{13}$ Xaa$_{14}$ Cys$_{15}$ Xaa$_{16}$ Xaa$_{17}$ Cys$_{18}$ Xaa$_{19}$ Xaa$_{20}$ Xaa$_{21}$ (SEQ ID NO:119) wherein: Xaa$_1$ Xaa$_2$ Xaa$_3$ Xaa$_4$ Xaa$_5$ is missing; Xaa$_8$ is Glu; Xaa$_9$ is Leu, Ile, Lys, Arg, Trp, Tyr or Phe; Xaa$_{12}$ is Asn; Xaa$_{13}$ is Pro; Xaa$_{14}$ is Ala; Xaa$_{16}$ is Thr, Ala, Lys, Arg, Trp; Xaa$_{17}$ is Gly; Xaa$_{19}$ is Tyr or Leu; Xaa$_{19}$ is Lys or Arg; Xaa$_{20}$ Xaa$_{21}$ is AspPhe or is missing.

In various preferred embodiments, the constipation is associated with use of a therapeutic agent; the constipation is associated with a neuropathic disorder; the constipation is post-surgical constipation (postoperative ileus); and the constipation associated with a gastrointestinal disorder; the constipation is idiopathic (functional constipation or slow transit constipation); the constipation is associated with neuropathic, metabolic or endocrine disorder (e.g., diabetes mellitus, hypothyroidism, hyperthyroidism, hypocalcemia, Multiple Sclerosis, Parkinson's disease, spinal cord lesions, neurofibromatosis, autonomic neuropathy, Chagas disease, Hirschsprung's disease or cystic fibrosis). Constipation may also be the result of surgery (postoperative ileus) or due to the use of drugs such as analgesics (e.g., opiods), antihypertensives, anticonvulsants, antidepressants, antispasmodics and antipsychotics.

In a fourth aspect, the invention features a method for treating a patient suffering a gastrointestinal disorder, the method comprising administering to the patient a composition comprising a purified polypeptide comprising the amino acid sequence (I): Xaa$_1$ Xaa$_2$ Xaa$_3$ Xaa$_4$ Xaa$_5$ Cys$_6$ Cys$_7$ Xaa$_8$ Xaa$_9$ Cys$_{10}$ Cys$_{11}$ Xaa$_{12}$ Xaa$_{13}$ Xaa$_{14}$ Cys$_{15}$ Xaa$_{16}$ Xaa$_{17}$ Cys$_{18}$ Xaa$_{19}$ Xaa$_{20}$ Xaa$_{21}$ (SEQ ID NO:120) wherein: Xaa$_1$ Xaa$_2$ Xaa$_3$ Xaa$_4$ Xaa$_5$ is Asn Ser Ser Asn Tyr (SEQ ID NO:121) or is missing or Xaa$_1$ Xaa$_2$ Xaa$_3$ Xaa$_4$ is missing and Xaa$_5$ is Asn, Trp, Tyr, Asp, Ile, Thr, or Phe; Xaa$_8$ is Glu, Asp, Gln, Gly or Pro; Xaa$_9$ is Leu, Ile, Val, Ala, Lys, Arg, Trp, Tyr or Phe; Xaa$_{12}$ is Asn, Tyr, Asp or Ala; Xaa$_{13}$ is Pro or Gly; Xaa$_{14}$ is Ala, Leu, Ser, Gly, Val, Glu, Gln, Ile, Leu, Lys, Arg, and Asp; Xaa$_{16}$ is Thr, Ala, Asn, Lys, Arg, Trp; Xaa$_{17}$ is Gly, Pro or Ala; Xaa$_{19}$ is Trp, Tyr, Phe or Leu; Xaa$_{19}$ is Lys or Arg; Xaa$_{20}$ Xaa$_{21}$ is AspPhe or is missing or Xaa$_{20}$ is Asn or Glu and Xaa$_{21}$ is missing or Xaa$_{19}$ Xaa$_{20}$ Xaa$_{21}$ is missing.

In one embodiment of the method, the peptide comprises the amino acid sequence (I): Xaa$_1$ Xaa$_2$ Xaa$_3$ Xaa$_4$ Xaa$_5$ Cys$_6$ Cys$_7$ Xaa$_8$ Xaa$_9$ Cys$_{10}$ Cys$_{11}$ Xaa$_{12}$ Xaa$_{13}$ Xaa$_{14}$ Cys$_{15}$ Xaa$_{16}$ Xaa$_{17}$ Cys$_{18}$ Xaa$_{19}$ Xaa$_{20}$ Xaa$_{21}$ (SEQ ID NO:[126]119) wherein: Xaa$_1$ Xaa$_2$ Xaa$_3$ Xaa$_4$ Xaa$_5$ is missing; Xaa$_8$ is Glu; Xaa$_9$ is Leu, Ile, Lys, Arg, Trp, Tyr or Phe; Xaa$_{12}$ is Asn; Xaa$_{13}$ is Pro; Xaa$_{14}$ is Ala; Xaa$_{16}$ is Thr, Ala, Lys, Arg, Trp; Xaa$_{17}$ is Gly; Xaa$_{19}$ is Tyr or Leu; Xaa$_{19}$ is Lys or Arg; Xaa$_{20}$ Xaa$_{21}$ is AspPhe or is missing.

In various embodiments, the patient is suffering from a gastrointestinal disorder; the patient is suffering from a disorder selected from the group consisting of a gastrointestinal motility disorder, irritable bowel syndrome, chronic constipation, a functional gastrointestinal disorder, gastroesophageal reflux disease, functional heartburn, dyspepsia, functional dyspepsia, nonulcer dyspepsia, gastroparesis, chronic intestinal pseudo-obstruction, Crohn's disease, ulcerative colitis, Inflammatory bowel disease, colonic pseudo-obstruction, obesity, congestive heart failure, or benign prostatic hyperplasia.

In various preferred embodiments, Xaa$_9$ is Leu, Ile or Val and Xaa$_{16}$ is Trp, Tyr or Phe; Xaa$_9$ is Trp, Tyr or Phe and Xaa$_{16}$ is Thr or Ala; Xaa$_{19}$ is Trp, Tyr, Phe; Xaa$_{19}$ is Lys or Arg; Xaa$_{20}$ Xaa$_{21}$ is AspPhe; Xaa$_1$ Xaa$_2$ Xaa$_3$ Xaa$_4$ is missing and Xaa$_5$ is Asn.

In a fifth aspect, the invention features a method for increasing gastrointestinal motility in a patient, the method comprising: administering to the patients a composition comprising a purified polypeptide comprising the amino acid sequence (I): Xaa$_1$ Xaa$_2$ Xaa$_3$ Xaa$_4$ Xaa$_5$ Cys$_6$ Cys$_7$ Xaa$_8$ Xaa$_9$ Cys$_{10}$ Cys$_{11}$ Xaa$_{12}$ Xaa$_{13}$ Xaa$_{14}$ Cys$_{15}$ Xaa$_{16}$ Xaa$_{17}$ Cys$_{18}$ Xaa$_{19}$ Xaa$_{20}$ Xaa$_{21}$ (SEQ ID NO:120) wherein: Xaa$_1$ Xaa$_2$ Xaa$_3$ Xaa$_4$ Xaa$_5$ is Asn Ser Ser Asn Tyr (SEQ ID NO:121) or is missing or Xaa$_1$ Xaa$_2$ Xaa$_3$ Xaa$_4$ is missing and Xaa$_5$ is Asn, Trp, Tyr, Asp, Ile, Thr, or Phe; Xaa$_8$ is Glu, Asp, Gln, Gly or Pro; Xaa$_9$ is Leu, Ile, Val, Ala, Lys, Arg, Trp, Tyr or Phe; Xaa$_{12}$ is Asn, Tyr, Asp or Ala; Xaa$_{13}$ is Pro or Gly; Xaa$_{14}$ is Ala, Leu, Ser, Gly, Val, Glu, Gln, Ile, Leu, Lys, Arg, and Asp; Xaa$_{16}$ is Thr, Ala, Asn, Lys, Arg, Trp; Xaa$_{17}$ is Gly, Pro or Ala; Xaa$_{19}$ is Trp, Tyr, Phe or Leu; Xaa$_{19}$ is Lys or Arg; Xaa$_{20}$ Xaa$_{21}$ is AspPhe or is missing or Xaa$_{20}$ is Asn or Glu and Xaa$_{21}$ is missing or Xaa$_{19}$ Xaa$_{20}$ Xaa$_{21}$ is missing.

In one embodiment the peptide comprises the amino acid sequence (I): Xaa$_1$ Xaa$_2$ Xaa$_3$ Xaa$_4$ Xaa$_5$ Cys$_6$ Cys$_7$ Xaa$_8$ Xaa$_9$ Cys$_{10}$ Cys$_{11}$ Xaa$_{12}$ Xaa$_{13}$ Xaa$_{14}$ Cys$_{15}$ Xaa$_{16}$ Xaa$_{17}$ Cys$_{18}$ Xaa$_{19}$ Xaa$_{20}$ Xaa$_{21}$ (SEQ ID NO:119) wherein: Xaa$_1$ Xaa$_2$ Xaa$_3$ Xaa$_4$ Xaa$_5$ is missing; Xaa$_8$ is Glu; Xaa$_9$ is Leu, Ile, Lys, Arg, Trp, Tyr or Phe; Xaa$_{12}$ is Asn; Xaa$_{13}$ is Pro; Xaa$_{14}$ is Ala; Xaa$_{16}$ is Thr, Ala, Lys, Arg, Trp; Xaa$_{17}$ is Gly; Xaa$_{19}$ is Tyr or Leu; Xaa$_{19}$ is Lys or Arg; Xaa$_{20}$ Xaa$_{21}$ is AspPhe or is missing.

In a sixth aspect, the invention features a method for increasing the activity of an intestinal guanylate cyclase (GC-C) receptor in a patient, the method comprising: administering to the patient a composition comprising a purified polypeptide comprising the amino acid sequence (I): Xaa$_1$ Xaa$_2$ Xaa$_3$ Xaa$_4$ Xaa$_5$ Cys$_6$ Cys$_7$ Xaa$_8$ Xaa$_9$ Cys$_{10}$ Cys$_{11}$ Xaa$_{12}$ Xaa$_{13}$ Xaa$_{14}$ Cys$_{15}$ Xaa$_{16}$ Xaa$_{17}$ Cys$_{18}$ Xaa$_{19}$ Xaa$_{20}$ Xaa$_{21}$ (SEQ ID NO:120) wherein: Xaa$_1$ Xaa$_2$ Xaa$_3$ Xaa$_4$ Xaa$_5$ is Asn Ser Ser Asn Tyr (SEQ ID NO:121) or is missing or Xaa$_1$ Xaa$_2$ Xaa$_3$ Xaa$_4$ is missing and Xaa$_5$ is Asn, Trp, Tyr, Asp, Ile, Thr, or Phe; Xaa$_8$ is Glu, Asp, Gln, Gly or Pro; Xaa$_9$ is Leu, Ile, Val, Ala, Lys, Arg, Trp, Tyr or Phe; Xaa$_{12}$ is Asn, Tyr, Asp or Ala; Xaa$_{13}$ is Pro or Gly; Xaa$_{14}$ is Ala, Leu, Ser, Gly, Val, Glu, Gln, Ile, Leu, Lys, Arg, and Asp; Xaa$_{16}$ is Thr, Ala, Asn, Lys, Arg, Trp; Xaa$_{17}$ is Gly, Pro or Ala; Xaa$_{19}$ is Trp, Tyr, Phe or Leu; Xaa$_{19}$ is Lys or Arg; Xaa$_{20}$ Xaa$_{21}$ is AspPhe or is missing or Xaa$_{20}$ is Asn or Glu and Xaa$_{21}$ is missing or Xaa$_{19}$ Xaa$_{20}$ Xaa$_{21}$ is missing.

In one embodiment the peptide comprises the amino acid sequence (I): Xaa$_1$ Xaa$_2$ Xaa$_3$ Xaa$_4$ Xaa$_5$ Cys$_6$ Cys$_7$ Xaa$_8$ Xaa$_9$ Cys$_{10}$ Cys$_{11}$ Xaa$_{12}$ Xaa$_{13}$ Xaa$_{14}$ Cys$_{15}$ Xaa$_{16}$ Xaa$_{17}$ Cys$_{18}$ Xaa$_{19}$ Xaa$_{20}$ Xaa$_{21}$ (SEQ ID NO:[[126]]119) wherein: Xaa$_1$ Xaa$_2$ Xaa$_3$ Xaa$_4$ Xaa$_5$ is missing, Xaa$_8$ is Glu; Xaa$_9$ is Leu, Ile, Lys, Arg, Trp, Tyr, or Phe; Xaa$_{12}$ is Asn; Xaa$_{13}$ is Pro; Xaa$_{14}$ is Ala; Xaa$_{16}$ is Thr, Ala, Lys, Arg, Trp; Xaa$_{17}$ is Gly; Xaa$_{19}$ is Tyr or Leu; Xaa$_{19}$ is Lys or Arg; Xaa$_{20}$ Xaa$_{21}$ is AspPhe or is missing.

In a seventh aspect, the invention features an isolated nucleic acid molecule comprising a nucleotide sequence encoding a polypeptide comprising the amino acid sequence: (I): Xaa$_1$ Xaa$_2$ Xaa$_3$ Xaa$_4$ Xaa$_5$ Cys$_6$ Cys$_7$ Xaa$_8$ Xaa$_9$ Cys$_{10}$ Cys$_{11}$ Xaa$_{12}$ Xaa$_{13}$ Xaa$_{14}$ Cys$_{15}$ Xaa$_{16}$ Xaa$_{17}$ Cys$_{18}$ Xaa$_{19}$ Xaa$_{20}$ Xaa$_{21}$ (SEQ ID NO:120) wherein: Xaa$_1$ Xaa$_2$ Xaa$_3$ $Xaa_4 Xaa_5$ is Asn Ser Ser Asn Tyr (SEQ ID NO:121) or is missing or $Xaa_1 Xaa_2 Xaa_3 Xaa_4$ is missing and $Xaa_5$ is Asn, Trp, Tyr, Asp, Ile, Thr, or Phe; $Xaa_8$ is Glu, Asp, Gln, Gly or Pro; $Xaa_9$ is Leu, Ile, Val, Ala, Lys, Arg, Trp, Tyr or Phe; $Xaa_{12}$ is Asn, Tyr, Asp or Ala; $Xaa_{13}$ is Pro or Gly; $Xaa_{14}$ is Ala, Leu, Ser, Gly, Val, Glu, Gln, Ile, Leu, Lys, Arg, and Asp; $Xaa_{16}$ is Thr, Ala, Asn, Lys, Arg, Trp; $Xaa_{17}$ is Gly, Pro or Ala; $Xaa_{19}$ is Trp, Tyr, Phe or Leu; $Xaa_{19}$ is Lys or Arg; $Xaa_{20} Xaa_{21}$ is AspPhe or is missing or $Xaa_{20}$ is Asn or Glu and $Xaa_{21}$ is missing or $Xaa_{19} Xaa_{20} Xaa_{21}$ is missing.

In one embodiment the peptide comprises the amino acid sequence (I): $Xaa_1 Xaa_2 Xaa_3 Xaa_4 Xaa_5 Cys_6 Cys_7 Xaa_8 Xaa_9 Cys_{10} Cys_{11} Xaa_{12} Xaa_{13} Xaa_{14} Cys_{15} Xaa_{16} Xaa_{17} Cys_{18} Xaa_{19} Xaa_{20} Xaa_{21}$ (SEQ ID NO:119) wherein: $Xaa_1 Xaa_2 Xaa_3 Xaa_4 Xaa_5$ is missing; $Xaa_8$ is Glu; $Xaa_9$ is Leu, Ile, Lys, Arg, Trp, Tyr or Phe; $Xaa_{12}$ is Asn; $Xaa_{13}$ is Pro; $Xaa_{14}$ is Ala; $Xaa_{16}$ is Thr, Ala, Lys, Arg, Trp; $Xaa_{17}$ is Gly; $Xaa_{19}$ is Tyr or Leu; $Xaa_{19}$ is Lys or Arg; $Xaa_{20} Xaa_{21}$ is AspPhe or is missing.

In an eighth aspect the invention features a method for treating constipation, the method comprising administering an agonist of the intestinal guanylate cyclase (GC-C) receptor. In various embodiments: the agonist is a peptide, the peptide includes four Cys that form two disulfide bonds, and the peptide includes six Cys that foam three disulfide bonds.

In a ninth aspect, the invention features a method for treating a gastrointestinal disorder, a gastrointestinal motility disorder, irritable bowel syndrome, chronic constipation, a functional gastrointestinal disorder, gastroesophageal reflux disease, functional heartburn, dyspepsia, functional dyspepsia, nonulcer dyspepsia, gastroparesis, chronic intestinal pseudo-obstruction, colonic pseudo-obstruction, Crohn's disease, ulcerative colitis, Inflammatory bowel disease, obesity, congestive heart failure, or benign prostatic hyperplasia, the method comprising administering antagonist of the intestinal guanylate cyclase (GC-C) receptor either orally, by rectal suppository, or parenterally. In various embodiments: the agonist is a peptide, the peptide includes four Cys that form two disulfide bonds, and the peptide includes six Cys that form three disulfide bonds.

In a tenth aspect, the invention features a method for treating a gastrointestinal disorder selected from the group consisting of: a gastrointestinal motility disorder, irritable bowel syndrome, chronic constipation, a functional gastrointestinal disorder, gastroesophageal reflux disease, functional heartburn, dyspepsia, functional dyspepsia, nonulcer dyspepsia, gastroparesis, chronic intestinal pseudo-obstruction, colonic pseudo-obstruction, Crohn's disease, ulcerative colitis, Inflammatory bowel disease, the method comprising administering an agonist of the intestinal guanylate cyclase (GC-C) receptor. In various embodiments the composition is administered orally; the peptide comprises 30 or fewer amino acids, the peptide comprises 20 or fewer amino acids, and the peptide comprises no more than 5 amino acids prior to $Cys_5$.

In various embodiments: the agonist is a peptide, the peptide includes four Cys that form two disulfide bonds, and the peptide includes six Cys that form three disulfide bonds.

In an eleventh aspect, the invention features a method for treating obesity, the method comprising administering an agonist of the intestinal guanylate cyclase (GC-C) receptor. In various embodiments: the agonist is, a peptide, the peptide includes four Cys that form two disulfide bonds, and the peptide includes six Cys that form three disulfide bonds.

In a twelfth aspect, the invention features a method for treating obesity, the method comprising administering a polypeptide comprising the amino acid sequence: (I): $Xaa_1 Xaa_2 Xaa_3 Xaa_4 Xaa_5 Cys_6 Cys_7 Xaa_8 Xaa_9 Cys_{10} Cys_{11} Xaa_{12} Xaa_{13} Xaa_{14} Cys_{15} Xaa_{16} Xaa_{17} Cys_{18} Xaa_{19} Xaa_{20} Xaa_{21}$ (SEQ ID NO:120) wherein: $Xaa_1 Xaa_2 Xaa_3 Xaa_4 Xaa_5$, is Asn Ser Ser Asn Tyr (SEQ ID NO:121) or is missing or $Xaa_1 Xaa_2 Xaa_3 Xaa_4$ is missing and $Xaa_5$ is Asn, Trp, Tyr, Asp, Ile, Thr, or Phe; $Xaa_8$ is Glu, Asp, Gln, Gly or Pro; $Xaa_9$ is Leu, Ile, Val, Ala, Lys, Arg, Trp, Tyr or Phe; $Xaa_{12}$ is Asn, Tyr, Asp or Ala; $Xaa_{13}$ is Pro or Gly; $Xaa_{14}$ is Ala, Leu, Ser, Gly, Val, Glu, Gln, Ile, Leu, Lys, Arg, and Asp; $Xaa_{16}$ is Thr, Ala, Asn, Lys, Arg, Trp; $Xaa_{17}$ is Gly, Pro or Ala; $Xaa_{19}$ is Trp, Tyr, Phe or Leu; and $Xaa_{20} Xaa_{21}$ is AspPhe or is missing or $Xaa_{20}$ is Asn or Glu and $Xaa_{21}$ is missing or $Xaa_{19} Xaa_{20} Xaa_{21}$ is missing. The peptide can be administered alone or in combination with another agent for the treatment of obesity, e.g., sibutramine or another agent, e.g., an agent described herein.

In one embodiment the peptide comprises the amino acid sequence (I): $Xaa_1 Xaa_2 Xaa_3 Xaa_4 Xaa_5 Cys_6 Cys_7 Xaa_8 Xaa_9 Cys_{10} Cys_{11} Xaa_{12} Xaa_{13} Xaa_{14} Cys_{15} Xaa_{16} Xaa_{17} Cys_{18} Xaa_{19} Xaa_{20} Xaa_{21}$ (SEQ ID NO:119) wherein: $Xaa_1 Xaa_2 Xaa_3 Xaa_4 Xaa_5$ is missing; $Xaa_{18}$ is Glu; $Xaa_9$ is Leu, Ile, Lys, Arg, Trp, Tyr or Phe; $Xaa_{12}$ is Asn; $Xaa_{13}$ is Pro; $Xaa_{14}$ is Ala; $Xaa_{16}$ is Thr, Ala, Lys, Arg, Trp; $Xaa_{17}$ is Gly; $Xaa_{19}$ is Tyr or Leu; and $Xaa_{20} Xaa_{21}$ is AspPhe or is missing.

In a thirteenth aspect, the invention features a pharmaceutical composition comprising a polypeptide described herein.

In a fourteenth aspect, the invention features a method for treating congestive heart failure, the method comprising: administering to the patient a composition comprising a purified polypeptide comprising the amino acid sequence (I): $Xaa_1 Xaa_2 Xaa_3 Xaa_4 Xaa_5 Cys_6 Cys_7 Xaa_8 Xaa_9 Cys_{10} Cys_{11} Xaa_{12} Xaa_{13} Xaa_{14} Cys_{15} Xaa_{16} Xaa_{17} Cys_{18} Xaa_{19} Xaa_{20} Xaa_{21}$ (SEQ ID NO:120) wherein: $Xaa_1 Xaa_2 Xaa_3 Xaa_4 Xaa_5$ is Asn Ser Ser Asn Tyr (SEQ ID NO:121) or is missing or $Xaa_1 Xaa_2 Xaa_3 Xaa_4$ is missing and $Xaa_5$ is Asn, Trp, Tyr, Asp, Ile, Thr, or Phe; $Xaa_8$ is Glu, Asp, Gln, Gly or Pro; $Xaa_9$ is Leu, Ile, Val, Ala, Lys, Arg, Trp, Tyr or Phe; $Xaa_{12}$ is Asn, Tyr, Asp or Ala; $Xaa_{13}$ is Pro or Gly; $Xaa_{14}$ is Ala, Leu, Ser, Gly, Val, Glu, Gln, Ile, Leu, Lys, Arg, and Asp; $Xaa_{16}$ is Thr, Ala, Asn, Lys, Arg, Trp; $Xaa_{17}$ is Gly, Pro or Ala; $Xaa_{19}$ is Trp, Tyr, Phe or Leu; and $Xaa_{20} Xaa_{21}$ is AspPhe or is missing or $Xaa_{20}$ is Asn or Glu and $Xaa_{21}$ is missing or $Xaa_{19} Xaa_{20} Xaa_{21}$ is missing. The peptide can be administered in combination with another agent for treatment of congestive heart failure, for example, a natriuretic peptide such as atrial natriuretic peptide, brain natriuretic peptide or C-type natriuretic peptide), a diuretic, or an inhibitor of angiotensin converting enzyme.

In one embodiment the peptide comprises the amino acid sequence (I):—$Xaa_1 Xaa_2 Xaa_3 Xaa_4 Xaa_5 Cys_6 Cys_7 Xaa_8 Xaa_9 Cys_{10} Cys_{11} Xaa_{12} Xaa_{13} Xaa_{14} Cys_{15} Xaa_{16} Xaa_{17} Cys_{18} Xaa_{19} Xaa_{20} Xaa_{21}$ (SEQ ID No:119) wherein: $Xaa_1 Xaa_2 Xaa_3 Xaa_4 Xaa_5$ is missing; $Xaa_8$ is Glu; $Xaa_9$ is Leu, Ile, Lys, Arg, Trp, Tyr or Phe; $Xaa_{12}$ is Asn; $Xaa_{13}$ is Pro; $Xaa_{14}$ is Ala; $Xaa_{16}$ is Thr, Ala, Lys, Arg, Trp; $Xaa_{17}$ is Gly; $Xaa_{19}$ is Tyr or Leu; $Xaa_{19}$ is Lys or Arg; $Xaa_{20} Xaa_{21}$ is AspPhe or is missing.

In a fifteenth aspect, the invention features a method for treating benign prostatic hyperplasia, the method comprising: administering to the patient a composition comprising a purified polypeptide comprising the amino acid sequence (I): $Xaa_1 Xaa_2 Xaa_3 Xaa_4 Xaa_5 Cys_6 Cys_7 Xaa_8 Xaa_9 Cys_{10} Cys_{11} Xaa_{12} Xaa_{13} Xaa_{14} Cys_{15} Xaa_{16} Xaa_{17} Cys_{18} Xaa_{19} Xaa_{20} Xaa_{21}$ (SEQ ID No:120) wherein: $Xaa_1 Xaa_2 Xaa_3 Xaa_4 Xaa_5$ is Asn Ser Ser Asn Tyr (SEQ ID NO:127) or is missing or $Xaa_1 Xaa_2 Xaa_3 Xaa_4$ is missing and $Xaa_5$ is Asn, Trp, Tyr, Asp, Ile, Thr, or Phe; $Xaa_8$ is Glu, Asp, Gln, Gly or Pro; $Xaa_9$ is Leu, Ile, Val, Ala, Lys, Arg, Trp, Tyr or Phe; $Xaa_{12}$ is Asn, Tyr, Asp or Ala; $Xaa_{13}$ is Pro or Gly; $Xaa_{14}$ is Ala, Leu, Ser, Gly, Val, Glu, Gln, Ile, Leu, Lys, Arg, and Asp; Xaa$_{16}$ is Thr, Ala, Asn, Lys, Arg, Trp; Xaa$_{17}$ is Gly, Pro or Ala; Xaa$_{19}$ is Trp, Tyr, Phe or Leu; Xaa$_{19}$ is Lys or Arg; Xaa$_{20}$ Xaa$_{21}$ is AspPhe or is missing or Xaa$_{20}$ is Asn or Glu and Xaa$_{21}$ is missing or Xaa$_{19}$ Xaa$_{20}$ Xaa$_{21}$ is missing.

The peptide can be administered in combination with another agent for treatment of BPH, for example, a 5-alpha reductase inhibitor (e.g., finasteride) or an alpha adrenergic inhibitor (e.g., doxazosine).

In one embodiment the peptide comprises the amino acid sequence (I): Xaa$_1$ Xaa$_2$ Xaa$_3$ Xaa$_4$ Xaa$_5$ Cys$_6$ Cys$_7$ Xaa$_8$ Xaa$_9$ Cys$_{10}$ Cys$_{11}$ Xaa$_{12}$ Xaa$_{13}$ Xaa$_{14}$ Cys$_{15}$ Xaa$_{16}$ Xaa$_{17}$ Cys$_{18}$ Xaa$_{19}$ Xaa$_{20}$ Xaa$_{21}$ (SEQ ID NO:119) wherein: Xaa$_1$ Xaa$_2$ Xaa$_3$ Xaa$_4$ Xaa$_5$ is missing; Xaa$_8$ is Glu; Xaa$_9$ is Leu, Ile, Lys, Arg, Trp, Tyr or Phe; Xaa$_{12}$ is Asn; Xaa$_{13}$ is Pro; Xaa$_{14}$ is Ala; Xaa$_{16}$ is Thr, Ala, Lys, Arg, Trp; Xaa$_{17}$ is Gly; Xaa$_{19}$ is Tyr or Leu; and Xaa$_{20}$ Xaa$_{21}$ is AspPhe or is missing.

In a sixteenth aspect, the invention features a method for treating or reducing pain, including visceral pain, pain associated with a gastrointestinal disorder or pain associated with some other disorder, the method comprising: administering to a patient a composition comprising a purified polypeptide comprising the amino acid sequence (I): Xaa$_1$ Xaa$_2$ Xaa$_3$ Xaa$_4$ Xaa$_5$ Cys$_6$ Cys$_7$ Xaa$_8$ Xaa$_9$ Cys$_{10}$ Cys$_{11}$ Xaa$_{12}$ Xaa$_{13}$ Xaa$_{14}$ Cys$_{15}$ Xaa$_{16}$ Xaa$_{17}$ Cys$_{18}$ Xaa$_{19}$ Xaa$_{20}$ Xaa$_{21}$ (SEQ ID No:119), e.g., a purified polypeptide comprising amino acid sequence disclosed herein.

In a seventeenth aspect, the invention features a method for treating inflammation, including inflammation of the gastrointestinal tract, e.g., inflammation associated with a gastrointestinal disorder or infection or some other disorder, the method comprising: administering to a patient a composition comprising a purified polypeptide comprising the amino acid sequence (I): Xaa$_1$ Xaa$_2$ Xaa$_3$ Xaa$_4$ Xaa$_5$ Cys$_6$ Cys$_7$ Xaa$_8$ Xaa$_9$ Cys$_{10}$ Cys$_{11}$ Xaa$_{12}$ Xaa$_{13}$ Xaa$_{14}$ Cys$_{15}$ Xaa$_{16}$ Xaa$_{17}$ Cys$_{18}$ Xaa$_{19}$ Xaa$_{20}$ Xaa$_{21}$ (SEQ ID No:119), e.g., a purified polypeptide comprising an amino acid sequence disclosed herein.

In certain embodiments the peptide includes a peptide comprising or consisting of the amino acid sequence Xaa$_1$ Xaa$_2$ Xaa$_3$ Xaa$_4$ Xaa$_5$ Cys Cys Glu Xaa$_9$ Cys Cys Asn Pro Ala Cys Thr Gly Cys Tyr Xaa$_{20}$ Xaa$_{21}$ (II) (SEQ ID NO:66) wherein Xaa$_9$ is any amino acid, wherein Xaa$_9$ is any amino acid other than Leu, wherein Xaa$_9$ is selected from Phe, Trp and Tyr; wherein Xaa$_9$ is selected from any other natural or non-natural aromatic amino acid, wherein Xaa$_9$ is Tyr; wherein Xaa$_1$ Xaa$_2$ Xaa$_3$ Xaa$_4$ Xaa$_5$ is Asn Ser Ser Asn Tyr (SEQ ID NO:121); wherein Xaa$_1$ Xaa$_2$ Xaa$_3$ Xaa$_4$, and Xaa$_5$ are missing; wherein Xaa$_1$ Xaa$_2$ Xaa$_3$ and Xaa$_4$ are missing; wherein Xaa$_1$ Xaa$_2$ and Xaa$_3$ are missing; wherein Xaa$_1$ and Xaa$_2$ are missing; wherein Xaa$_1$ is missing; wherein Xaa$_{20}$ Xaa$_{21}$ is AspPhe or is missing or Xaa$_{20}$ is Asn or Glu and Xaa$_{21}$ is missing or Xaa$_{19}$ Xaa$_{20}$ Xaa$_{21}$ is missing. In the case of a peptide comprising the sequence (I): Xaa$_1$ Xaa$_2$ Xaa$_3$ Xaa$_4$ Xaa$_5$ Cys$_6$ Cys$_7$ Xaa$_8$ Xaa$_9$ Cys$_{10}$ Cys$_{11}$ Xaa$_{12}$ Xaa$_{13}$ Xaa$_{14}$ Cys$_{15}$ Xaa$_{16}$ Xaa$_{17}$ Cys$_{18}$ Xaa$_{19}$ Xaa$_{20}$ Xaa$_{21}$ (SEQ ID No:119) wherein: Xaa$_1$ Xaa$_2$ Xaa$_3$ Xaa$_4$ Xaa$_5$ is missing and/or the sequence Xaa$_{19}$ Xaa$_{20}$ Xaa$_{21}$ is missing peptide can still contain additional carboxyterminal or amino terminal amino acids or both Among the useful peptides are peptides comprising, consisting of or consisting essentially of the amino acid sequence Xaa$_1$ Xaa$_2$ Xaa$_3$ Xaa$_4$ Xaa$_5$ Cys Cys Glu Xaa$_9$ Cys Cys Asn Pro Ala Cys Thr Gly Cys Tyr Xaa$_{20}$ Xaa$_{21}$ (II) (SEQ ID NO:66) are the following peptides.

```
                                                  (SEQ ID NO:67)
Gln Ser Ser Asn Tyr Cys Cys Glu Tyr Cys Cys Asn
Pro Ala Cys Thr Gly Cys Tyr (SEQ ID NO:68)
Asn Thr Ser Asn Tyr Cys Cys Glu Tyr Cys Cys Asn
Pro Ala Cys Thr Gly Cys Tyr (SEQ ID NO:69)
Asn Leu Ser Asn Tyr Cys Cys Glu Tyr Cys Cys Asn
Pro Ala Cys Thr Gly Cys Tyr (SEQ ID NO:70)
Asn Ile Ser Asn Tyr Cys Cys Glu Tyr Cys Cys Asn
Pro Ala Cys Thr Gly Cys Tyr (SEQ ID NO:71)
Asn Ser Ser Gln Tyr Cys Cys Glu Tyr Cys Cys Asn
Pro Ala Cys Thr Gly Cys Tyr (SEQ ID NO:72)
Ser Ser Asn Tyr Cys Cys Glu Tyr Cys Cys Asn Pro
Ala Cys Thr Gly Cys Tyr (SEQ ID NO:73)
Gln Ser Ser Gln Tyr Cys Cys Glu Tyr Cys Cys Asn
Pro Ala Cys Thr Gly Cys Tyr (SEQ ID NO:74)
Ser Ser Gln Tyr Cys Cys Glu Tyr Cys Cys Asn Pro
Ala Cys Thr Gly Cys Tyr (SEQ ID NO:75)
Asn Ser Ser Asn Tyr Cys Cys Glu Ala Cys Cys Asn
Pro Ala Cys Thr Gly Cys Tyr (SEQ ID NO:76)
Asn Ser Ser Asn Tyr Cys Cys Glu Arg Cys Cys Asn
Pro Ala Cys Thr Gly Cys Tyr (SEQ ID NO:77)
Asn Ser Ser Asn Tyr Cys Cys Glu Asn Cys Cys Asn
Pro Ala Cys Thr Gly Cys Tyr (SEQ ID NO:78)
Asn Ser Ser Asn Tyr Cys Cys Glu Asp Cys Cys Asn
Pro Ala Cys Thr Gly Cys Tyr (SEQ ID NO:79)
Asn Ser Ser Asn Tyr Cys Cys Glu Cys Cys Cys Asn
Pro Ala Cys Thr Gly Cys Tyr (SEQ ID NO:80)
Asn Ser Ser Asn Tyr Cys Cys Glu Gln Cys Cys Asn
Pro Ala Cys Thr Gly Cys Tyr (SEQ ID NO:81)
Asn Ser Ser Asn Tyr Cys Cys Glu Glu Cys Cys Asn
Pro Ala Cys Thr Gly Cys Tyr (SEQ ID NO:82)
Asn Ser Ser Asn Tyr Cys Cys Glu Gly Cys Cys Asn
Pro Ala Cys Thr Gly Cys Tyr
```

(SEQ ID NO:83)
Asn Ser Ser Asn Tyr Cys Cys Glu His Cys Cys Asn
Pro Ala Cys Thr Gly Cys Tyr (SEQ ID NO:84)
Asn Ser Ser Asn Tyr Cys Cys Glu Ile Cys Cys Asn
Pro Ala Cys Thr Gly Cys Tyr (SEQ ID NO:85)
Asn Ser Ser Asn Tyr Cys Cys Glu Lys Cys Cys Asn
Pro Ala Cys Thr Gly Cys Tyr (SEQ ID NO:86)
Asn Ser Ser Asn Tyr Cys Cys Glu Met Cys Cys Asn
Pro Ala Cys Thr Gly Cys Tyr (SEQ ID NO:87)
Asn Ser Ser Asn Tyr Cys Cys Glu Phe Cys Cys Asn
Pro Ala Cys Thr Gly Cys Tyr (SEQ ID NO:88)
Asn Ser Ser Asn Tyr Cys Cys Glu Pro Cys Cys Asn
Pro Ala Cys Thr Gly Cys Tyr (SEQ ID NO:89)
Asn Ser Ser Asn Tyr Cys Cys Glu Ser Cys Cys Asn
Pro Ala Cys Thr Gly Cys Tyr (SEQ ID NO:90)
Asn Ser Ser Asn Tyr Cys Cys Glu Thr Cys Cys Asn
Pro Ala Cys Thr Gly Cys Tyr (SEQ ID NO:91)
Asn Ser Ser Asn Tyr Cys Cys Glu Trp Cys Cys Asn
Pro Ala Cys Thr Gly Cys Tyr (SEQ ID NO:92)
Asn Ser Ser Asn Tyr Cys Cys Glu Val Cys Cys Asn
Pro Ala Cys Thr Gly Cys Tyr (SEQ ID NO:93)
Cys Cys Glu Ala Cys Cys Asn Pro Ala Cys Thr Gly
Cys Tyr (SEQ ID NO:94)
Cys Cys Glu Arg Cys Cys Asn Pro Ala Cys Thr Gly
Cys Tyr (SEQ ID NO:95)
Cys Cys Glu Asn Cys Cys Asn Pro Ala Cys Thr Gly
Cys Tyr (SEQ ID NO:96)
Cys Cys Glu Asp Cys Cys Asn Pro Ala Cys Thr Gly
Cys Tyr (SEQ ID NO:97)
Cys Cys Glu Cys Cys Cys Asn Pro Ala Cys Thr Gly
Cys Tyr (SEQ ID NO:98)
Cys Cys Glu Gln Cys Cys Asn Pro Ala Cys Thr Gly
Cys Tyr (SEQ ID NO:99)
Cys Cys Glu Glu Cys Cys Asn Pro Ala Cys Thr Gly
Cys Tyr (SEQ ID NO:100)
Cys Cys Glu Gly Cys Cys Asn Pro Ala Cys Thr Gly
Cys Tyr (SEQ ID NO:101)
Cys Cys Glu His Cys Cys Asn Pro Ala Cys Thr Gly
Cys Tyr (SEQ ID NO:102)
Cys Cys Glu Ile Cys Cys Asn Pro Ala Cys Thr Gly
Cys Tyr (SEQ ID NO:103)
Cys Cys Glu Lys Cys Cys Asn Pro Ala Cys Thr Gly
Cys Tyr (SEQ ID NO:104)
Cys Cys Glu Met Cys Cys Asn Pro Ala Cys Thr Gly
Cys Tyr (SEQ ID NO:105)
Cys Cys Glu Phe Cys Cys Asn Pro Ala Cys Thr Gly
Cys Tyr (SEQ ID NO:106)
Cys Cys Glu Pro Cys Cys Asn Pro Ala Cys Thr Gly
Cys Tyr (SEQ ID NO:107)
Cys Cys Glu Ser Cys Cys Asn Pro Ala Cys Thr Gly
Cys Tyr (SEQ ID NO:108)
Cys Cys Glu Thr Cys Cys Asn Pro Ala Cys Thr Gly
Cys Tyr (SEQ ID NO:109)
Cys Cys Glu Trp Cys Cys Asn Pro Ala Cys Thr Gly
Cys Tyr (SEQ ID NO:110)
Cys Cys Glu Val Cys Cys Asn Pro Ala Cys Thr Gly
Cys Tyr

In an eighteenth aspect, the invention features a method for treating congestive heart failure, the method comprising administering a complete or partial agonist of the intestinal guanylate cyclase (GC-C) receptor. The agonist can be administered in combination with another agent for treatment of congestive heart failure, for example, a natriuretic peptide such as atrial natriuretic peptide, brain natriuretic peptide or C-type natriuretic peptide), a diuretic, or an inhibitor of angiotensin converting enzyme.

In a nineteenth aspect, the invention features a method for treating BPH, the method comprising administering a complete or partial agonist of the intestinal guanylate cyclase (GC-C) receptor. The agonist can be administered in combination with another agent for treatment of BPH, for example, a 5-alpha reductase inhibitor (e.g., finasteride) or an alpha adrenergic inhibitor (e.g., doxazosine).

In a twentieth aspect, the invention features a method for treating obesity, the method comprising administering a complete or partial agonist of the intestinal guanylate cyclase (GC-C) receptor. The agonist can be administered in combination with another agent for treatment of obesity, for example, gut hormone fragment peptide YY$_{3-36}$ (PYY$_{3-36}$) (*N. Engl. J. Med.* 349:941, 2003; ikpeapge daspeelnry yaslrhylnl vtrqry) glp-1 (glucagon-like peptide-1), exendin-4 (an inhibitor of glp-1), sibutramine, phentermine, phendimetrazine, benzphetamine hydrochloride (Didrex), orlistat (Xenical), diethylpropion hydrochloride (Tenuate), fluoxetine (Prozac), bupropion, ephedra, chromium, *garcinia cambogia*, benzocaine, bladderwrack (focus vesiculosus), chitosan, nomame herba, galega (Goat's Rue, French Lilac), conjugated linoleic acid, L-carnitine, fiber (*psyllium, plantago*, guar fiber), caffeine, dehydroepiandrosterone, germander (*teucrium chamaedrys*), B-hydroxy-β-methylbutyrate, and pyruvate. A peptide useful for treating obesity can be administered as a co-therapy with a peptide of the invention either as a distinct molecule or as part of a fusion protein with a peptide of the invention. Thus, for example, PYY$_{3-36}$ can be fused to the carboxy or amino terminus of a peptide of the invention. Such a fusion protein can include a chymostrypsin or trypsin cleavage site that can permit cleavage to separate the two peptides.

The peptides and a agonist of the intestinal guanylate cyclase (GC-C) receptor can be used to treat constipation or decreased intestinal motility, slow digestion or slow stomach emptying. The peptides can be used to relieve one or more symptoms of IBS (bloating, pain, constipation), GERD (acid reflux into the esophagus), functional dyspepsia, or gastroparesis (nausea, vomiting, bloating, delayed gastric emptying) and other disorders described herein.

The details of one or more embodiments of the invention are set forth in the accompanying descriptions. All of the publications, patents and patent applications are hereby incorporated by reference.

FIGURES

FIG. 1*a* depicts the results of LCMS analysis of recombinant SEQ ID NO:26 peptide and SEQ ID NO:28 peptide.

Figure 1B:
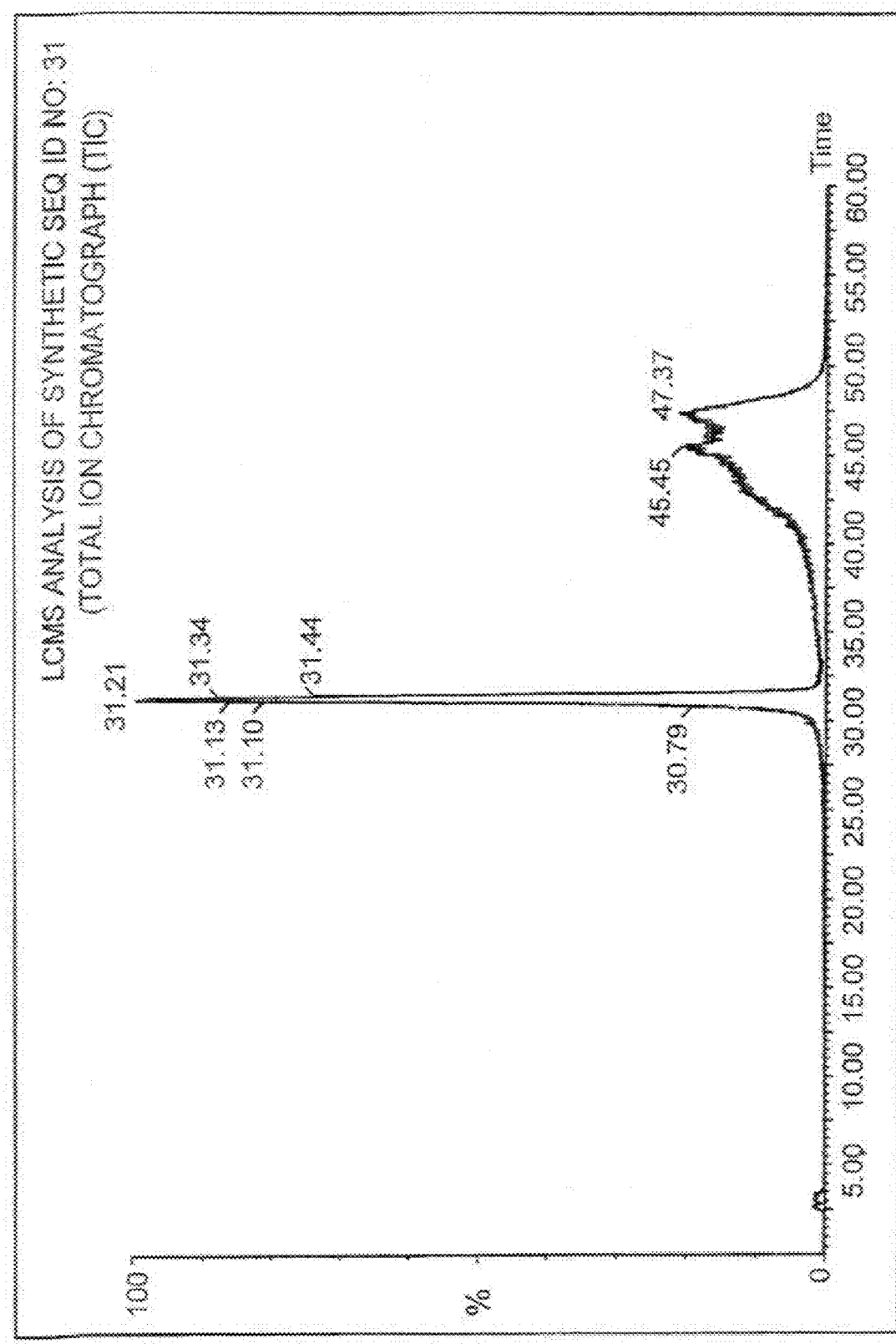

FIGS. 1*b* and *c* depict the results of LCMS analysis of synthetic SEQ ID NO:31 peptide and the blank.

Figure 2:
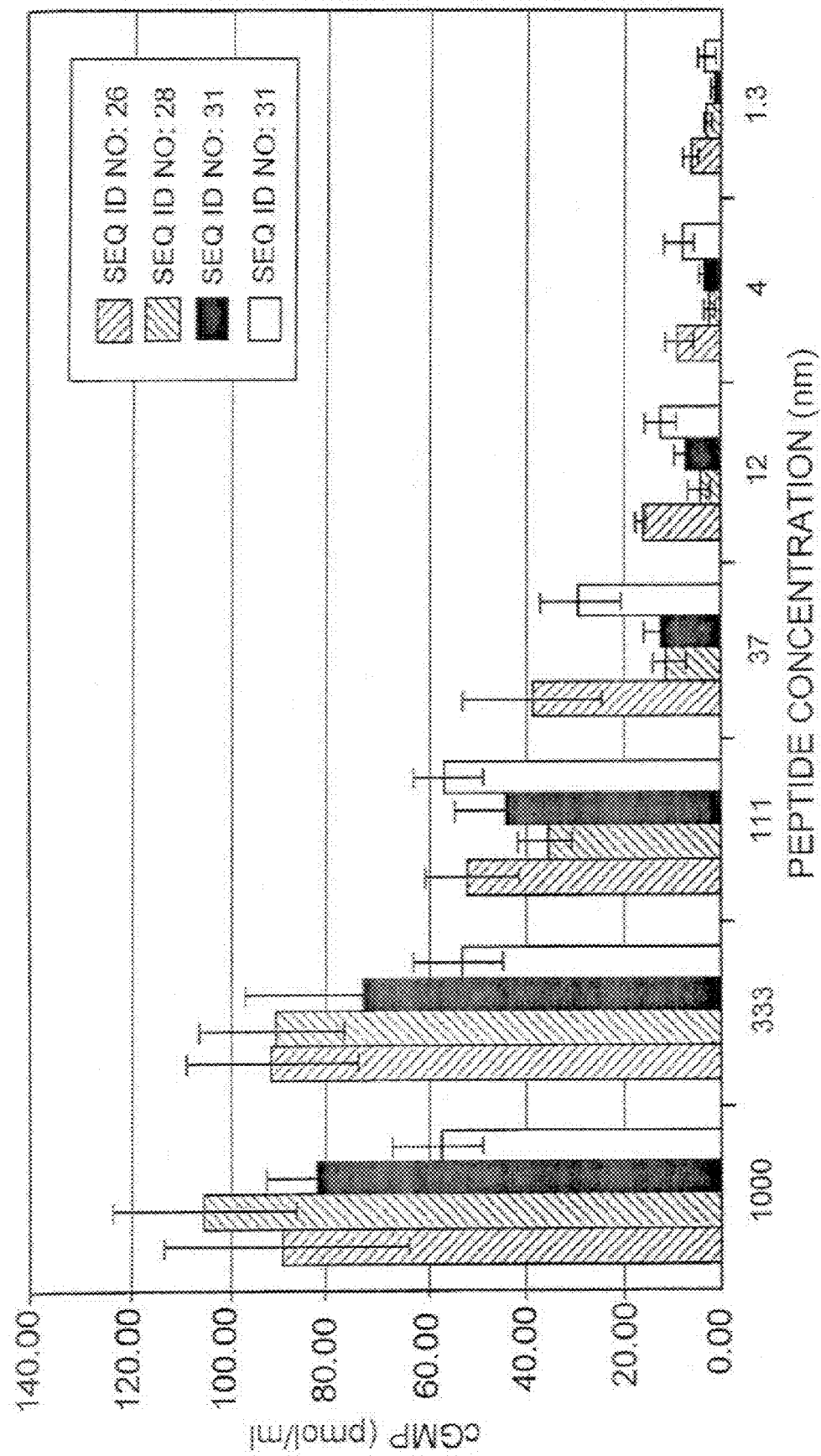

FIG. 2 depicts the results of the intestinal GC-C receptor activity assay of synthetic peptide, SEQ ID NO:28 peptide and two different SEQ ID NO:31 peptides. FIG. 3*a* depicts the effect of recombinant. SEQ ID NO:26 peptide and Zelnorm® in a murine gastrointestinal transit model.

Figure 3B:
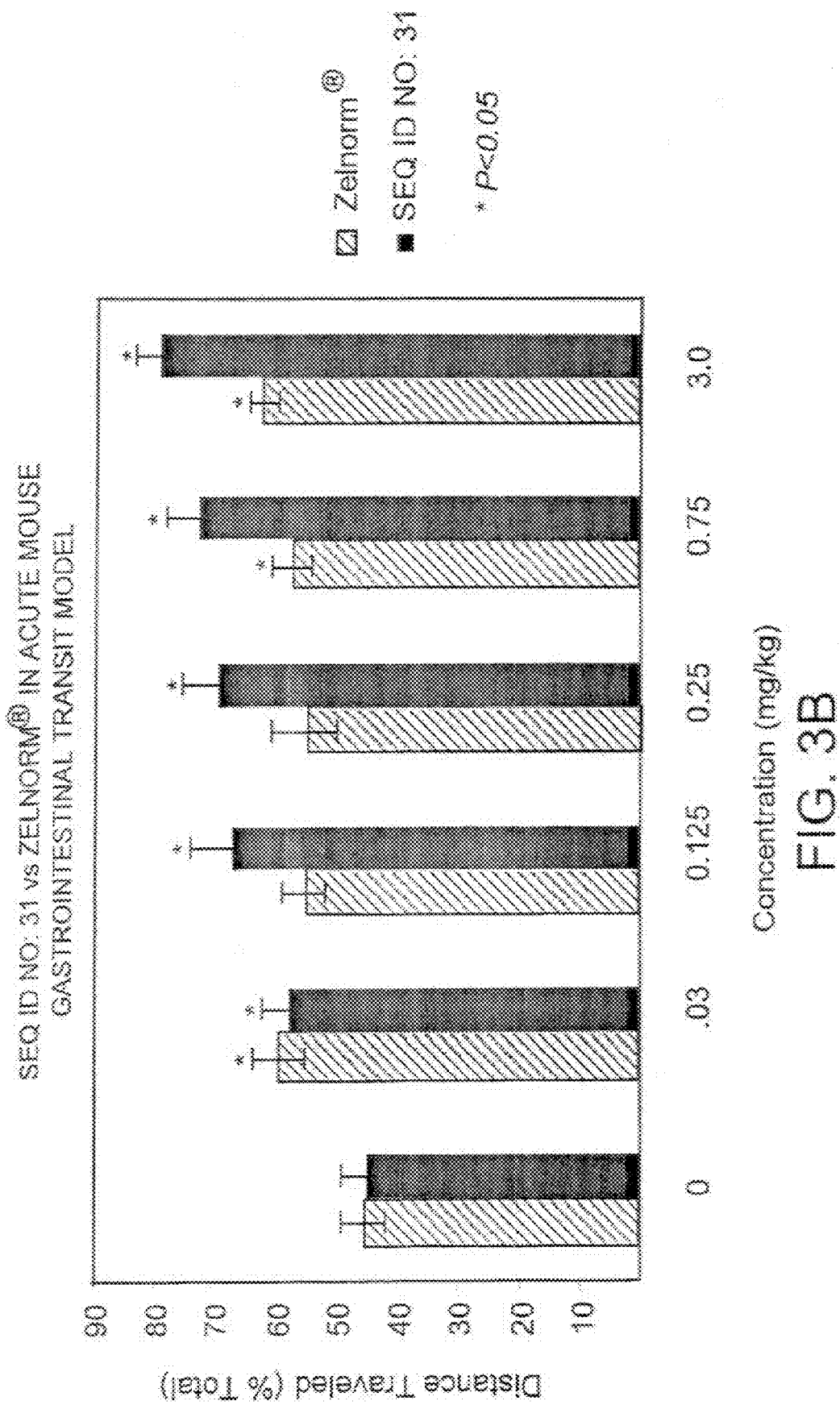

FIG. 3*b* depicts the effect of synthetic SEQ ID NO:31 peptide and Zelnorm® in an acute murine gastrointestinal transit model.

FIG. 3*b* depicts the effect of synthetic SEQ ID NO:31 peptide and Zelnorm® in an chronic murine gastrointestinal transit model.

Figure 4A:
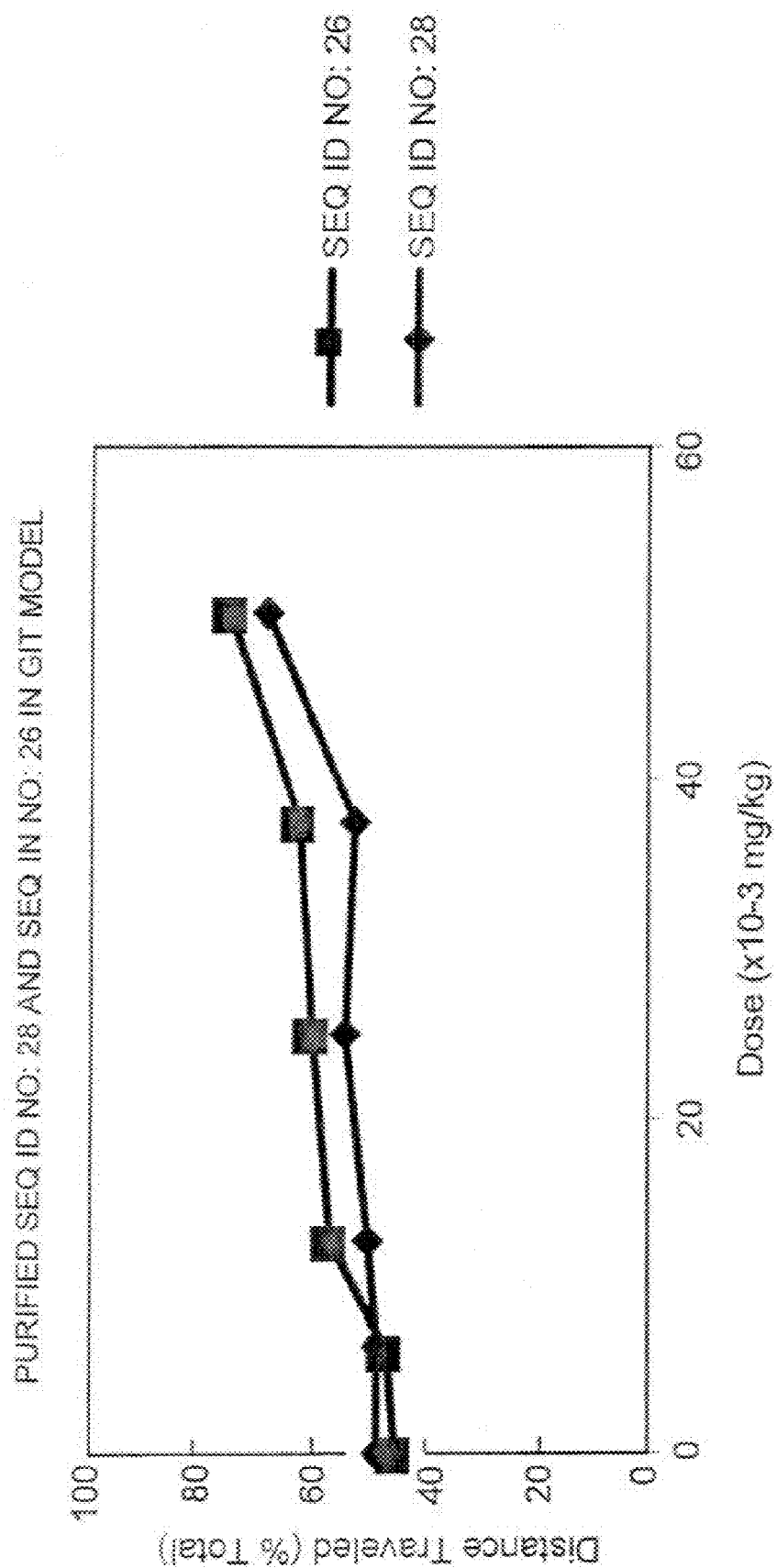
Figure 4B:
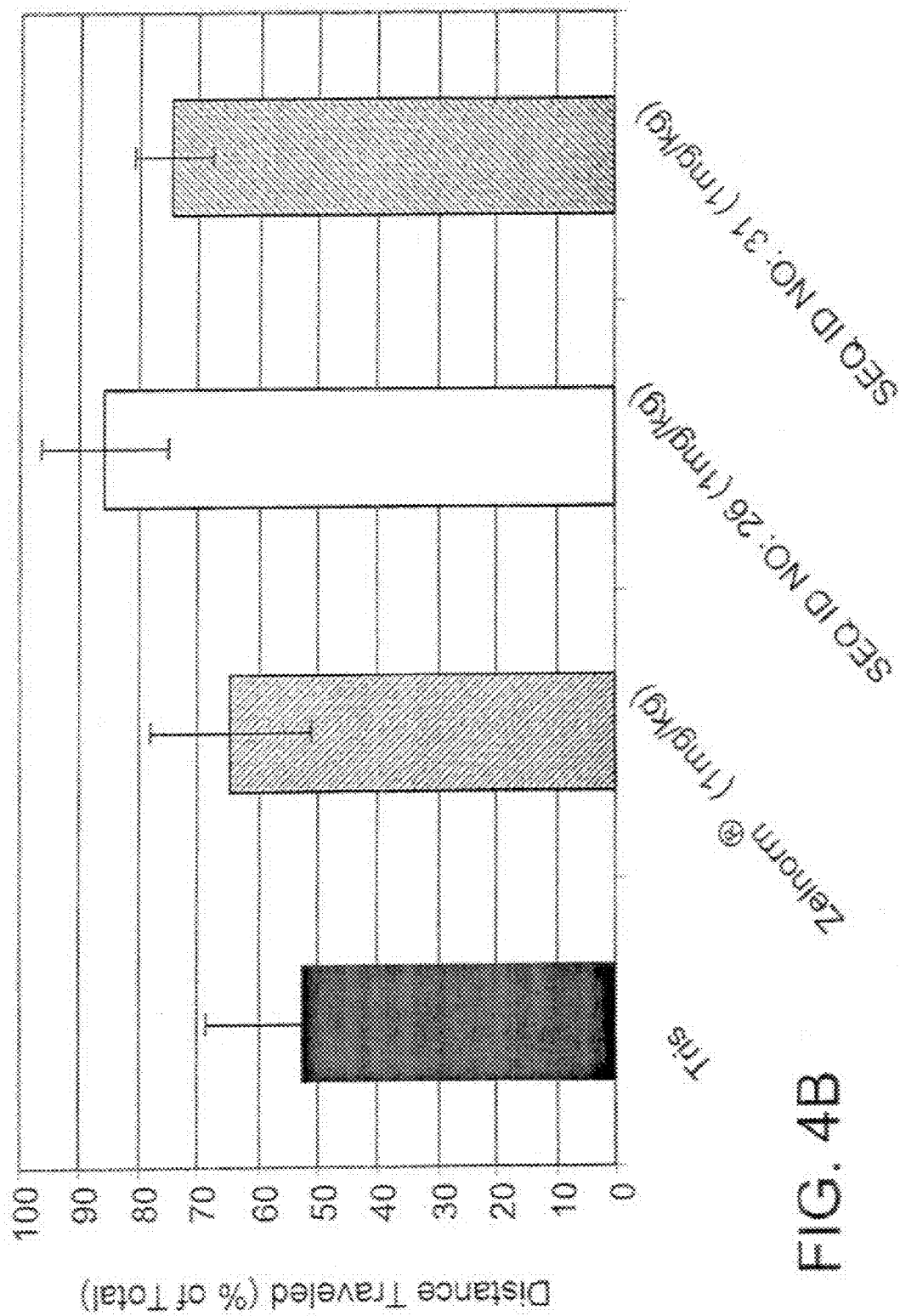

FIGS. 4*a* and 4*b* depict the effect of peptides SEQ ID NO:28, SEQ ID NO:31, and SEQ ID NO:26 in an acute murine gastrointestinal transit model.

Figure 4C:
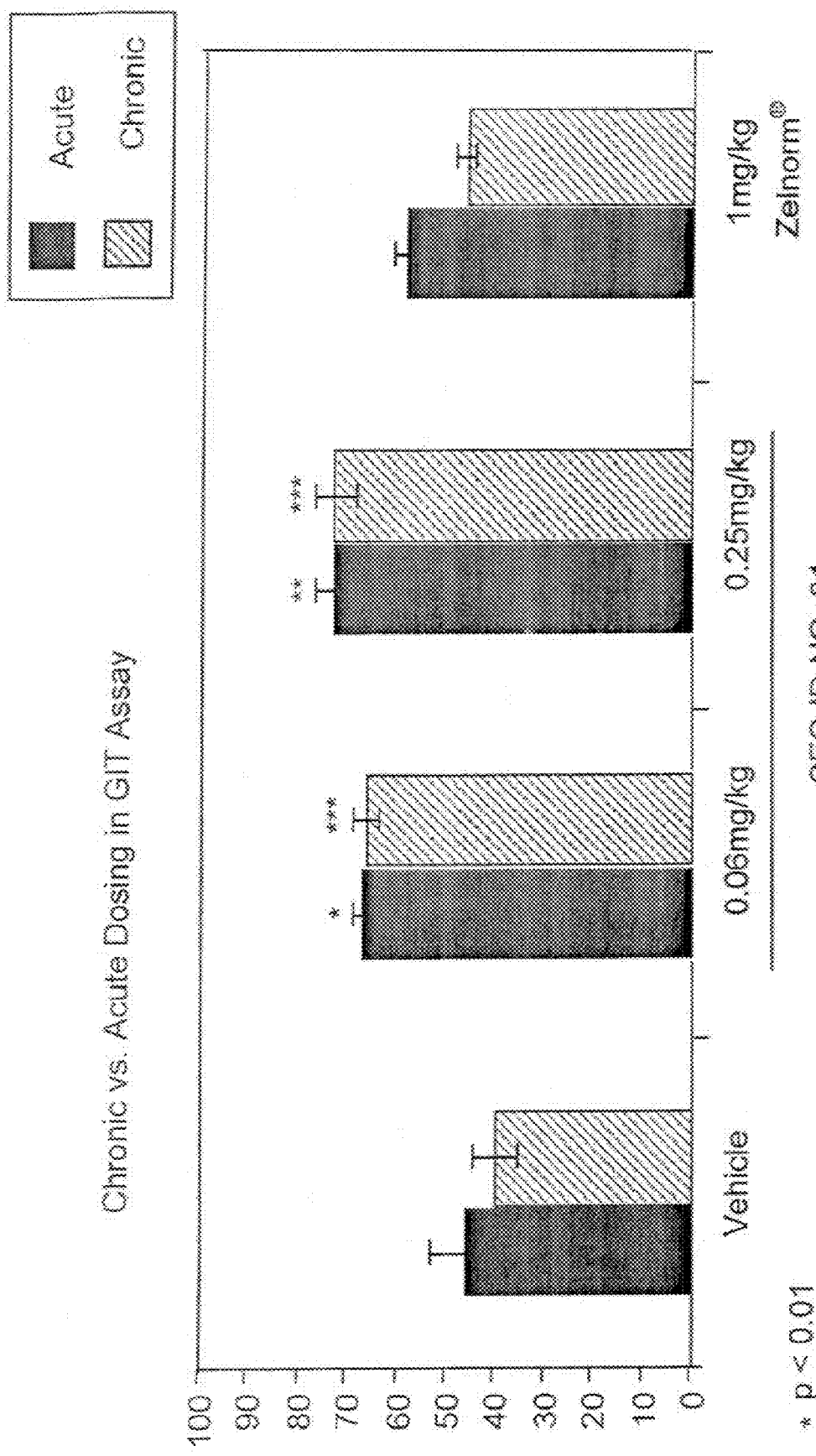

FIG. 4*c* depicts the effect of SEQ ID NO:31 peptide in a chronic murine gastrointestinal transit model.

Figure 5A:
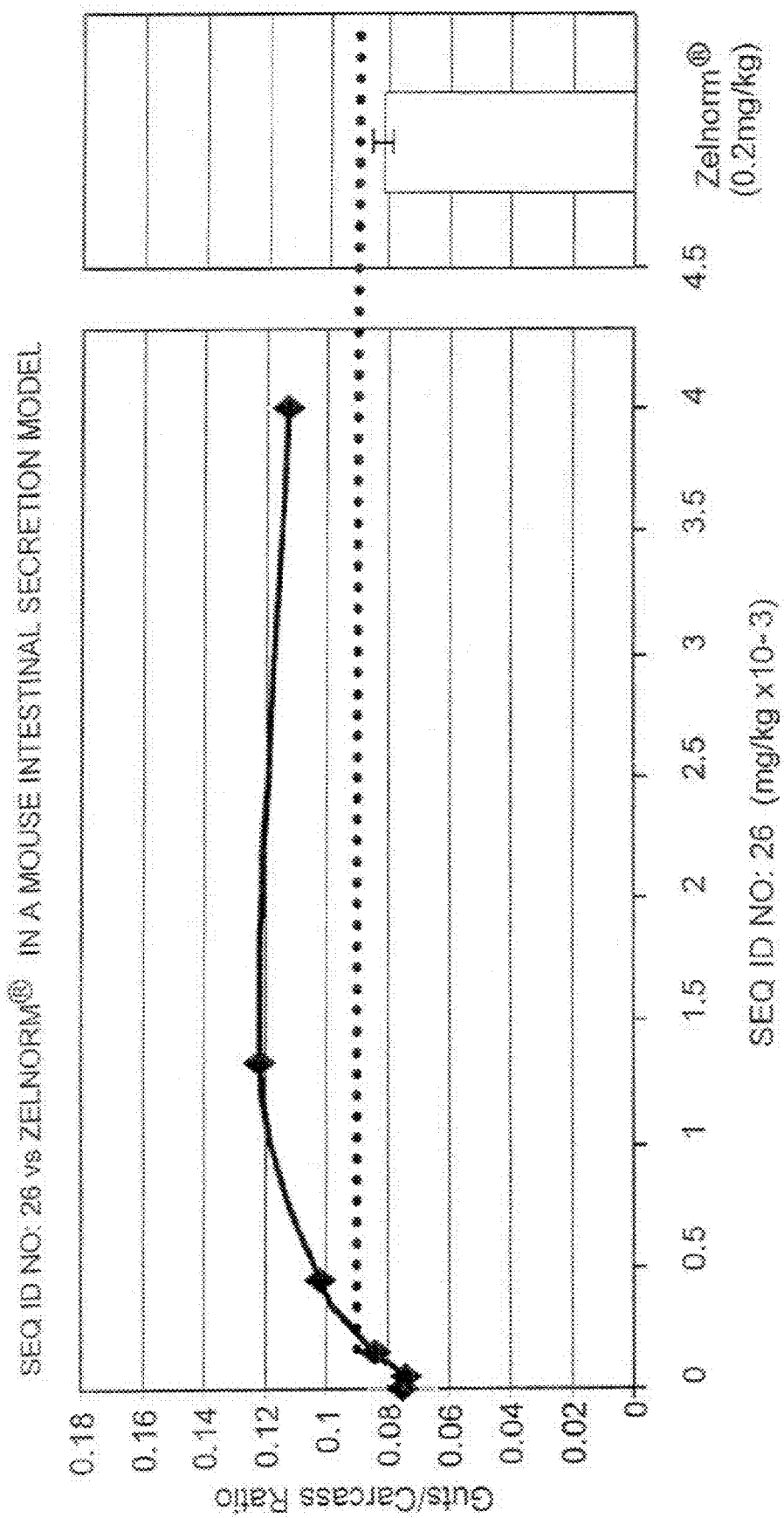

FIG. 5*a* depicts the effect of SEQ ID NO:26 peptide and Zelnorm® in a suckling mouse intestinal secretion model.

Figure 5B:
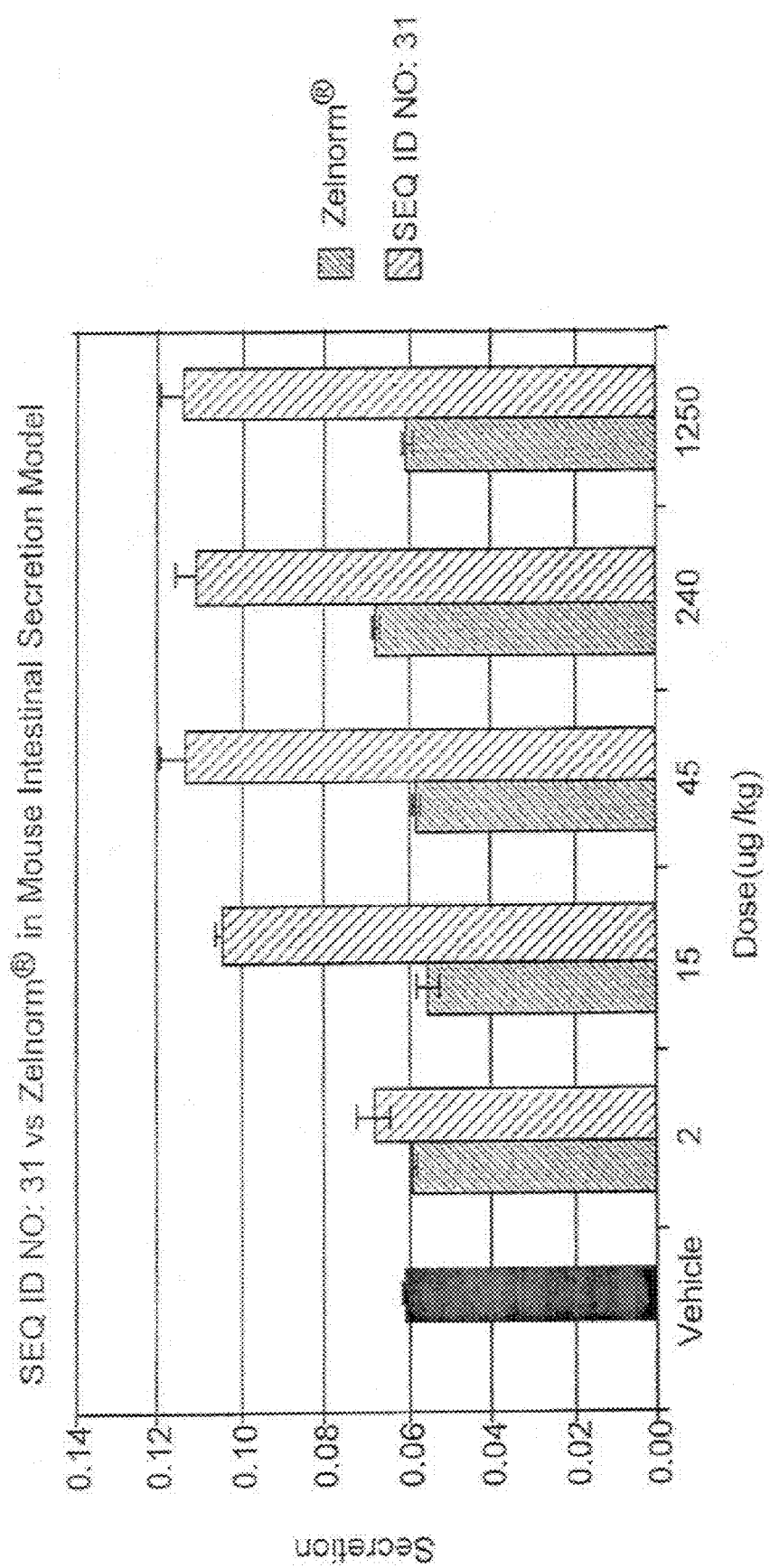

FIG. 5*b* depicts the effects of SEQ ID NO:31 and Zelnorm® in a mouse intestinal secretion model.

Figure 6A:
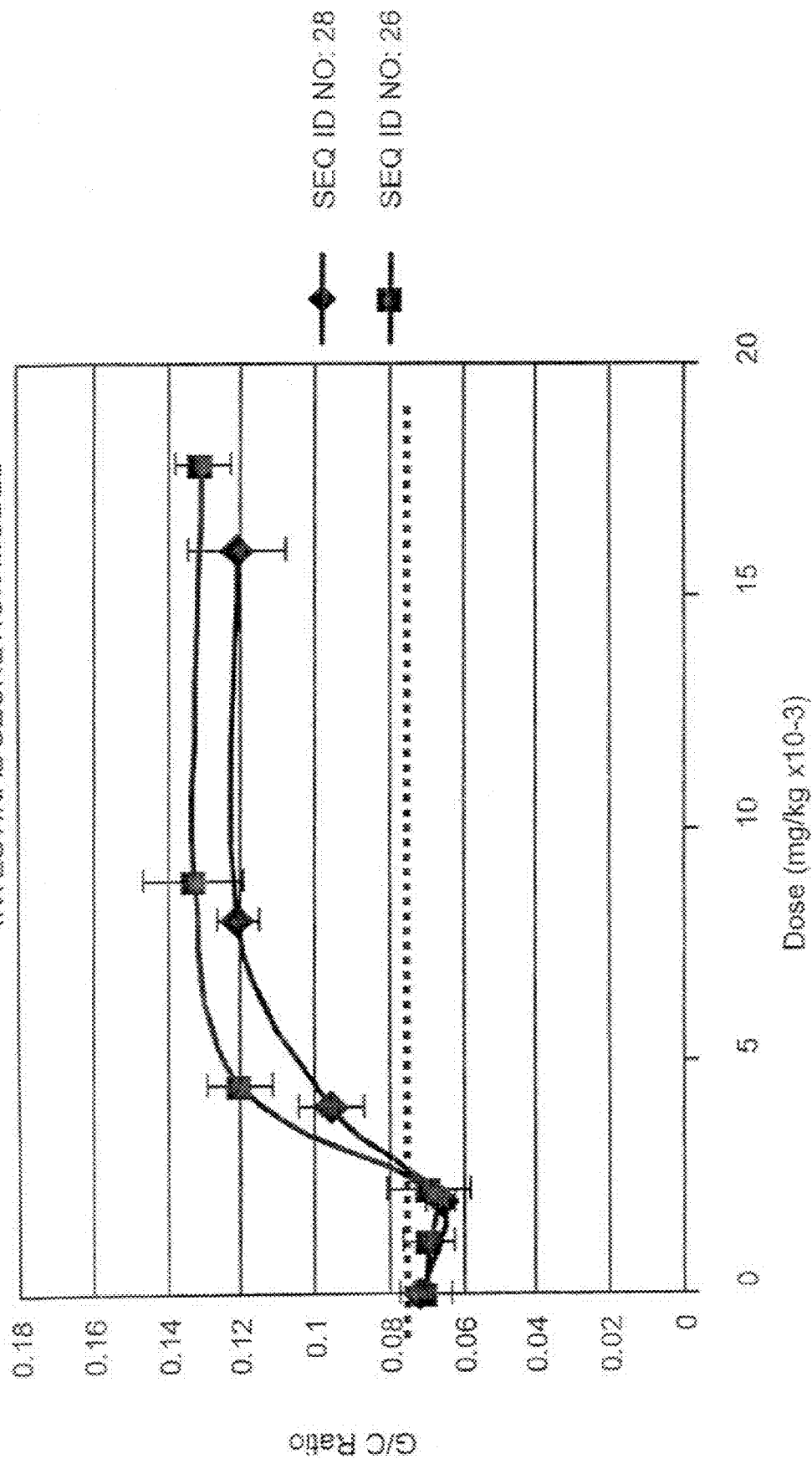
Figure 6B:
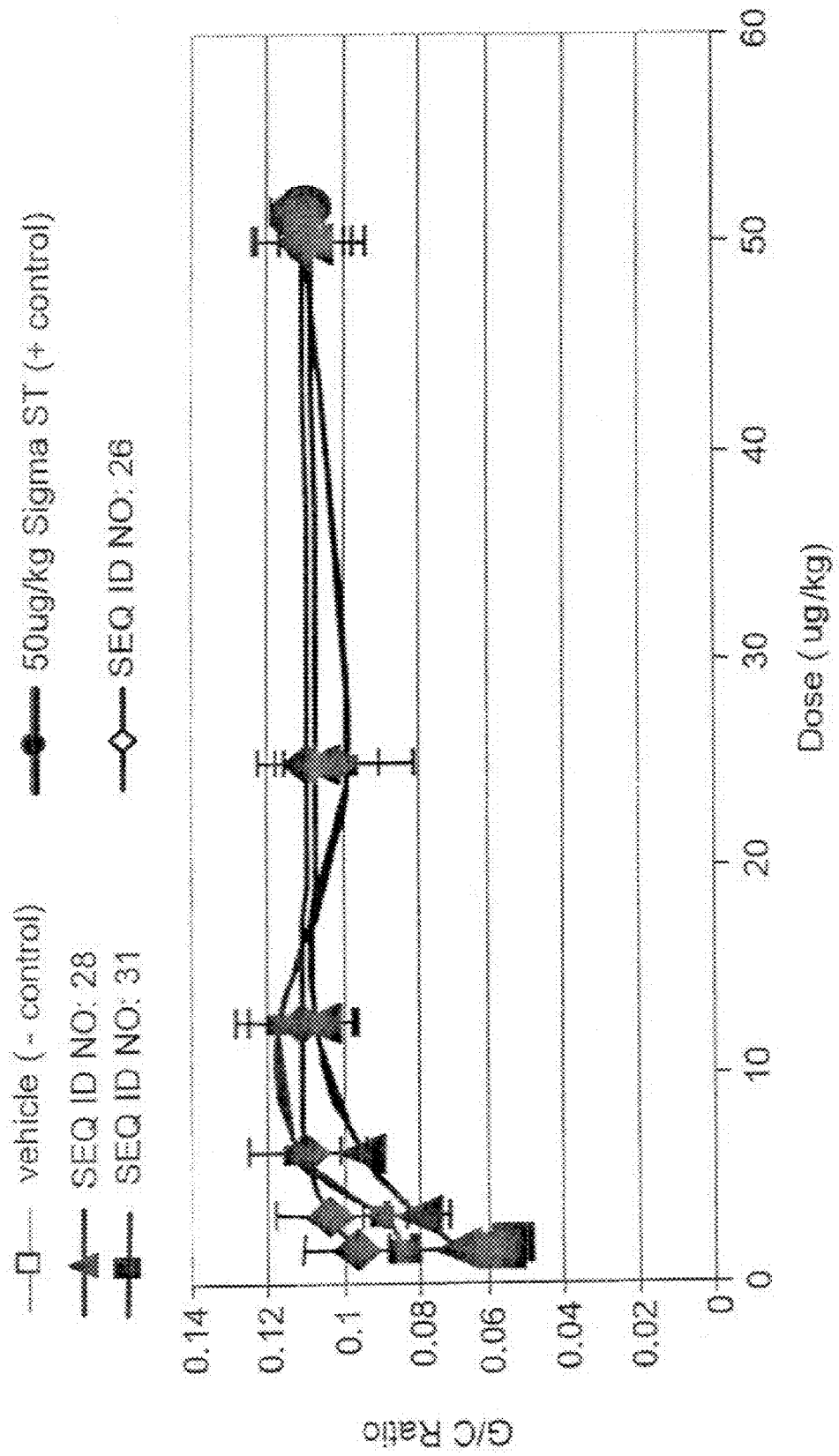

FIGS. 6*a* and 6*b* depict the effects of SEQ ID NO:26, SEQ ID NO:31, and SEQ ID NO:28 peptides in a mouse intestinal secretion model.

Figure 7:
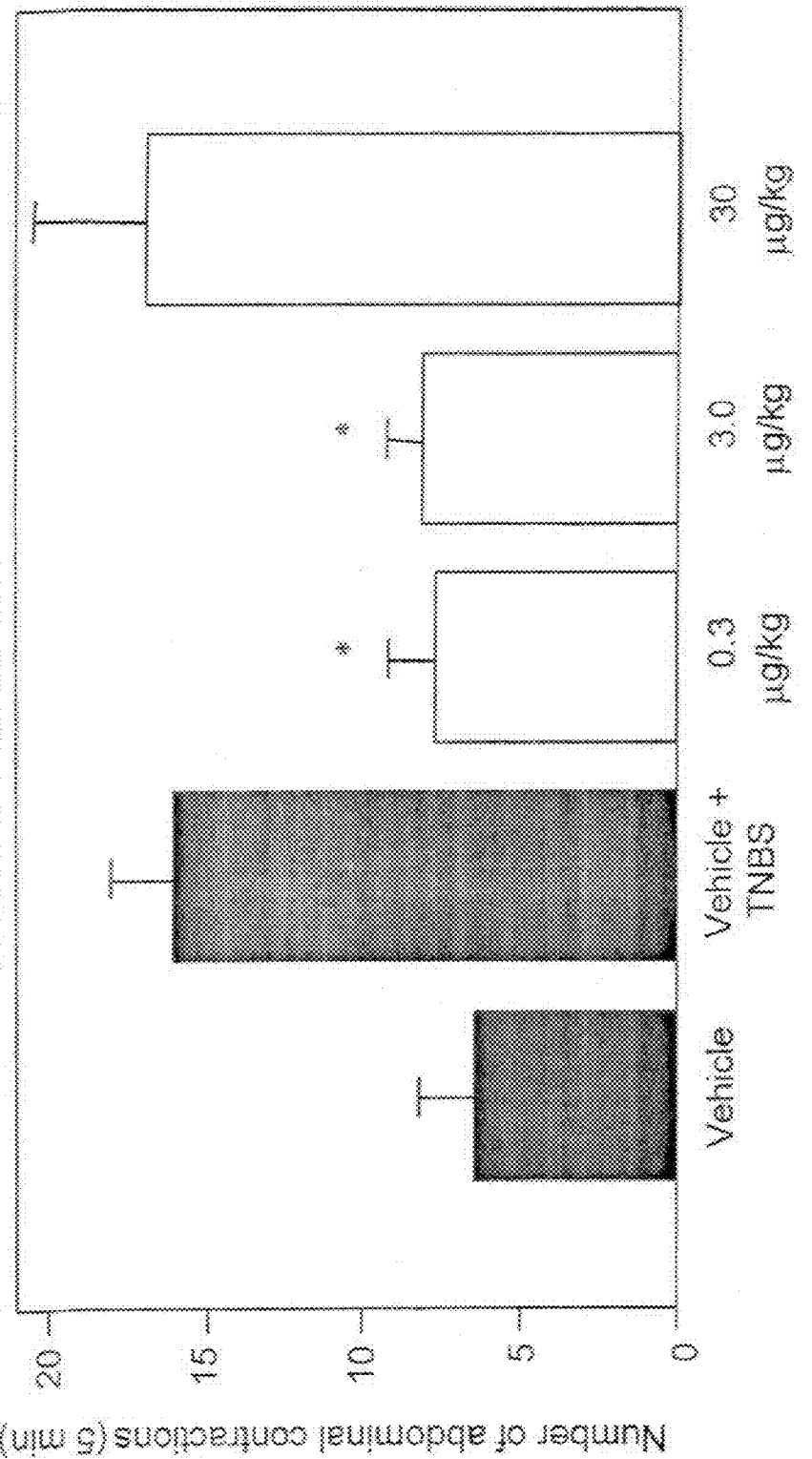

FIG. 7 shows the results of experiment in which SEQ ID NO:31 activity was analyzed in the TNBS colonic distention model.

Figure 8A:
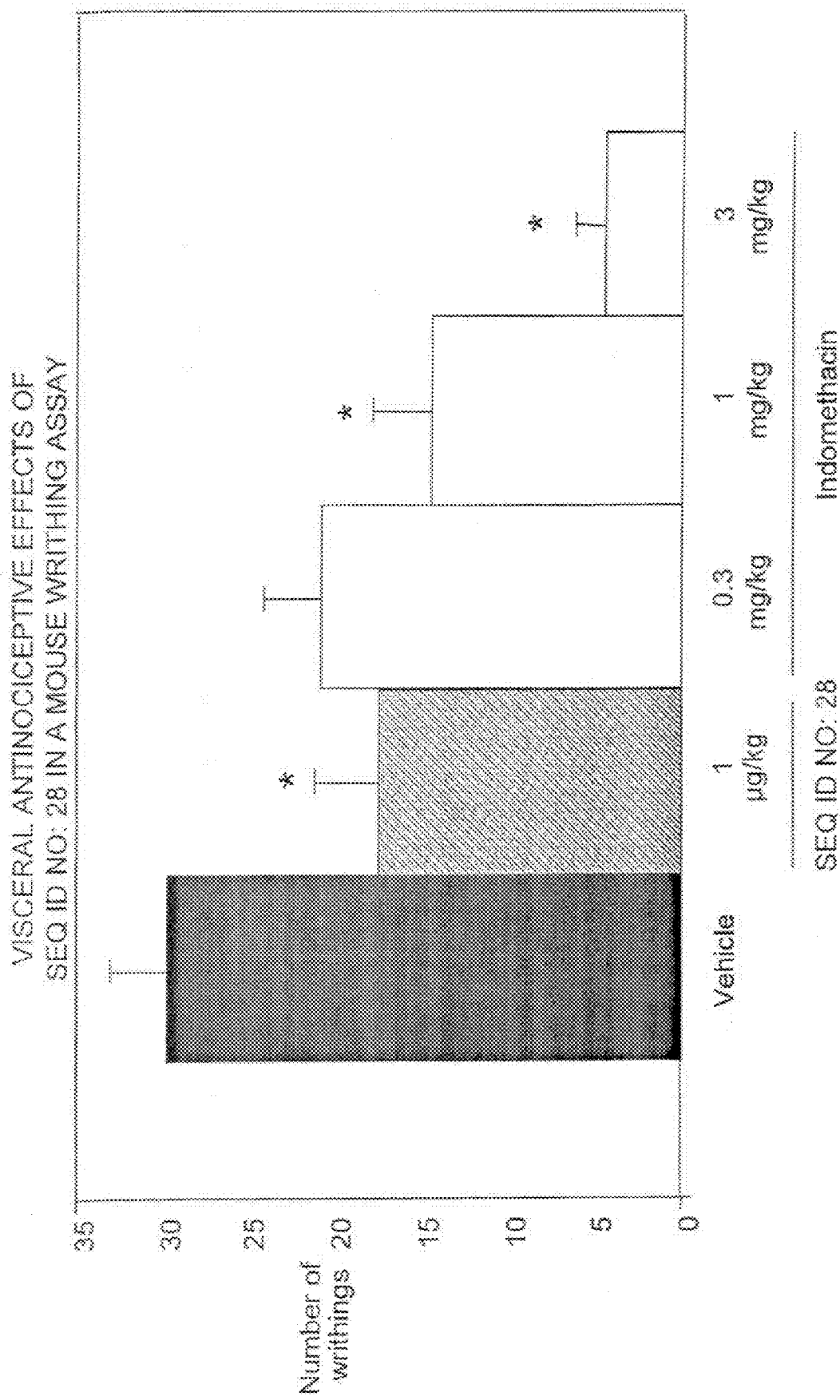
Figure 8B:
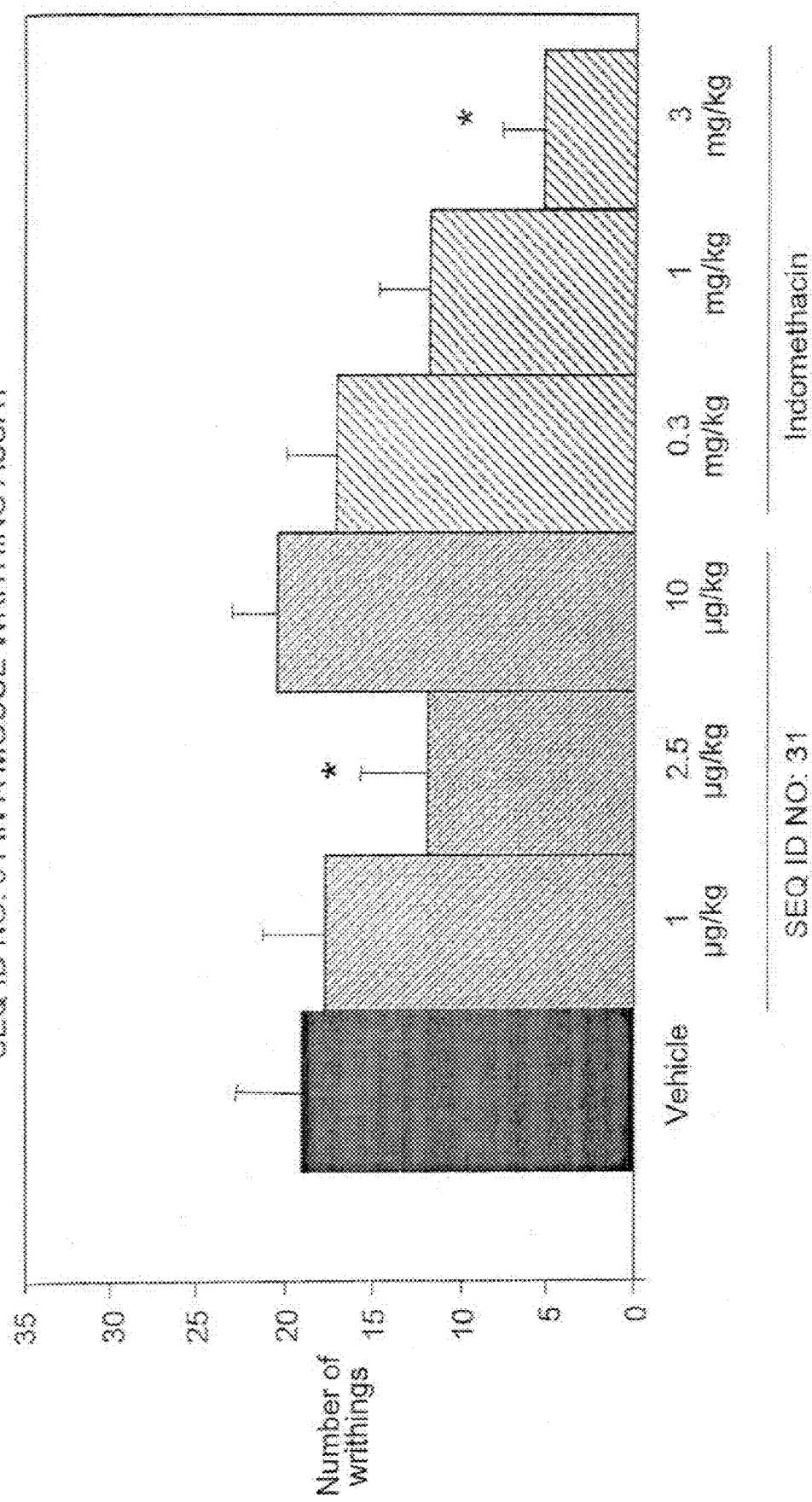

FIGS. 8*a* and 8*b* show the effects of differing doses of SEQ ID NO:28 and SEQ ID NO:31 in the PBQ writhing assay.

Figure 9:
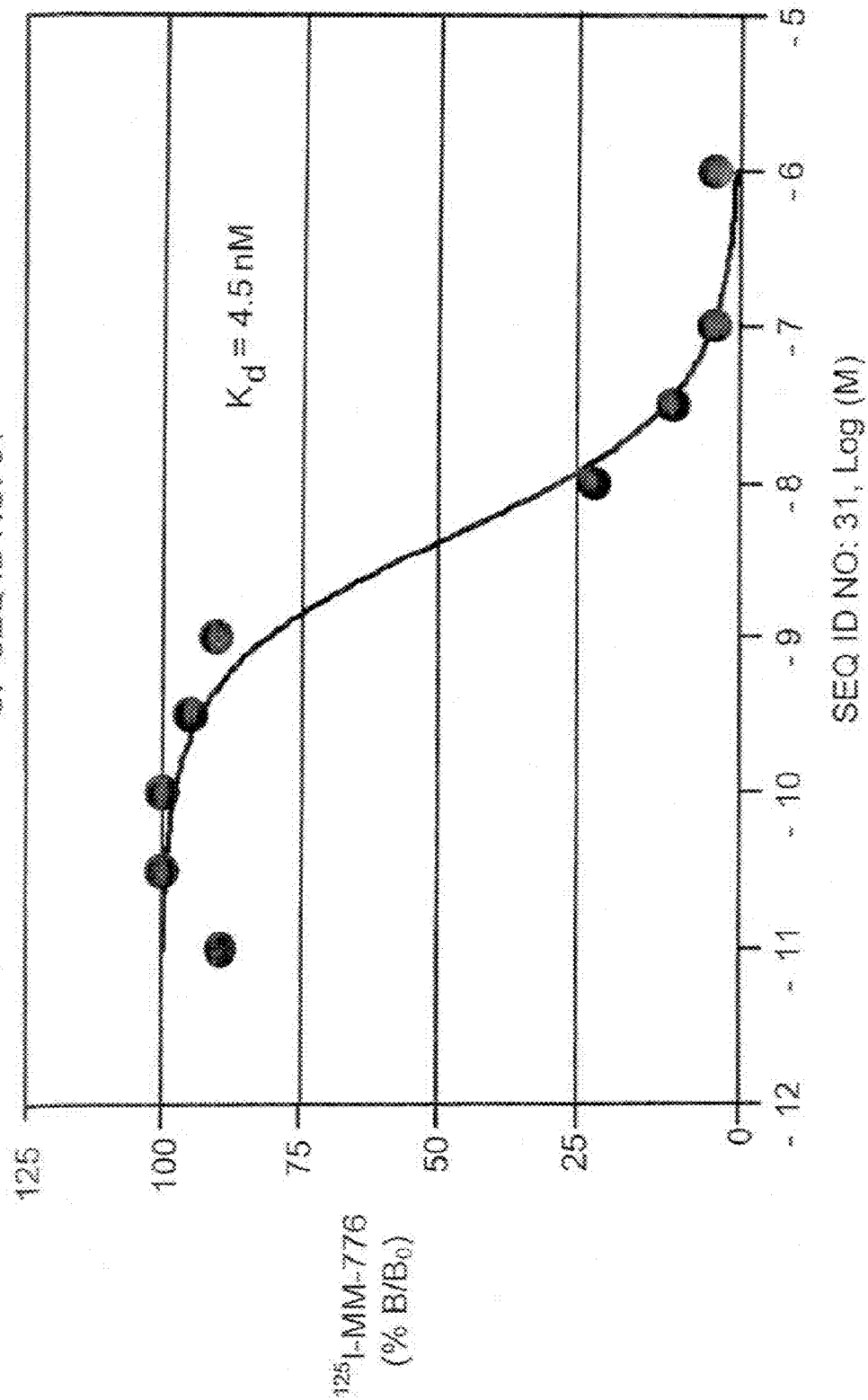

FIG. 9 shows the results of Kd determination analysis using SEQ ID NO:31 in a competitive radioligand binding assay.

Figure 10A:
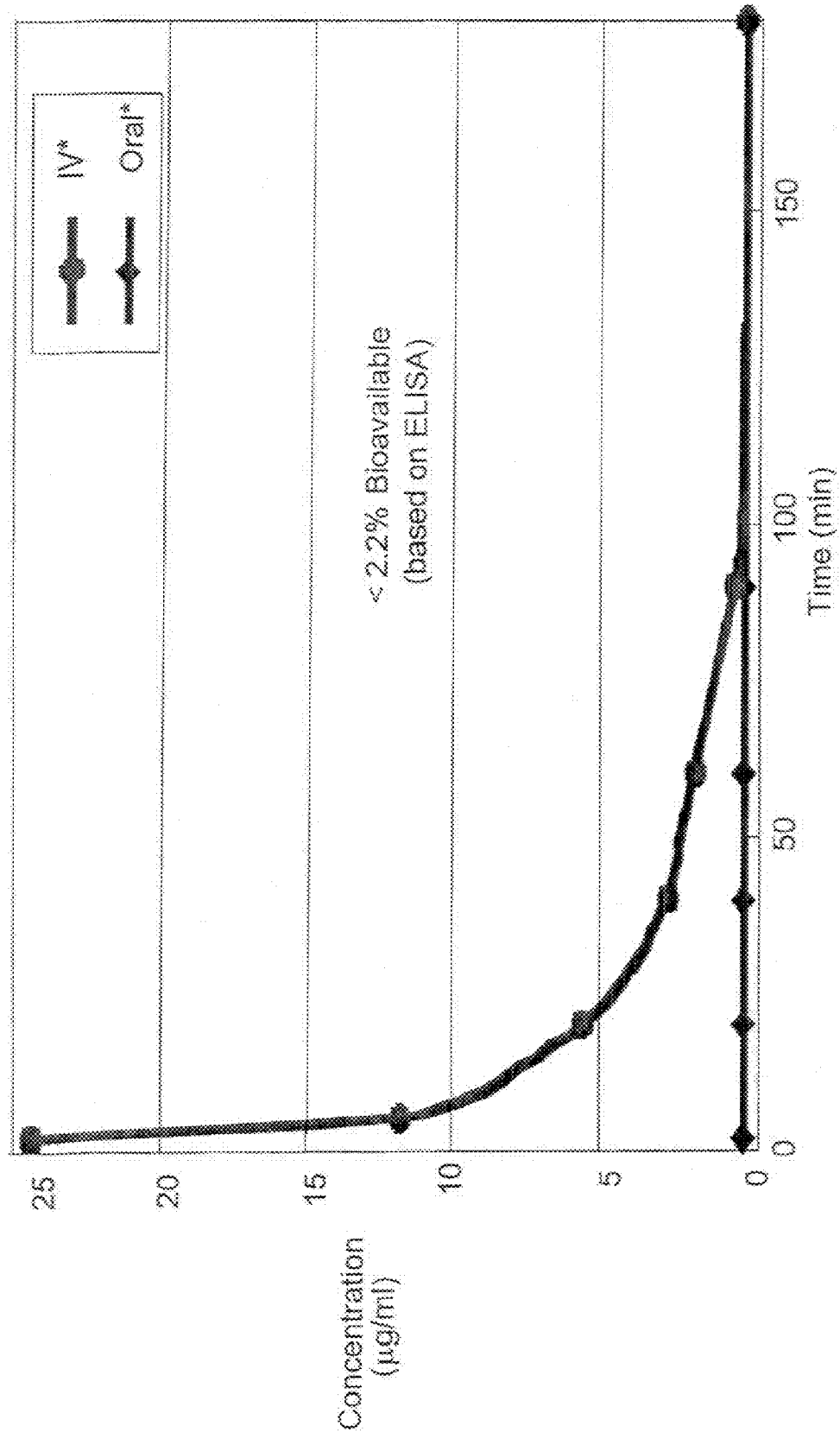
Figure 10B:
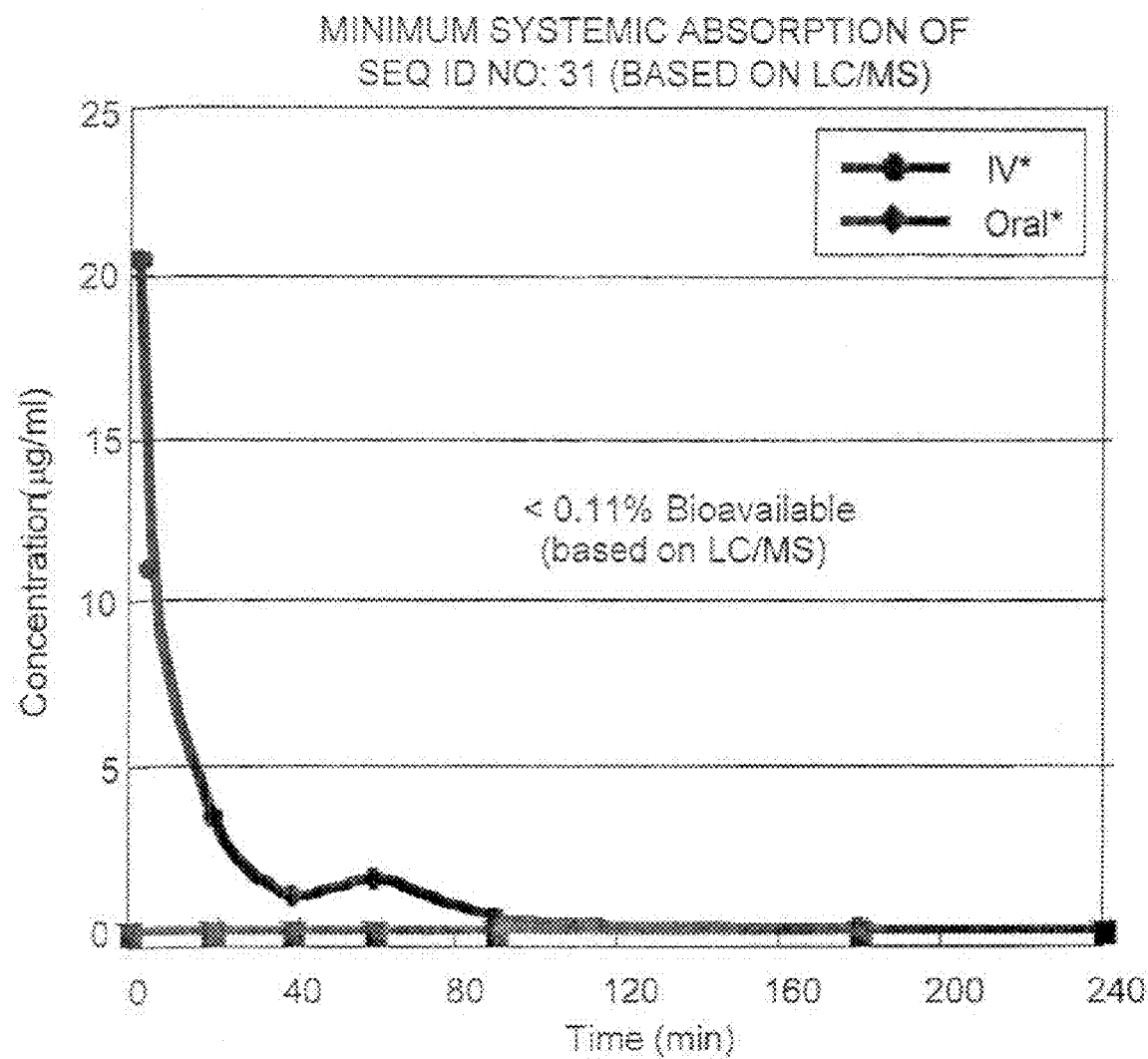

FIGS. 10*a* and 10*b* show bioavailability data for IV and orally administered SEQ ID NO:31 as detected by an ELISA assay and LCMS.

DETAILED DESCRIPTION

The peptides of the invention bind to the intestinal guanylate cyclase (GC-C) receptor, a key regulator of fluid and electrolyte balance in the intestine. When stimulated, this receptor, which is located on the apical membrane of the intestinal epithelial surface, causes an increase in intestinal epithelial cyclic GMP (cGMP). This increase in cGMP is believed to cause a decrease in water and sodium absorption and an increase in chloride and potassium ion secretion, leading to changes in intestinal fluid and electrolyte transport and increased intestinal motility. The intestinal GC-C receptor possesses an extracellular ligand binding region, a transmembrane region, an intracellular protein kinase-like region and a cyclase catalytic domain. Proposed functions for the GC-C receptor are fluid and electrolyte homeostasis, the regulation of epithelial cell proliferation and the induction of apoptosis (Shalubhai 2002 Curr Opin Drug Dis Devel 5:261-268).

In addition to being expressed in the intestine by gastrointestinal epithelial cells, GC-C is expressed in extra-intestinal tissues including kidney, lung, pancreas, pituitary, adrenal, developing liver (reviewed in Vaandrager 2002, Mol Cell Biochem 230:73-83) and male and female reproductive tissues (reviewed in Vaandrager 2002 *Mol Cell Biochem* 230: 73-83)) This suggests that the GC-C receptor agonists can be used in the treatment of disorders outside the GI tract, for example, congestive heart failure and benign prostatic hyperplasia.

Ghrelin, a peptide hormone secreted by the stomach, is a key regulator of appetite in humans. Ghrelin expression levels are regulated by fasting and by gastric emptying (Kim et al., 2003, Neuroreprt 14:1317-20; Gualillo et al., 2003, FEBS Letts 552: 105-9). Thus, by increasing gastrointestinal motility, GC-C receptor agonists may also be used to regulate obesity.

In humans, the GC-C receptor is activated by guanylin (Gn) (U.S. Pat. No. 5,969,097), uroguanylin (Ugn) (U.S. Pat. No. 5,140,102) and lymphoguanylin (Forte et al., 1999, *Endocrinology* 140:1800-1806). Interestingly, these agents are 10-100 fold less potent than a class of bacterially derived peptides, termed ST (reviewed in Gianella 1995 J Lab Clin Med 125:173-181). ST peptides are considered super agonists of GC-C and are very resistant to proteolytic degradation.

ST peptide is capable of stimulating the enteric nervous system (Rolfe et al., 1994, J Physiolo 475: 531-537; Rolfe et al., 1999, Gut 44: 615-619; Nzegwu et al., 1996, Exp Physiol 81: 313-315). Also, cGMP has been reported to have anitnociceptive effects in multiple animal models of pain (Lazaro Ibanez et al., 2001, Eur J Pharmacol 426: 39-44; Soares et al., 2001, British J Pharmacol 134: 127-131; Jain et al., 2001, Brain Res 909:170-178; Amarante et al., 2002, Eur J Pharmacol 454:19-23). Thus, GC-C agonists may have both an analgesic as well an anti-inflammatory effect.

In bacteria, ST peptides are derived from a preproprotein that generally has at least 70 amino acids. The pre and pro regions are cleaved as part of the secretion process, and the resulting mature protein, which generally includes fewer than 20 amino acids, is biologically active. Among the known bacterial ST peptides are: *E. coli* ST Ib (Moseley et al. (1983) *Infect. Immun.* 39:1167) having the mature amino acid sequence Asn Ser Ser Asn Tyr Cys Cys Glu Leu Cys Cys Asn Pro Ala Cys Thr Gly Cys Tyr (SEQ ID NO:1); *E. coli* ST Ia (So and McCarthy (1980) *Proc. Natl. Acad. Sci.* USA 77:4011) having the mature amino acid sequence Asn Thr Phe Tyr Cys Cys Glu Leu Cys Cys Asn Pro Ala Cys Ala Gly Cys Tyr (SEQ ID NO:2); *E. coli* ST I* (Chan and Giannella (1981) *J. Biol. Chem.* 256:7744) having the mature amino acid sequence Asn Thr Phe Tyr Cys Cys Glu Leu Cys Cys Tyr Pro Ala Cys Ala Gly Cys Asn (SEQ ID NO:3); *C. freundii* ST peptide (Guarino et al. (1989) *Infect. Immun.* 57:649) having the mature amino acid sequence Asn Thr Phe Tyr Cys Cys Glu Leu Cys Cys Asn Pro Ala Cys Ala Gly Cys Tyr (SEQ ID NO:4); *Y. enterocolitica* ST peptides, Y-ST(Y-STa), Y-STb, and Y-STc (reviewed in Huang et al. (1997) *Microb. Pathog.* 22:89) having the following pro-form amino acid sequences: Gln Ala Cys Asp Pro Pro Ser Pro Pro Ala Glu Val Ser Ser Asp Trp Asp Cys Cys Asp Val Cys Cys Asn Pro Ala Cys Ala Gly Cys (SEQ ID NO:5) (as well as a Ser-7 to Leu-7 variant of Y-STa (SEQ ID NO:122), (Takao et al. (1985) *Eur. J. Biochem.* 152:199)); Lys Ala Cys Asp Thr Gln Thr Pro Ser Pro Ser Glu Glu Asn Asp Asp Trp Cys Cys Glu Val Cys Cys Asn Pro Ala Cys Ala Gly Cys (SEQ ID NO:6); Gln Glu Thr Ala Ser Gly Gln Val Gly Asp Val Ser Ser Ser Thr Ile Ala Thr Glu Val Ser Glu Ala Glu Cys Gly Thr Gln Ser Ala Thr Thr Gln Gly Glu Asn Asp Trp Asp Trp Cys Cys Glu Leu Cys Cys Asn Pro Ala Cys Phe Gly Cys (SEQ ID NO:7), respectively; *Y. kristensenii* ST peptide having the mature amino acid sequence Set Asp Trp Cys Cys Glu Val Cys Cys Asn Pro Ala Cys Ala Gly Cys (SEQ ID NO:8); *V. cholerae* non-01 ST peptide (Takao et al. (1985) *FEBS lett.* 193:250) having the mature amino acid sequence Ile Asp Cys Cys Glu Ile Cys Cys Asn Pro Ala Cys Phe Gly Cys Leu Asn (SEQ ID NO:9); and *V. mimicus* ST peptide (Arita (1991) et al. *FEMS Microbiol. Lett.* 79:1.05) having the mature amino acid sequence Ile Asp Cys Cys Glu Ile Cys Cys Asn Pro Ala Cys Phe Gly Cys Leu Asn (SEQ ID NO:10). The Table below provides sequences of all or a portion of a number of mature ST peptides.

| GenBank® Accession | CenBank® GI | Sequence |
|---|---|---|
| QHEC1B | 69638 | NSSNYCCELCCNPACTGCY (SEQ ID NO:1) |
| P01559 | 123711 | NTFYCCELCCNPACAGCY (SEQ ID NO:2) |
| AAA24653 | 147878 | NTFYCCELCCNPACAPCY (SEQ ID NO:11) |
| P01560 | 123707 | NTFYCCELCCYPACAGCN (SEQ ID NO:3) |
| AAA27561 | 295439 | IDCCEICCNPACFGCLN (SEQ ID NO:9) |
| P04429 | 123712 | IDCCEICCNPACFGCLN (SEQ ID NO:10) |
| S34671 | 421286 | IDCCEICCNPACF (SEQ ID NO:12) |
| CAA52209 | 395161 | IDCCEICCNPACFG (SEQ ID NO:13) |
| A54534 | 628844 | IDCCEICCNPACFGCLN (SEQ ID NO:14) |
| AAL02159 | 15592919 | IDRCEICCNPACFGCLN (SEQ ID NO:15) |
| AAA18472 | 487395 | DWDCCDVCCNPACAGC (SEQ ID NO:16) |
| S25659 | 282047 | DWDCCDVCCNPACAGC (SEQ ID NO:17) |
| P74977 | 3913874 | NDDWCCEVCCNPACAGC (SEQ ID NO:18) |
| BAA23656 | 2662339 | WDWCCELCCNPACFGC (SEQ ID NO:19) |
| P31518 | 399947 | SDWCCEVCCNPACAGC (SEQ ID NO:8) |

The immature (including pre and pro regions) form of *E. coli* ST-1A (ST-P) protein has the sequence: mkklmlaifisvls-fpsfsqstesldsskekitletkkcdv-vknhsekksenmnntfyccelccnpacagcy (SEQ ID NO:20); see GenBank® Accession No. P01559 (gi: 123711). The pre sequence extends from aa 1-19. The pro sequence extends from aa 20-54. The mature protein extends from 55-72. The immature (including pre and pro regions) form of *E. coli* ST-1B (ST-H) protein has the sequence: mkksilfiflsvlsfsp-faqdakpvesskekitleskkc-niakksnksgpesmnssnyccelccnpactgcy (SEQ ID NO: 21); see GenBank® Accession No. P07965 (gi: 3915589). The immature (including pre and pro regions) form of *Y. enterocolitica* ST protein has the sequence: mkkivfvlvlmlssgafgqetvsgqfs-dalstpitaevykqacdpplppaevssdwdccdvccnpacagc (SEQ ID NO:22) see GenBank® Accession No. S25659 (gi: 282047).

The peptides of the invention, like the bacterial ST peptides, have six Cys residues. These six Cys residues form three disulfide bonds in the mature and active form of the peptide. If the six Cys residues are identified, from the amino to carboxy terminus of the peptide, as A, B, C, D, E, and F, then the disulfide bonds form as follows: A-D, B-E, and C-F. The formation of these bonds is thought to be important for GC-C receptor binding. Certain of the peptides of the invention include a potentially functional chymotrypsin cleavage site, e.g., a Trp, Tyr or Phe located between either Cys B and Cys D or between Cys E and Cys F. Cleavage at either chymotrypsin cleavage site reduces or eliminates the ability of the peptide to bind to the GC-C receptor.

In the human body an inactive form of chymotrypsin, chymnotrypsinogen is produced in the pancreas. When this inactive enzyme reaches the small intestine it is converted to active chymotrypsin by the excision of two di-peptides. Active chymotrypsin can potentially cleave peptides at the peptide bond on the carboxy-terminal side of Trp, Tyr or Phe. The presence of active chymotrypsin in the intestinal tract can potentially lead to cleavage of certain of the peptides of the invention having an appropriately positioned functional chymotrypsin cleavage site. It is expected that chymotrypsin cleavage will moderate the action of a peptide of the invention having an appropriately positioned chymotrypsin cleavage site as the peptide passes through the intestinal tract.

Trypsinogen, like chymotrypsin, is a serine protease that is produced in the pancreas and is present in the digestive tract. The active form, trypsin, will cleave peptides having a Lys or Arg. The presence of active trypsin in the intestinal tract can lead to cleavage of certain of the peptides of the invention having an appropriately positioned functional trypsin cleavage site. It is expected that chymotrypsin cleavage will moderate the action of a peptide of the invention having an appropriately positioned trypsin cleavage site as the peptide passes through the intestinal tract.

Many gastrointestinal disorders, including IBS, are associated with abdominal or visceral pain. Certain of the peptides of the invention include analgesic or antinociceptive tags such as the carboxy-terminal sequence AspPhe immediately following a Trp, Tyr or Phe that creates a functional chymotrypsin cleavage site or following Lys or Arg that creates a functional trypsin cleavage site. Chymotrypsin in the intestinal tract can potentially cleave such peptides immediately carboxy terminal to the Trp, Phe or Tyr residue, releasing the dipeptide, AspPhe. This dipeptide has been shown to have analgesic activity in animal models (Abdikkahi, et al. 2001, Fundam Clin Pharmacol 15:117-23; Nikfar et al 1997, 29:583-6; Edmundson et al 1998; Clin Pharmacol Ther 63:580-93). In this manner such peptide's can treat both pain and inflammation. Other analgesic peptides can be present at the carboxy terminus of the peptide (following a functional cleavage site) including: endomorphin-1, endomorphin-2, nocistatin, dalargin, lupron, and substance P. A number of the useful peptides are based on the core sequence: Cys Cys Glu <u>Leu</u> Cys Cys Asn Pro Ala Cys <u>Thr</u> Gly Cys Tyr (SEQ ID NO:29). To create a variant having a potentially functional chymotrypsin cleavage site capable of inactivating the peptide, either the Leu (underlined) or the Thr (underlined) can be replaced by Trp, Phe or Tyr or both the Leu and the Thr can be replaced by (independently) Trp, Phe or Tyr. To create a variant having an analgesic di-peptide, the core sequence is followed by Asp Phe. The carboxy terminal Tyr in the core sequence can allow the Asp Phe dipeptide to be released by chymotrypsin in the digestive tract. The core sequence can be optionally be preceded by Asn Ser Ser Asn Tyr or Asn.

Thus, useful variants based on the core sequence include:

```
                                          (SEQ ID NO:26)
Asn Ser Ser Asn Tyr Cys Cys Glu Leu Cys Cys Asn

Pro Ala Cys Thr Gly Cys Tyr;
                                          (SEQ ID NO:27)
Asn Ser Ser Asn Tyr Cys Cys Glu Leu Cys Cys Asn

Pro Ala Cys Trp Gly Cys Tyr
                                          (SEQ ID NO:28)
Asn Ser Ser Asn Tyr Cys Cys Glu Tyr Cys Cys Asn

Pro Ala Cys Thr Gly Cys Tyr;
                                          (SEQ ID NO:29)
Cys Cys Glu Leu Cys Cys Asn Pro Ala Cys Thr Gly

Cys Tyr;
                                          (SEQ ID NO:30)
Cys Cys Glu Leu Cys Cys Asn Pro Ala Cys Trp Gly

Cys Tyr
                                          (SEQ ID NO:31)
Cys Cys Glu Tyr Cys Cys Asn Pro Ala Cys Thr Gly

Cys Tyr;
                                          (SEQ ID NO:32)
Asn Cys Cys Glu Leu Cys Cys Asn Pro Ala Cys Thr

Gly Cys Tyr
                                          (SEQ ID NO:33)
Asn Cys Cys Glu Leu Cys Cys Asn Pro Ala Cys Trp

Gly Cys Tyr
                                          (SEQ ID NO:34)
Asn Cys Cys Glu Phe Cys Cys Asn Pro Ala Cys Thr

Gly Cys Tyr
                                          (SEQ ID NO:35)
Asn Cys Cys Glu Tyr Cys Cys Asn Pro Ala Cys Thr

Gly Cys Tyr
                                          (SEQ ID NO:36)
Asn Cys Cys Glu Trp Cys Cys Asn Pro Ala Cys Thr

Gly Cys Tyr
                                          (SEQ ID NO:37)
Asn Cys Cys Glu Arg Cys Cys Asn Pro Ala Cys Thr

Gly Cys Tyr
                                          (SEQ ID NO:38)
Asn Cys Cys Glu Lys Cys Cys Asn Pro Ala Cys Thr

Gly Cys Tyr
                                          (SEQ ID NO:39)
Asn Ser Ser Asn Tyr Cys Cys Glu Leu Cys Cys Asn

Pro Ala Cys Thr Gly Cys Tyr Asp Phe
                                          (SEQ ID NO:40)
Asn Ser Set Asn Tyr Cys Cys Glu Leu Cys Cys Asn

Pro Ala Cys Trp Gly Cys Tyr Asp Phe
                                          (SEQ ID NO:41)
Asn Ser Ser Asn Tyr Cys Cys Glu Phe Cys Cys Asn

Pro Ala Cys Thr Gly Cys Tyr Asp Phe
                                          (SEQ ID NO:42)
Asn Ser Ser Asn Tyr Cys Cys Glu Tyr Cys Cys Asn

Pro Ala Cys Thr Gly Cys Tyr Asp Phe
                                          (SEQ ID NO:43)
Asn Ser Ser Asn Tyr Cys Cys Glu Trp Cys Cys Asn

Pro Ala Cys Thr Gly Cys Tyr Asp Phe
                                          (SEQ ID NO:44)
Asn Ser Ser Asn Tyr Cys Cys Glu Arg Cys Cys Asn

Pro Ala Cys Thr Gly Cys Tyr Asp Phe
                                          (SEQ ID NO:45)
Asn Ser Ser Asn Tyr Cys Cys Glu Lys Cys Cys Asn

Pro Ala Cys Thr Gly Cys Tyr Asp Phe
                                          (SEQ ID NO:46)
Cys Cys Glu Leu Cys Cys Asn Pro Ala Cys Thr Gly

Cys Tyr Asp Phe
```

-continued (SEQ ID NO:47)
Cys Cys Glu Leu Cys Cys Asn Pro Ala Cys Trp Gly
Cys Tyr Asp Phe (SEQ ID NO:48)
Cys Cys Glu Phe Cys Cys Asn Pro Ala Cys Thr Gly
Cys Tyr Asp Phe (SEQ ID NO:49)
Cys Cys Glu Tyr Cys Cys Asn Pro Ala Cys Thr Gly
Cys Tyr Asp Phe (SEQ ID NO:50)
Cys Cys Glu Trp Cys Cys Asn Pro Ala Cys Thr Gly
Cys Tyr Asp Phe (SEQ ID NO:51)
Cys Cys Glu Arg Cys Cys Asn Pro Ala Cys Thr Gly
Cys Tyr Asp Phe (SEQ ID NO:52)
Cys Cys Glu Lys Cys Cys Asn Pro Ala Cys Thr Gly
Cys Tyr Asp Phe (SEQ ID NO:53)
Asn Cys Cys Glu Leu Cys Cys Asn Pro Ala Cys Thr
Gly Cys Tyr Asp Phe (SEQ ID NO:54)
Asn Cys Cys Glu Leu Cys Cys Asn Pro Ala Cys Trp
Gly Cys Tyr Asp Phe (SEQ ID NO:55)
Asn Cys Cys Glu Phe Cys Cys Asn Pro Ala Cys Thr
Gly Cys Tyr Asp Phe (SEQ ID NO:56)
Asn Cys Cys Glu Tyr Cys Cys Asn Pro Ala Cys Thr
Gly Cys Tyr Asp Phe (SEQ ID NO:57)
Asn Cys Cys Glu Trp Cys Cys Asn Pro Ala Cys Thr
Gly Cys Tyr Asp Phe (SEQ ID NO:58)
Asn Cys Cys Glu Arg Cys Cys Asn Pro Ala Cys Thr
Gly Cys Tyr Asp Phe (SEQ ID NO:59)
Asn Cys Cys Glu Lys Cys Cys Asn Pro Ala Cys Thr
Gly Cys Tyr Asp Phe In some cases, the peptides of the invention are produced as a prepro protein that includes the amino terminal leader sequence: mkksilfiflsvlsfspfqdakpvesskekitleskkcniakksnksgpesmn (SEQ ID NO:23). Where the peptide is produced by a bacterial cell, e.g., E. coli, the forgoing leader sequence will be cleaved and the mature peptide will be efficiently secreted from the bacterial cell. U.S. Pat. No. 5,395,490 describes vectors, expression systems and methods for the efficient production of ST peptides in bacterial cells and methods for achieving efficient secretion of mature ST peptides. The vectors, expression systems and methods described in U.S. Pat. No. 5,395,490 can be used to produce the ST peptides and variant ST peptides of the present invention Variant Peptides The invention includes variant peptides which can include one, two, three, four, five, six, seven, eight, nine, or ten (in some embodiments fewer than 5 or fewer than 3 or 2 or fever) amino acid substitutions compared to SEQ ID NOs:25 to 59 and 66 to 110. The substitution(s) can be conservative or non-conservative. The naturally-occurring amino acids can be substituted by D-isomers of any amino acid, non-natural amino acids, and other groups. A conservative amino acid substitution results in the alteration of an amino acid for a similar acting amino acid, or amino acid of like charge, polarity, or hydrophobicity. At some positions, even conservative amino acid substitutions can reduce the activity of the peptide. Among the naturally occurring amino acid substitutions generally considered conservative are:

| For Amino Acid | Code | Replace with any of |
|---|---|---|
| Alanine | Ala | Gly, Cys, Ser |
| Arginine | Arg | Lys, His |
| Asparagine | Asn | Asp, Glu, Gln, |
| Aspartic Acid | Asp | Asn, Glu, Gln |
| Cysteine | Cys | Met, Thr, Ser |
| Glutamine | Gln | Asn, Glu, Asp |
| Glutamic Acid | Glu | Asp, Asn, Gln |
| Glycine | Gly | Ala |
| Histidine | His | Lys, Arg |
| Isoleucine | Ile | Val, Leu, Met |
| Leucine | Leu | Val, Ile, Met |
| Lysine | Lys | Arg, His |
| Methionine | Met | Ile, Leu, Val |
| Phenylalanine | Phe | Tyr, His, Trp |
| Proline | Pro | |
| Serine | Ser | Thr, Cys, Ala |
| Threonine | Thr | Ser, Met, Val |
| Tryptophan | Trp | Phe, Tyr |
| Tyrosine | Tyr | Phe, His |
| Valine | Val | Leu, Ile, Met |

In some circumstances it can be desirable to treat patients with a variant peptide that binds to and activates intestinal GC-C receptor, but is less active than the non-variant form the peptide. This reduced activity can arise from reduced affinity for the receptor or a reduced ability to activate the receptor once bound or reduced stability of the peptide. In some peptides pairs of Cys residues which normally form a disulfide bond one or both members of the pair can be replaced by homocysteine, 3-mercaptoproline (Kolodziej et al. 1996 Int J Pept Protein Res 48:274); β,β dimethylcysteine (Hunt et al. 1993 Int J Pept Protein Res 42:249) or diaminoprionic acid (Smith et al. 1978 J Med Chem 21:117) to form alternative internal cross-links at the positions of the normal disulfide bonds.

Production of Peptides

Useful peptides can be produced either in bacteria including, without limitation, *E. coli*, or in other existing systems for peptide or protein production (e.g., *Bacillus subtilis*, baculovirus expression systems using *Drosophila* Sf9 cells, yeast or filamentous fungal expression systems, mammalian cell expression systems), or they can be chemically synthesized.

If the peptide or variant peptide is to be produced in bacteria, e.g., *E. coli*, the nucleic acid molecule encoding the peptide will preferably also encode a leader sequence that permits the secretion of the mature peptide from the cell. Thus, the sequence encoding the peptide can include the pre sequence and the pro sequence of, for example, a naturally-occurring bacterial ST peptide. The secreted, mature peptide can be purified from the culture medium.

The sequence encoding a peptide of the invention is preferably inserted into a vector capable of delivering and maintaining the nucleic acid molecule in a bacterial cell. The DNA molecule may be inserted into an autonomously replicating vector (suitable vectors include, for example, pGEM3Z and pcDNA3, and derivatives thereof). The vector nucleic acid may be a bacterial or bacteriophage DNA such as bacteriophage lambda or M13 and derivatives thereof. Construction of a vector containing a nucleic acid described herein can be followed by transformation of a host cell such as a bacterium. Suitable bacterial hosts include but are not limited to, *E. coli, B. subtilis, Pseudomonas, Salmonella*. The genetic construct also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences. A variety of transcriptional control sequences are well known to those in the art. The expression vector can also include a translation regulatory sequence (e.g., an untranslated 5' sequence, an untranslated 3' sequence, or an internal ribosome, entry site). The vector can be capable of autonomous replication or it can integrate into host DNA to ensure stability during peptide production.

The protein coding sequence that includes a peptide of the invention can also be fused to a nucleic acid encoding a polypeptide affinity tag, e.g., glutathione S-transferase (GST), maltose E binding protein, protein A, FLAG tag, hexa-histidine, myc tag or the influenza HA tag, in order to facilitate purification. The affinity tag or reporter fusion joins the reading frame of the peptide of interest to the reading frame of the gene encoding the affinity tag such that a translational fusion is generated. Expression of the fusion gene results in translation of a single polypeptide that includes both the peptide of interest and the affinity tag. In some instances where affinity tags are utilized, DNA sequence encoding a protease recognition site will be fused between the reading frames for the affinity tag and the peptide of interest.

Genetic constructs and methods suitable for production of immature and mature forms of the peptides and variants of the invention in protein expression systems other than bacteria, and well known to those skilled in the art, can also be used to produce peptides in a biological system.

Mature peptides and variants thereof can be synthesized by the solid-phase method using an automated peptide synthesizer. For example, the peptide can be synthesized on Cyc (4-$CH_2$ Bxl)-$OCH_2$-4-(oxymethyl)-phenylacetamidomethyl resin using a double coupling program. Protecting groups must be used appropriately to create the correct disulfide bond pattern. For example the following protecting groups can be used: t-butyloxycarbonyl (alpha-amino groups); acetamidomethyl (thiol groups of Cys residues B and E); 4-methylbenzyl (thiol groups of Cys residues C and F); benzyl (y-carboxyl of glutamic acid and the hydroxyl group of threonine, if present); and bromobenzyl (phenolic group of tyrosine, if present). Coupling is effected with symmetrical anhydride of t-butoxylcarbonylamino acids or hydroxybenzotriazole ester (for asparagine or glutamine residues), and the peptide is, deprotected and cleaved from the solid support in hydrogen fluoride, dimethyl sulfide anisole, and p-thiocresol using 8/1/1/0.5 ratio (v/v/v/w) at 0° C. for 60 min. After removal of hydrogen fluoride and dimethyl sulfide by reduced pressure and anisole and p-thiocresol by extraction with ethyl ether and ethyl acetate sequentially, crude peptides are extracted with a mixture of 0.5M sodium phosphate buffer, pH 8.0 and N,N-dimethylformamide using 1/1 ratio, v/v. The disulfide bond for Cys residues B and E is the formed using dimethyl sulfoxide (Tam et al. (1991), *J. Am. Chem. Soc.* 113:6657-62). The resulting peptide is the purified by reverse-phase chromatography. The disulfide bond between Cys residues C and F is formed by first dissolving the peptide in 50% acetic acid in water. Saturated iodine solution in glacial acetic acid is added (1 ml iodine solution per 100 ml solution). After incubation at room temperature for 2 days in an enclosed glass container, the solution is diluted five-fold with deionized water and extracted with ethyl ether four times for removal of unreacted iodine. After removal of the residual amount of ethyl ether by rotary evaporation the solution of crude product is lyophilized and purified by successive reverse-phase chromatography.

Intestinal GC-C Receptor Binding Assay

The ability of peptides and other agents to bind to the intestinal GC-C receptor can be tested as follows. Cells of the T84 human colon carcinoma cell line (American Type Culture Collection (Bethesda, Md.) are grown to confluence in 24-well culture plates with a 1:1 mixture of Ham's F12 medium and Dulbecco's modified Eagle's medium (DMEM), supplemented with 5% fetal calf serum. Cells used in the assay are typically between passages 54-60. Briefly, T84 cell monolayers in 24-well plates are washed twice with 1 ml of binding buffer (DMEM containing 0.05% bovine serum albumin and 25 mM HEPES, pH 7.2), then incubated for 3.0 min at 37° C. in the presence of mature radioactively labeled *E. coli* ST peptide and the test material at various concentrations. The cells are then washed four times with 1 ml of DMEM and solubilized with 0.5 ml/well 1N NaOH. The level of radioactivity in the solubilized material is then determined using standard methods.

Example 1

Preparation of Variant ST Peptides and Wild-Type ST Peptide

1a: Preparation of Recombinant Variant ST Peptides and Wild-Type ST Peptide

A variant ST peptide, referred to as SEQ ID NO:28, was reproduced recombinantly and tested in an animal model. SEQ ID NO:28, has the sequence: Asn Ser Ser Asn Tyr Cys Cys Glu Tyr Cys Cys Asn Pro Ala Cys Thr Gly Cys Tyr (SEQ ID NO:28). A peptide having the sequence of the wild-type ST peptide was also created SEQ ID NO:26).

SEQ ID NO:28 and SEQ ID NO:26 peptides were produced as preproproteins using vectors produced as follows. A sequence encoding a heat-stable enterotoxin pre-pro sequence was amplified from pGK51/pGSK51 (ATCC 67728) using oligonucleotide MO3514 (5' CACACCATAT-GAAGAAATCAATATTATTTATTTTTCTTTCTG 3' (SEQ ID NO:60)) and oligonucleotide MO3515-(5' CACACCTC-GAGTTAGGTCTCCATGCTTTCAGGAC-CACTTTTATTAC 3' (SEQ ID NO:61)). The amplification product fragment was digested with NdeI/XhoI and ligated to the T7 expression vector, pET-26b(+) (Novagen) digested with NdeI/XhoI thereby creating plasmid MB3976. The region encoding the pre-pro protein was sequenced and found to encode the amino acid sequence: mkksilfiflsvlsfsp-faqdakpagsskekitleskkcnivkksnksgpesm (SEQ ID NO:24) which differs from the amino acid sequence of heat-stable enterotoxin a2 precursor (sta2; mkksilfiflsvlsfsp-faqdakpagsskekitleskkcnivkknnesspesm (SEQ ID NO:25); GenBank® Accession No. Q47185, GI: 3913876) at three positions (indicated by underlining and bold text) near the C-terminus. To create expression vectors with the pre-pro sequence, complementary oligos encoding each ST peptide variant or wild-type ST peptide were annealed and cloned into the MB3976 expression vector. To create MB3984 (encoding SEQ ID NO:26 peptide full length wild-type ST peptide as a prepro protein), containing the amino acid sequence, NSSNYCCELCCNPACTGCY (SEQ ID NO:26) fused downstream of the pre-pro sequence, MB3976 was digested with BsaI/XhoI and ligated to annealed oligos MO3621 (5' GCATGAATAGTAGAATTACTGCTGT-GAATTGTGTTGTAATCCTGCTTGTACCGGGT GCTAT-TAATAAC 3' (SEQ ID NO:62)) and MO3622 (5' TCGAGT-TATTAATAGCACCCGGTACAAGCAGCAGGATTACAA-CACAATTCACAGCAGTA ATTGCTACTATTC 3' (SEQ ID NO:63)). To create MB3985 (encoding SEQ ID NO:28 as a prepro protein) containing the following amino acid sequence, NSSNYCCEYCCNPACTGCY fused downstream of the pre-pro sequence, MB 3976 was digested with BsaI/XhoI and ligated to annealed oligos MO3529 (5' GCAT-GAATAGTAGCAATTACTGCTGTGAATAT-TGTTGTAATCCTGCTTGTACCGGGTGCTATTA ATAAC 3' (SEQ ID NO:64)) and MO3530 (5' TCGAGTTATTAAT-AGCACCCGGTACAAGCAGGATTACAACAATATT CACAGCAGTA ATTGCTACTATTC 3' (SEQ ID NO:65)).

The SEQ ID NO:28 peptide and the SEQ ID NO:26 peptide were produced as follows. The expression vectors were transformed into *E. coli* bacterial host BL21λ DE3 (Invitrogen). A single colony was innoculated and grown shaking overnight at 30° C. in L broth+25 mg/l kanamycin. The overnight culture was added to 3.2 L of batch medium (Glucose 25 g/l, Caseamino Acids 5 g/l, Yeast Extract 5 g/l, $KH_2PO_4$ 13.3 g/l, $(NH_4)_2HPO_4$ 4 g/l, $MgSO_4$-$7H_2O$ 1.2 g/l, Citric Acid 1.7 g/l, EDTA 8.4 mg/l, $CoCl_2$-$6H_2O$ 2.5 mg/l, $MnCl_2$-$4H_2O$ 15 mg/l, $CuCl_2$-$4H_2O$ 1.5 mg/l, $H_3BO_3$ 3 mg/l, $Na_2MoO_4$-$2H_2O$ 2.5 mg/l, Zn Acetate-$2H_2O$ 13 mg/l, Ferric Citrate 100 mg/l, Kanamycin 25 mg/l, Antifoam $DF_2O_4$ 1 ml/l) and fermented using the following process parameters: pH 6.7—control with base only (28% $NH_4OH$), 30° C., aeration: 5 liters per minute. After the initial consumption of batch glucose (based on monitoring dissolved oxygen (DO) levels), 1.5 L of feed medium (Glucose 700 g/l, Caseamino Acids 10 g/l, Yeast Extract 10 g/l, $MgSO_4$-$7H_2O$ 4 g/l, EDTA 13 mg/l, $CoCl_2$-$6H_2O$ 4 mg/l, $MnCl_2$-$4H_2O$ 23.5 mg/l, $CuCl_2$-$4H_2O$ 2.5 mg/l, $H_3BO_3$ 5 mg/l, $Na_2MoO_4$-$2H_2O$ 4 mg/l, Zn Acetate-$2H_2O$ 16 mg/l, Ferric Citrate 40 mg/l, Antifoam $DF_2O_4$ 1 ml/l) was added at a feed rate controlled to maintain 20% DO. IPTG was added to 0.2 mM 2 hours post feed start. The total run time was approximately 40-45 hours (until feed exhaustion).

Cells were collected by centrifugation at 5,000 g for 10 minutes. The cell pellet was discarded and the supernatant was passed through a 50 Kd ultrafiltration unit. The 50 Kd filtrate (0.6 liters) was loaded onto a 110 ml Q-Sepharose fast Flow column (Amersham Pharmacia, equilibrated with 20 mM Tris-HCl pH 7.5) at a flow rate of 400 ml/hour. The column was washed with six volumes of 20 mM Tris-HCl pH 7.5 and proteins were eluted with 50 mM acetic acid collecting 50 ml fractions. Fractions containing ST peptide variant or wild-type ST peptide were pooled and the solvent was removed by rotary evaporation. The dried proteins were resuspended in 10 ml of 8% acetic acid, 0.1% trifluoroacetic acid (TFA) and loaded onto a Varian Polaris C18-A column (250×21.2 mm 10 μm, equilibrated in the same buffer) at a flow rate of 20 ml/min. The column was washed with 100 ml of 8% methanol, 0.1% TFA and developed with a gradient (300 ml) of 24 to 48% methanol, 0.1% TFA, collecting 5-ml fractions. Fractions containing peptide were pooled and the solvent was removed by rotary evaporation. The peptides were dissolved in 0.1% TFA and lyophilized.

The SEQ ID NO:28 peptide and SEQ ID NO:26 peptide fractions were analyzed by standard LCMS and HPLC. LCMS analysis revealed that SEQ ID NO:28 is more homogeneous than SEQ ID NO:26 (see FIG. 1*a*; note that SEQ ID NO:28 peptide exhibits fewer peaks (Panel B) than SEQ ID NO:26 (Panel A)).

1*b*: Preparation of Synthetic Variant ST Peptides and Wild-Type ST Peptide

Peptides were chemically synthesized by a commercial peptide synthesis company. Varying yields of peptides were obtained depending on the efficiency of chemical synthesis. Thus, the four peptides, in decreasing order of yield were: Cys Cys Glu Tyr Cys Cys Asn Pro Ala Cys Thr Gly Cys Tyr (SEQ ID NO:31; 10-20% yield; Cys Cys Glu Leu Cys Cys Asn Pro Ala Cys Thr Gly Cys Tyr (SEQ ID NO:29); Asn Ser Ser Asn Tyr Cys Cys Asn Pro Ala Cys Thr Gly Cys Tyr (SEQ ID NO:28); Asn Ser Ser Asn Tyr Cys Cys Glu Leu Cys Cys Asn Pro Ala Cys Thr Gly Cys Tyr (SEQ ID NO:26), <5% yield. Thus the specific amino acid changes introduced into the peptides can create improved manufacturing properties.

Figure 1C:
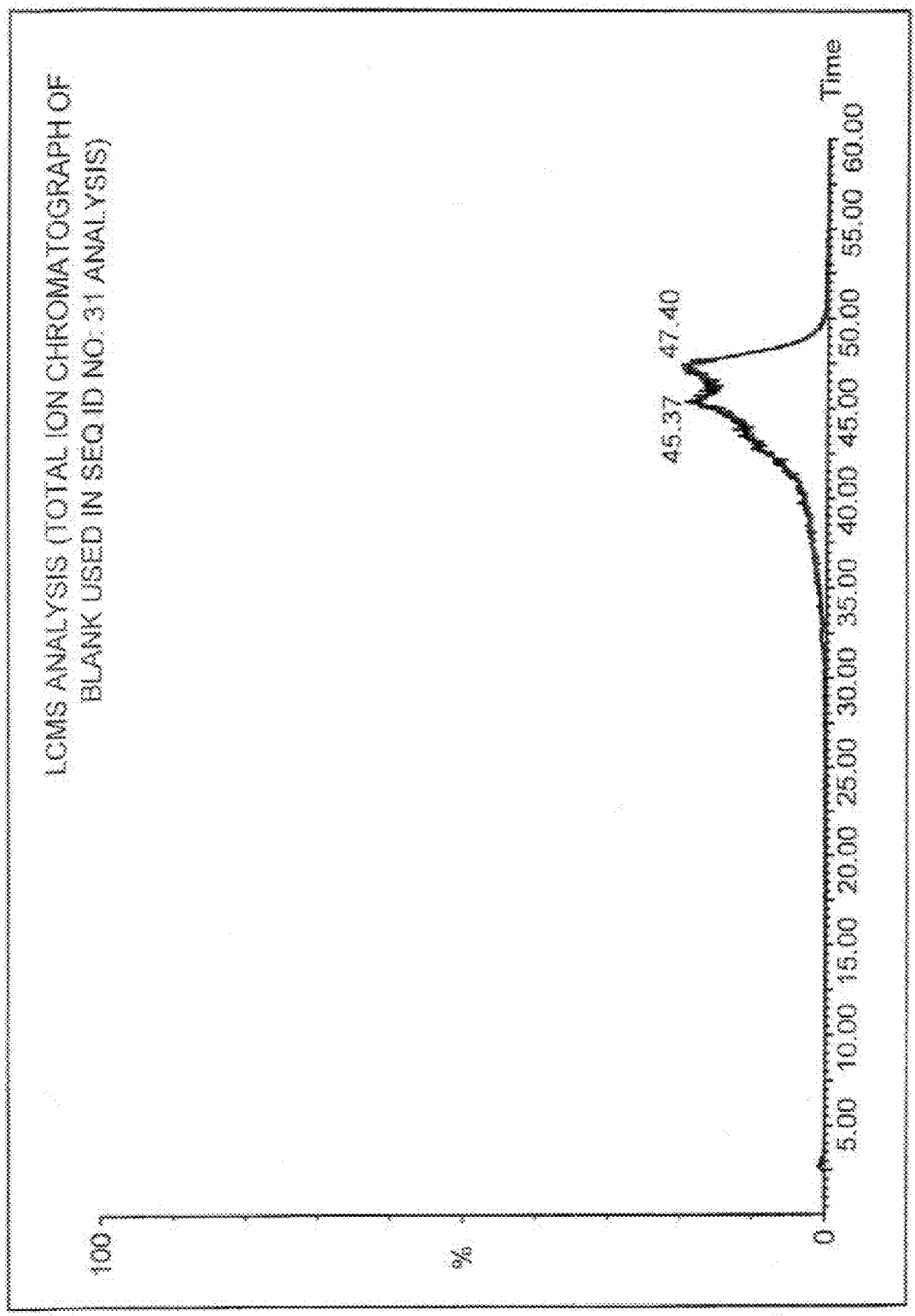

FIG. 1*b* shows the total ion chromatograph profile of synthetically manufactured MD-1100. FIG. 1*c* shows the total ion chromatograph profile of the control blank sample. There is one major peak present in the SEQ ID NO:31 sample that is not also present in the control sample. Quantitative analysis suggests the SEQ ID NO:31 is >98% pure.

Example 2

Activation of the Intestinal GC-C Receptor by a Variant ST Peptide and ST Peptide The ability of SEQ ID NO:28, SEQ ID NO:26, and SEQ ID NO:31 to activate the intestinal GC-C receptor was assessed in an assay employing the T84 human colon carcinoma cell line (American Type Culture Collection (Bethesda, Md.). For the assays cells were grown to confluency in 24-well culture plates with a 1:1 mixture of Ham's F12 medium and Dulbecco's modified Eagle's medium (DMEM), supplemented with 5% fetal calf serum and were used at between passages 54 and 60.

Briefly, monolayers of T84 cells in 24-well plates were washed twice with 1 ml/well DMEM, then incubated at 37° C. for 10 min with 0.45 ml DMEM containing 1 mM isobutyl-methylxanthine (IBMX), a cyclic nucleotide phosphodiesterase inhibitor. Test peptides (50 μl) were then added and incubated for 30 minutes at 37° C. The media was aspirated and the reaction was then terminated by the addition of ice cold 0.5 ml of 0.1N HCl. The samples were held on ice for 20 minutes and then evaporated to dryness using a heat gun or vacuum centrifugation. The dried samples were resuspended in 0.5 ml of phosphate buffer provided in the Cayman Chemical Cyclic GMP EIA kit (Cayman Chemical, Ann Arbor, Mich.). Cyclic GMP was measured by EIA according to procedures outlined in the Cayman Chemical Cyclic GMP EIA kit.

FIG. 2 shows the activity of chemically synthesized peptide variants in this GC-C receptor activity assay. In this assay, SEQ ID NO:26 and two different SEQ ID NO:31 peptides (SEQ ID NO:31(a) and SEQ ID NO:31(b), synthesized by two different methods) had activity comparable to SEQ ID NO:26. SEQ ID NO:28 and SEQ ID NO:26 peptide were chemically synthesized in a manner identical to that of SEQ ID NO:31(b).

Example 3

SEQ ID NO:28 and SEQ ID NO:26 Increase Intestinal Transit in Mice

In order to determine whether the peptides increase the rate of gastrointestinal transit, the peptides and controls were tested using a murine gastrointestinal transit (GIT) assay (Moon et al. *Infection and Immunity* 25:127, 1979). In this assay, charcoal, which can be readily visualized in the gastrointestinal tract is administered to mice after the administration of a test compound. The distance traveled by the charcoal is measured and expressed as a percentage of the total length of the colon.

Mice were fasted with free access to water for 12 to 16 hours before the treatment with peptide or control buffer. The peptides were orally administered at 1 μg/kg-1 mg/kg of peptide in buffer (20 mM, Tris pH 7.5) 7 minutes before being given an oral dose of 5% Activated Carbon (Aldrich 242276-250G). Control mice were administered buffer only before being given a dose of Activated Carbon. After 15 minutes, the mice were sacrificed and their intestines from the stomach to the cecum were dissected. The total length of the intestine as well as the distance traveled from the stomach to the charcoal front was measured for each animal and the results are expressed as the percent of the total length of the intestine traveled by the charcoal front. All results are reported as the average of 10 mice±standard deviation. A comparison of the distance traveled by the charcoal between the mice treated with peptide versus the mice treated with vehicle alone was performed using a Student's t test and a statistically significant difference was considered for P<0.05. P-values are calculated using a two-sided T-Test assuming unequal variances.

As can be seen in FIG. 3a, b, wild-type ST peptide SEQ ID NO:26, (Sigma-Aldrich, St Louis, Mo.; 0.1 mg/kg), synthetically manufactured SEQ ID NO:31 and Zelnorm® (0.1 mg/kg), a drug approved for IBS that is an agonist for the serotonin receptor 5HT4, increase gastrointestinal transit rate in this model. FIG. 4a shows the result of a study demonstrating that intestinal transit rate increases with an increasing dosage of either recombinantly synthesized SEQ ID NO:26 and SEQ ID NO:28. FIG. 4b shows the results of a study demonstrating both chemically synthesized MM-416776 or MD-1100 peptide increase intestinal transit rates more than either Tris buffer alone or an equivalent dose of Zelnorm®.

The identical experiment was performed to determine if SEQ ID NO:31 is effective in a chronic dosing treatment regimen. Briefly, 8 week old CD1 female mice are dosed orally once a day for 50 days with either SEQ ID NO:31 (0.06 mg/kg or 0.25 in/kg in 20 mM Tris pH 7.5) or vehicle alone (20 mM Tris pH 7.5). On the $5^{th}$ day, a GIT assay is performed identical to that above except 200 μl of a 10% charcoal solution is administered. FIG. 4c shows the results of a study demonstrating both chemically synthesized SEQ ID NO:31 or Zelnorm® are effective in a mouse gastrointestinal motility assay upon chronic dosing (daily for 5 days). The results are shown side by side with acute dosing (1 day).

Example 4

SEQ ID NO:28 Peptide and SEQ ID NO:26 Peptide Increase Intestinal Secretion in Suckling Mice (SuMi Assay)

SEQ ID-NO:26 peptide and SEQ ID NO:28 were tested for their ability to increase intestinal secretion using a suckling mouse model of intestinal secretion. In this model a test compound is administered to suckling mice that are between 7 and 9 days old. After the mice are sacrificed, the gastrointestinal tract from the stomach to the cecum is dissected ("guts"). The remains ("carcass") as well as the guts are weighed and the ratio of guts to carcass weight is calculated. If the ratio is above 0.09, one can conclude that the test compound increases intestinal secretion. FIG. 5a shows a dose response curve for wild-type ST peptide (SEQ ID NO:26) in this model. FIG. 5b shows dose response curve for the SEQ ID NO:31 peptide in this model. These data show that wild-type ST peptide (purchased from TDT, Inc. West Chester, Pa.) and the MD-1100 peptide increase intestinal secretion. The effect of Zelnorm® was also studied. As can be seen from FIG. 5, Zelnorm® at 0.2 mg/kg does not increase intestinal secretion this model. FIG. 6a shows a dose response curve for the recombinant MM-416776 peptide described above and the recombinant SEQ ID NO:28 peptide described above. As can be seen from FIG. 6a, both peptides increase intestinal secretion in this model. Similarly FIG. 6b shows a dose response curve for chemically synthesized SEQ ID NO:28, SEQ ID NO:31 and SEQ ID NO:26 as well as wild-type ST peptide (purchased from Sigma-Aldrich, St Louis, Mo.).

Colonic Hyperalgesia Animal Models

Hypersensitivity to colorectal distension is common in patients with IBS and may be responsible for the major symptom of pain. Both inflammatory and non-inflammatory animal models of visceral hyperalgesia to distension have been developed to investigate the effect of compounds on visceral pain in IBS.

I. Trinitrobenzenesulphonic Acid (TNBS)-Induced Rectal Allodynia Model

Male Wistar rats (220-250 g) were premedicated with 0.5 mg/kg of acepromazine injected intraperitoneally (IP) and anesthetized by intramuscular administration of 100 mg/kg of ketamine. Pairs of nichrome wire electrodes (60 cm in length and 80 μm in diameter) were implanted in the striated muscle of the abdomen, 2 cm laterally from the white line. The free ends of electrodes were exteriorized on the back of the neck and protected by a plastic tube attached to the skin. Electromyographic (EMG) recordings were started 5 days after surgery. Electrical activity of abdominal striated muscle was recorded with an electroencephalograph machine (Mini VIII, Alvar, Paris, France), using a short time constant (0.03 sec.) to remove low-frequency signals (<3 Hz).

Ten days post surgical implantation, trinitrobenzenesulphonic acid (TNBS) was administered to induce rectal inflammation. TNBS (80 mg kg$^{-1}$ in 0.3 ml 50% ethanol) was administered intrarectally through a silicone rubber catheter introduced at 3 cm from the anus under light diethyl-ether anesthesia as described (Morteau, et al. 1994 Dig Dis Sci 39:1239). Following TNBS administration, rats were placed in plastic tunnels where they were severely limited in mobility for several days before colorectal distension (CRD). Experimental compound was administered one hour before CRD which was performed by insertion into the rectum, at 1 cm of the anus, a 4 cm long balloon made from a latex condom (Gue et al. 1997 *Neurogastroenterol. Motil.* 9:271). The balloon was fixed on a rigid catheter taken from an embolectomy probe (Fogarty). The catheter attached balloon was fixed at the base of the tail. The balloon, connected to a barostat, was inflated progressively by step of 15 mmHg, from 0 to 60 mmHg, each step of inflation lasting 5 min. Evaluation of rectal sensitivity, as measured by EMG, was performed before (1-2 days) and 3 days following rectal instillation of TNBS.

The number of spike bursts that corresponds to abdominal contractions was determined per 5 min periods. Statistical analysis of the number of abdominal contractions and evaluation of the dose-effects relationships was performed by a one way analysis of variance (ANOVA) followed by a post-hoc (Student or Dunnett tests) and regression analysis for ED50 if appropriate.

FIG. 7 shows the results of experiment in which SEQ ID NO:31 activity was analyzed in the TNBS colorectal model. Significant decreases in abdominal response are observed at 0.3 μg/kg and 3 μg/kg SEQ ID NO:31. These results demonstrate that SEQ ID NO:31 reduces pain associated with colorectal distension in this animal model.

II. Stress-Induced Hyperalgesia Model

Male Wistar Rats (200-250 g) are surgically implanted with nichrome wire electrodes as in the TNBS model. Ten days post surgical implantation, partial restraint stress (PRS), is performed as described by Williams et al. for two hours (Williams et al. 1988 Gastroenterology 64:611). Briefly, under light anesthesia with ethyl-ether, the foreshoulders, upper forelimbs and thoracic trunk are wrapped in a confining harness of paper tape to restrict, but not prevent body movements. Control sham-stress animals are anaesthetized but not wrapped. Thirty minutes before the end of the PRS session, the animals are administered test-compound or vehicle. Thirty minutes to one hour after PRS completion, the CRD distension procedure is performed as described above for the TNBS model with barostat at pressures of 15, 30, 45 and 60 mm Hg. Statistical analysis on the number of bursts is determined and analyzed as in the TNBS model above.

Phenylbenzoquinone-Induced Writhing Model

The PBQ-induced writhing model can be used to assess pain control activity of the peptides and GC-C receptor agonists of the invention. This model is described by Siegmund et al. (1957 Proc. Soc. Exp. Bio. Med. 95:729-731). Briefly, one hour after oral dosing with a test compound, e.g., a peptide, morphine or vehicle, 0.02% phenylbenzoquinone (PBQ) solution (12.5 mL/kg) is injected by intraperitoneal route into the mouse. The number of stretches and writhings are recorded from the 5$^{th}$ to the 10$^{th}$ minute after PBQ injection, and can also be counted between the 35$^{th}$ and 40$^{th}$ minute and between the 60$^{th}$ and 65$^{th}$ minute to provide a kinetic assessment. The results are expressed as the number of stretches and writhings (mean±SEM) and the percentage of variation of the nociceptive threshold calculated from the mean value of the vehicle treated group. The statistical significance of any differences between the treated groups and the control group is determined by a Dunnett's test using the residual variance after a one-way analysis of variance (P<0.05) using SigmaStat Software.

FIGS. 8a and 8b show the effect of different doses of SEQ ID NO:28 and SEQ ID NO:31 in the PBQ writhing assay. Indomethacin, an NSAID (nonsteroidal anti-inflammatory drug) with known pain control activity, was used as the positive control in the assay. Significant reductions in writhings were observed for SEQ ID NO:28 (1 mg/kg dose) and SEQ ID NO:31 (2.5 mg/kg dose) compared to the vehicle control. Loss of efficacy at the highest dose tested has also been observed for multiple other compounds (such as 5HT-3 antagonists) tested in similar assays. The results of this study suggest that both MD 915 and SEQ ID NO:28 and SEQ ID NO:31 have antinociceptive effects in this visceral pain model comparable to the intermediate doses of indomethacin.

Example 5

SEQ ID NO:31 Kd Determination

To determine the affinity of SEQ ID NO:31 for GC-C receptors found in rat intestinal mucosa, a competition binding assay was performed using rate intestinal epithelial cells. Epithelial cells from the small intestine of rats were obtained as described by Kessler et al. (*J. Biol. Chem.* 245: 5281-5288 (1970)). Briefly, animals were sacrificed and their abdominal cavities exposed. The small intestine was rinsed with 300 ml ice cold saline or PBS. 10 cm of the small intestine measured at 10 cm from the pylorus was removed and cut into 1 inch segments. Intestinal mucosa was extruded from the intestine by gentle pressure between a piece of parafilm and a P-1000 pipette tip. Intestinal epithelial cells were placed in 2 ml PBS and pipetted up and down with a 5 ml pipette to make a suspension of cells. Protein concentration in the suspension was measured using the Bradford method (*Anal. Biochem.* 72: 248-254 (1976)).

A competition binding assay was performed based on the method of Giannella et al. (*Am. J. Physiol.* 245: G492-G498) between [$^{125}$I] labeled SEQ ID NO:26 and SEQ ID NO:31. The assay mixture contained: 0.5 ml of DME with 20 mM HEPES-KOH pH 7.0, 0.9 mg of the cell suspension listed above, 21.4 fmol [$^{125}$I]-SEQ ID NO:26 (42.8 pM), and different concentrations of competitor SEQ ID NO:31 (0.01 to 1000 nM). The mixture was incubated at room temperature for 1 hour, and the reaction stopped by applying the mixture to GF/B glass-fiber filters (Whatman). The filters were washed with 5 ml ice-cold PBS and radioactivity was measured. FIG. 9 shows that the Kd for SEQ ID NO:31 in this assay is 4.5 nm. % B/Bo is the percentage of the ratio of radioactivity trapped in each sample (B) compared to the radioactivity retained in a control sample with no cold competitor (Bo). Giannella et al. (*Am. J. Physiol.* 245: G492-G498) observed that the Kd for wild-type ST peptide in this same assay was ~13 nm.

Example 6

Pharmacokinetic Properties of SEQ ID NO:31

To study the pharmacokinetics of SEQ ID NO:31, absorbability studies in mice were performed by administering SEQ ID NO:31 intravaneously via fail vein injection or orally by gavage to 8-week-old CD1 mice. Serum was collected from the animals at various time points and tested for the presence of SEQ ID NO:31 using a competitive enzyme-linked immunoabsorbent assay (Oxoid, ST EIA kit, Cat#TD0700). The assay utilized monoclonal antibodies against ST peptide (antibodies are provided in the Oxoid kit) and synthetically manufactured SEQ ID NO:31. FIG. 10a show absorption data for intravenously and orally administered SEQ ID NO:31 as detected by the ELISA assay. MD-1100 appears to be minimally systemically absorbed and is <2.2% bioavailable.

A similar bioavailability study was performed in which LCMS rather than ELISA was used to detect SEQ ID NO:31. Initially, serum samples were extracted from the whole blood of exposed and control mice, then injected directly (10 mL) onto an in-line solid phase extraction (SPE) column (Waters Oasis HLB 25 mm column, 2.0×15 mm direct connect) without further processing. The sample on the SPE column was washed with a 5% methanol, 95% $dH_2O$ solution (2.1 mL/min, 1.0 minute), then loaded onto an analytical column using a valve switch that places the SPE column in an inverted flow path onto the analytical column (Waters Xterra MS C8 5 mm IS column, 2.1×20 mm). The sample was eluted from the analytical column with a reverse phase gradient (Mobile Phase A: 10 mM ammonium hydroxide in $dH_2O$, Mobile Phase B: 10 mM ammonium hydroxide in 80% acetonitrile and 20% methanol; 20% B for the first 3 minutes then ramping to 95% B over 4 min. and holding for 2 min., all at a flow rate of 0.4 mL/min.). At 9.1 minutes, the gradient returns to the initial conditions of 20% B for 1 min. SEQ ID NO:31 eluted from the analytical column at 1.45 minutes, and was detected by triple-quadrapole mass spectrometry (MRM, 764 (+2 charge state)>182 (+1 charge state) Da; cone voltage=30V; collision=20 eV; parent resolution=2 Da at base peak; daughter resolution=2 Da at base peak). Instrument response was converted into concentration units by comparison with a standard curve using known amounts of chemically synthesized SEQ ID NO:31 prepared and injected in mouse serum using the same procedure.

FIG. 10b shows absorption data for IV and orally administered SEQ ID NO:31 as detected by LCMS. In this assay, SEQ ID NO:31 appears similarly minimally systemically absorbed and is <0.11% bioavailable.

Administration of Peptides and GC-C Receptor Agonists

For treatment of gastrointestinal disorders, the peptides and agonists of the invention are preferably administered orally, e.g., as a tablet, gel, paste, slurry, liquid, powder or in some other form. Orally administered compositions can include binders, flavoring agents, and humectants. The peptides and agonists can be co-administered with other agents used to treat gastrointestinal disorders including but not limited to acid suppressing agents such as Histamine-2 receptor agonists (H2As), and proton pump inhibitors (PPIs). The peptides and agonists can also be administered by rectal suppository. For the treatment of disorders outside the gastrointestinal tract such as congestive heart failure and benign prostatic hypertrophy, peptides and agonists are preferably administered parenterally or orally. The peptides described herein can be used alone or in combination with other agents. For example, the peptides can be administered together with an analgesic peptide or compound. The analgesic peptide or compound can be covalently attached to a peptide described herein or it can be a separate agent that is administered together with or sequentially with a peptide described herein in a combination, therapy.

Combination therapy can be achieved by administering two or more agents, e.g., a peptide described herein and an analgesic peptide or compound, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

The agents, alone or in combination can be combined with any pharmaceutically acceptable carrier or medium. Thus, they can be combined with materials that do not produce an adverse, allergic or otherwise unwanted redaction when administered to a patient. The carriers or mediums used can include solvents, dispersants, coatings, absorption promoting agents, controlled release agents, etc.

The agents either in their free form or as a salt can be combined with a polymer such as polylactic-glycoloic acid (PLGA), poly-(I)-lactic-glycolic-tartaric acid (P(I)LGT) (WO 01/12233), polyglycolic acid (U.S. Pat. No. 3,773,919), polylactic acid (U.S. Pat. No. 4,767,628); poly(ϵ-caprolactone) to create a sustained release formulation. Such formulations can be used to implants that release a peptide or another agent over a period of a few days, a few weeks or several months depending on the polymer, the particle size of the polymer, and the size of the implant (see, e.g., U.S. Pat. No. 6,620,422). Other sustained release formulations are described in EP 0 467 389 A2, WO 93/241150, U.S. Pat. No. 5,612,052; WO 97/40085, WO 94/155587, U.S. Pat. No. 5,672,659, U.S. Pat. No. 5,893,985, U.S. Pat. No. 5,134,122, U.S. Pat. No. 5,192,741, U.S. Pat. No. 5,192,741, and U.S. Pat. No. 5,445,832. In such sustained release formulations microparticles of peptide are combined with microparticles of polymer. One or more sustained release implants can be placed in the large intestine, the small intestine or both.

The agents can be administered, e.g., by intravenous injection, intramuscular injection, subcutaneous injection, or by other routes. The agents can be administered orally e.g., as a tablet, gel, paste, slurry, liquid, powder or in some other form. Orally administered compositions can include binders, flavoring agents, and humectants. The agents can be included in dentifrices or oral washes. Thus, oral formulations can include abrasives and foaming agents. The agents can also be administered transdermally or in the form a suppository.

The agents can be a free acid or base or a pharmacologically acceptable salt thereof. Solids can be dissolved or dispersed immediately prior to administration or earlier. In some circumstances, the preparations include a preservative to prevent the growth of microorganisms. The pharmaceutical forms suitable for injection can include sterile aqueous or organic solutions or dispersions which include, e.g., water, an alcohol, an organic solvent, an oil or other solvent or dispersant (e.g., glycerol, propylene glycol, polyethylene glycol, and vegetable oils). Pharmaceutical agents can be sterilized by filter sterilization or by other suitable means.

Suitable pharmaceutical compositions in accordance with the invention will generally include an amount of the active compound(s) with an acceptable pharmaceutical diluent or excipient, such as a sterile aqueous solution, to give a range of final concentrations, depending on the intended use. The techniques of preparation are generally well known in the art, as exemplified by Remington's Pharmaceutical Sciences (18th Edition, Mack Publishing Company, 1995).

The agents described herein and combination therapy agents can be packaged as a kit that includes single or multiple doses of two or more agents, each packaged or formulated individually, or single or multiple doses of two or more agents packaged or formulated in combination. Thus, one or more agents can be present in first container, and the kit can optionally include one or more agents a second container. The container or containers are placed within a package, and the package can optionally include administration or dosage instructions. A kit can include additional components such as syringes or other means for administering the agents as well as diluents or other means for formulation.

Analgesic Agents

The peptides described herein can be used in combination therapy with an analgesic agent, e.g., an analgesic compound or an analgesic peptide. The analgesic agent can optionally be covalently attached to a peptide described herein. Among the useful analgesic agents are: Ca channel blockers, 5HT receptor antagonists (for example 5HT3, 5HT4 and 5HT1 receptor antagonists), opioid receptor agonists (loperamide, fedotozine, and fentanyl), NK1 receptor antagonists, CCK receptor agonists (e.g., loxiglumide), NK1 receptor antagonists, NK3 receptor antagonists, norepinephrine-serotonin reuptake inhibitors (NSRI), vanilloid and cannabanoid receptor agonists, and sialorphin. Analgesics agents in the various classes are described in the literature.

Among the useful analgesic peptides are sialorphin-related peptides, including those comprising the amino acid sequence QHNPR (SEQ ID NO:111), including: VQHNPR (SEQ ID NO:112); VRQHNPR (SEQ ID NO:113); VRGQHNPR (SEQ ID NO:114), VRGPQHNPR (SEQ ID NO:115); VRGPRQHNPR (SEQ ID NO:116); VRGPRRQHNPR (SEQ ID NO:117); and RQHNPR (SEQ ID NO:118). Sialorphin-related peptides bind to neprilysin and inhibit neprilysin-mediated breakdown of substance P and Met-enkephalin. Thus, compounds or peptides that are inhibitors of neprilysin are useful analgesic agents which can be administered with the peptides of the invention in a co-therapy or linked to the peptides of the invention, e.g., by a covalent bond. Sialophin and related peptides are described in U.S. Pat. No. 6,589,750; U.S. 20030078209 A1; and WO 02/051435 A2.

Opioid receptor antagonists and agonists can be administered with the peptides of the invention in co-therapy or linked to the peptide of the invention, e.g., by a covalent bond. For example, opioid receptor antagonists such as naloxone, naltrexone, methyl nalozone, nalmefene, cypridime, beta funaltrexamine, naloxonazine, naltrindole, and nor-binaltorphimine are thought to be useful in the treatment of IBS. It can be useful to formulate opioid antagonists of this type is a delayed and sustained release formulation such that initial release of the antagonist is in the mid to distal small intestine and/or ascending colon. Such antagonists are described in WO 01/32180 A2. Enkephalin pentapeptide (HOE825; Tyr-D-Lys-Gly-Phe-L-homoserine) is an agonist of the mu and delta opioid receptors and is thought to be useful for increasing intestinal motility (Eur. J. Pharm. 219:445, 1992), and this peptide can be used in conjunction with the peptides of the invention. Also useful is trimebutine which is thought to bind to mu/delta/kappa opioid receptors and activate release of motilin and modulate the release of gastrin, vasoactive intestinal peptide, gastrin and glucagons. Kappa opioid receptor agonists such as fedotozine, ketocyclazocine, and compounds described in WO 03/097051 A2 can be used with or linked to the peptides of the invention. In addition, mu opioid receptor agonists such as morphine, diphenyloxylate, frakefamide (H-Tyr-D-Ala-Phe(F)-Phe-NH$_2$; WO 01/19849A1) and loperamide can be used.

Tyr-Arg (kyotorphin) is a dipeptide that acts by stimulating the release of met-enkephalins to elicit an analgesic effect (J. Biol. Chem 262:81-65, 1987). Kyotorphin can be used with or linked to the peptides of the invention.

CCK receptor agonists such as caerulein from amphibians and other species are useful analgesic agents that can be used with or linked to the peptides of the invention.

Conotoxin peptides represent a large class of analgesic peptides that act at voltage gated Ca channels, NMDA receptors or nicotinic receptors. These peptides can be used with or linked to the peptides of the invention.

Peptide analogs of thymulin (FR Application 2830451) can have analgesic activity and can be used with or linked to the peptides of the invention.

CCK (CCKa or CCKb) receptor antagonists, including loxiglumide and dexloxiglumide (the R-isomer of loxiglumide) (WO 88/05774) can have analgesic activity and can be used with or linked to the peptides of the invention.

Other useful analgesic agents include 5-HT4 agonists such as tegaserod/zelnorm and lirexapride. Such agonists are described in: EP1321142 A1, WO 03/053432A1, EP 505322 A1, EP 505322 B1, U.S. Pat. No. 5,510,353, EP 507672 A1, EP 507672 B1, and U.S. Pat. No. 5,273,983.

Calcium channel blockers such as ziconotide and related compounds described in, for example, EP625162 B1, U.S. Pat. No. 5,364,842, U.S. Pat. No. 5,587,454, U.S. Pat. No. 5,824,645, U.S. Pat. No. 5,859,186, U.S. Pat. No. 5,994,305, U.S. Pat. No. 6,087,091, U.S. Pat. No. 6,136,786, WO 93/13128A1, EP 1336409A1, EP 835126A1, EP 835126 B1, U.S. Pat. No. 5,795,864, U.S. Pat. No. 5,891,849, U.S. Pat. No. 6,054,429, WO 97/01351 A1, can be used with or linked to the peptides of the invention.

Various antagonists of the NK-1, NK-2, and NK-3 receptors (for a review see Giardina et al. 2003 Drugs 6:758) can be can be used with or linked to the peptides of the invention.

NK1 receptor antagonists such as: aprepitant (Merck & Co Inc), vofopitant, ezlopitant (Pfizer, Inc.), R-673 (Hoffmann-La Roche, Ltd), SR-14633 and related compounds described in, for example, EP 873753 A1, US 20010006972 A1, US 20030109417A1, WO 01/52844 A1, can be used with or linked to the peptides of the invention.

NK-2 receptor antagonists such as nepadutant (Menarini Ricerche SpA), saredutant (Sanofi-Synthelabo), SR-144190 (Sanofi-Synthelabo) and UK-290795 (Pfizer Inc) can be used with or linked to the peptides of the invention.

NK3 receptor antagonists such as osanetant (Sanofi-Synthelabo), talnetant and related compounds described in, for example, WO 02/094187 A2, EP 876347 A1, WO 97/21680 A1, U.S. Pat. No. 6,277,862, WO 98/11090, WO 95/28418, WO 97/19927, and Boden et al. (J Med Chem. 39:1664-75, 1996) can be used with or linked to the peptides of the invention.

Norepinephrine-serotonin reuptake inhibitors such as milnacipran and related compounds described in WO 03/077897 A1 can be used with or linked to the peptides of the invention.

Vanilloid receptor antagonists such as arvanil and related compounds described in WO 01/64212 A1 can be used with or linked to the peptides of the invention.

Where the analgesic is a peptide and is covalently linked to a peptide described herein the resulting peptide may also include at least one trypsin or chymotrypsin cleavage site. When present within the peptide, the analgesic peptide may be preceded by (if it is at the carboxy terminus) or followed by (if it is at the amino terminus) a chymotrypsin or trypsin cleavage site that allows release of the analgesic peptide.

In addition to sialorphin-related peptides, analgesic peptides include: AspPhe, endomorphin-1, endomorphin-2, nocistatin, dalargin, lupron, zicnotide, and substance P.

Methods of Treatment

The peptides of the invention can be used for the treatment or prevention of cancer, pre-cancerous growths, or metastatic growths. For example, they can be used for the prevention or treatment of: colorectal/local metastasized colorectal cancer, gastrointestinal tract cancer, lung cancer, cancer or pre-cancerous growths or metastatic growths of epithelial cells, polyps, breast, colorectal, lung, ovarian, pancreatic, prostatic, renal, stomach, bladder, liver, esophageal and testicular carcinoma, carcinoma (e.g., basal cell, basosquamous, Brown-Pearce, ductal carcinoma, Ehrlich tumor, Krebs, Merkel cell, small or non-small cell lung, oat cell, papillary, bronchiolar, squamous cell, transitional cell, Walker), leukemia (e.g., B-cell, T-cell, HTLV, acute or chronic lymphocytic, mast cell, myeloid), histiocytonia, histiocytosis, Hodgkin's disease, non-Hodgkin's lymphoma, plasmacytoma, reticuloendotheliosis, adenoma, adeno-carcinoma, adenofibroma, adenolymphoma, ameloblastoma, angiokeratoma, angiolymphoid hyperplasia with eosinophilia, sclerosing angioma, angiomatosis, apudoma, branchionia, malignant carcinoid syndrome, carcinoid heart disease, carcinosarcoma, cementoma, cholangioma, cholesteatoma, chondrosarcoma, chondroblastoma, chondrosarcoma, chordoma, choristoma, craniopharyngioma, chrondrorna, cylindroma, cystadenocarcinoma, cystadenoma, cystosarconia phyllodes, dysgenninoma, ependymoma, Ewing sarcoma, fibroma, fibrosarcoma, giant cell tumor, ganglioneuroma, glioblastoma, glomangioma, granulosa cell tumor, gynandroblastoma, hamartoma, hemangioendothelioma, hemangioma, hemangio-pericytoma, hemangiosarcoma, hepatoma, islet cell tumor, Kaposi sarcoma, leiomyoma, leiomyosarcoma, leukosarcoma, Leydig cell tumor, lipoma, liposarcoma, lymphaugioma, lymphangiomyoma, lymphangiosarcoma, medulloblastoma, meningioma, mesenchymoma, mesonephroma, mesothelioma, myoblastoma, myoma, myosarcoma, myxoma, myxosarcoma, neurilemmoma, neuroma, neuroblastoma, neuroepithelioma, neurofibroma, neurofibromatosis, odontoma, osteoma, osteosarcoma, papilloma, paraganglioma, paraganglionia, nonchroinaffin, pinealoma, rhabdomyoma, rhabdomyosarcoma, Sertoli cell tumor, teratoma, theca cell tumor, and other diseases in which cells have become dysplastic, immortalized, or transformed.

The peptides of the invention can be used for the treatment or prevention of: Familial Adenomatous Polyposis (FAP) (autosomal dominant syndrome) that precedes colon cancer, hereditary nonpolyposis colorectal cancer (HNPCC), and inherited autosomal dominant syndrome.

For treatment or prevention of cancer, pre-cancerous growths and metastatic growths, the peptides can be used in combination therapy with radiation or chemotherapeutic agents, an inhibitor of a cGMP-dependent phosphodiesterase or a selective cyclooxygenase-2 inhibitor (a number of selective cyclooxygenase-2 inhibitors are described in WO02062369, hereby incorporated by reference).

The peptides can be for treatment or prevention of inflammation. Thus, they can be used alone or in combination with inhibitor of cGMP-dependent phosphodiesterase or a selective cyclooxygenase-2 inhibitor for treatment of organ inflammation, IBD (e.g., Crohn's disease, ulcerative colitis), asthma, nephritis, hepatitis, pancreatitis, bronchitis, cystic fibrosis, ischemic bowel diseases, intestinal inflammations/allergies, coeliac disease, proctitis, eosnophilic gastroenteritis, mastocytosis, and other inflammatory disorders.

The peptides can also be used to treat or prevent insulin-related disorders, for example: II diabetes mellitus, hyperglycemia, obesity, disorders associated with disturbances in glucose or electrolyte transport and insulin secretion in cells, or endocrine disorders. They can be also used in insulin resistance treatment and post-surgical and non-post surgery decrease in insulin responsiveness.

The peptides can be used to prevent or treat respiratory disorders, including, inhalation, ventilation and mucus secretion disorders, pulmonary hypertension, chronic obstruction of vessels and airways, and irreversible obstructions of vessels and bronchi.

The peptides can be used in combination therapy with a phosphodiesterase inhibitor (examples of such inhibitors can be found in U.S. Pat. No. 6,333,354, hereby incorporated by reference).

The peptides can also be used to prevent or treat: retinopathy, nephropathy, diabetic angiopathy, and edema formation The peptides can also be, used to prevent or treat neurological disorders, for example, headache, anxiety, movement disorders, aggression, psychosis, seizures, panic attacks, hysteria, sleep disorders, depression, schizoaffective disorders, sleep apnea, attention deficit syndromes, memory loss, and narcolepsy. They may also be used as a sedative.

The peptides and detectabley labeled peptides can be used as markers to identify, detect, stage, or diagnosis diseases and conditions of the small intestine, including: Crohn's disease, colitis, inflammatory bowel disease, tumors, benign tumors, such as benign stromal tumors, adenoma, angioma, adenomatous (pedunculated and sessile) polyps, malignant, carcinoid tumors, endocrine cell-tumors, lymphoma, adenocarcinoma, foregut, midgut, and hindgut carcinoma, gastroinstestinal stromal tumor (GIST), such as leiomyoma, cellular leiomyoma, leiomyoblastoma, and leiomyosarcoma, gastrointestinal autonomic nerve tumor, malabsorption syndromes, celiac diseases, diverticulosis, Meckel's diverticulum, colonic diverticula, megacolon, Hirschsprung's disease, irritable bowel syndrome, mesenteric ischemia, ischemic colitis, colorectal cancer, colonic polyposis, polyp syndrome, intestinal adenocarcinoma, Liddle syndrome, Brody myopathy, infantile convulsions, and chorcoathetosis The peptides can be conjugated to another molecule (e.g, a diagnostic or therapeutic molecule) to target cells bearing the GCC receptor, e.g., cystic fibrosis lesions and specific cells lining the intestinal tract. Thus, they can be used to target radioactive moieties or therapeutic moieties to the intestine to aid in imaging and diagnosing or treating colorectal/metastasized or local colorectal cancer and to deliver normal copies of the p53 tumor suppressor gene to the intestinal tract.

The peptides can be used alone or in combination therapy to treat erectile dysfunction.

The peptides can be used alone or in combination therapy to treat inner ear disorders, e.g., to treat Meniere's disease, including symptoms of the disease such as vertigo, hearing loss, tinnitus, sensation of fullness in the ear, and to maintain fluid homeostasis in the inner ear.

The peptides can be used alone or in combination therapy to treat disorders associated with fluid and sodium retention, e.g., diseases of the electrolyte-water/electrolyte transport system within the kidney, gut and urogenital system, congestive heart failure, hypertension, hypotension liver cirrhosis, and nephrotic syndrome. In addition they can be used to facilitate diuresis or control intestinal fluid.

The peptides can be used alone or in combination therapy to treat disorders associated with bicarbonate secretion, e.g., Cystic Fibrosis.

The peptides can be used alone or in combination therapy to treat disorders associated with liver cell regeneration.

What is claimed is:

1. A polypeptide comprising the amino acid sequence Cys Cys Glu Xaa Cys Cys Asn Pro Ala Cys Thr Gly Cys Tyr wherein Xaa is selected from Phe, Trp or Tyr (SEQ ID NO: 125) or a pharmaceutically acceptable salt thereof.

2. The polypeptide of claim 1 consisting of the amino acid sequence Cys Cys Glu Xaa Cys Cys Asn Pro Ala Cys Thr Gly Cys Tyr wherein Xaa is selected from Phe, Trp or Tyr (SEQ ID NO:125).

3. The polypeptide according to claim 1, which is purified.

4. The polypeptide according to claim 2, which is purified.

5. The polypeptide of claim 1 comprising the amino acid sequence Cys Cys Glu Phe Cys Cys Asn Pro Ala Cys Thr Gly Cys Tyr (SEQ ID NO: 105) or a pharmaceutically acceptable salt thereof.

6. The polypeptide of claim 5 consisting of the amino acid sequence Cys Cys Glu Phe Cys Cys Asn Pro Ala Cys Thr Gly Cys Tyr (SEQ ID NO:105).

7. The polypeptide of claim 5 or a pharmaceutically acceptable salt thereof, wherein the polypeptide activates the guanylate cyclase C receptor.

8. A pharmaceutical composition comprising the polypeptide of claim 5 or a pharmaceutically acceptable salt thereof and a pharmaceutically acceptable carrier or excipient.

9. The polypeptide of claim 1 comprising the amino acid sequence Cys Cys Glu Trp Cys Cys Asn Pro Ala Cys Thr Gly Cys Tyr (SEQ ID NO: 109) or a pharmaceutically acceptable salt thereof.

10. The polypeptide of claim 9 consisting of the amino acid sequence Cys Cys Glu Trp Cys Cys Asn Pro Ala Cys Thr Gly Cys Tyr (SEQ ID NO: 109).

11. The polypeptide of claim 9 or a pharmaceutically acceptable salt thereof, wherein the polypeptide activates the guanylate cyclase C receptor.

12. A pharmaceutical composition comprising the polypeptide of claim 9 or a pharmaceutically acceptable salt thereof and a pharmaceutically acceptable carrier or excipient.

13. A pharmaceutical composition comprising the polypeptide of claim 1 or a pharmaceutically acceptable salt thereof and a pharmaceutically acceptable carrier or excipient.

14. A pharmaceutical composition comprising the polypeptide of claim 2 and a pharmaceutically acceptable carrier or excipient.

15. A pharmaceutical composition comprising the polypeptide of claim 6 and a pharmaceutically acceptable carrier or excipient.

16. A pharmaceutical composition comprising the polypeptide of claim 10 and a pharmaceutically acceptable carrier or excipient.

* * * * *

(12) INTER PARTES REEXAMINATION CERTIFICATE (851st)
United States Patent
Currie et al.

(10) Number: US 7,704,947 C1
(45) Certificate Issued: *Apr. 3, 2014

(54) METHODS AND COMPOSITIONS FOR THE TREATMENT OF GASTROINTESTINAL DISORDERS

(75) Inventors: Mark G. Currie, Sterling, MA (US); Shalina Mahajan-Miklos, Stanford, CA (US); Thea Norman, San Diego, CA (US); G. Todd Milne, Brookline, MA (US)

(73) Assignee: Ironwood Pharmaceuticals, Inc., Cambridge, MA (US)

Reexamination Request:
No. 95/001,990, May 15, 2012

Reexamination Certificate for:
Patent No.: 7,704,947
Issued: Apr. 27, 2010
Appl. No.: 11/930,696
Filed: Oct. 31, 2007

(*) Notice: This patent is subject to a terminal disclaimer.

Related U.S. Application Data

(62) Division of application No. 10/766,735, filed on Jan. 28, 2004, now abandoned.

(60) Provisional application No. 60/443,098, filed on Jan. 28, 2003, provisional application No. 60/471,288, filed on May 15, 2003, provisional application No. 60/519,460, filed on Nov. 12, 2003.

(51) Int. Cl.
*C07K 14/245* (2006.01)
*C07K 7/08* (2006.01)

(52) U.S. Cl.
USPC .................. 514/4.8; 514/21.5; 530/327

(58) Field of Classification Search
None
See application file for complete search history.

(56) References Cited

To view the complete listing of prior art documents cited during the proceeding for Reexamination Control Number 95/001,990, please refer to the USPTO's public Patent Application Information Retrieval (PAIR) system under the Display References tab.

*Primary Examiner* — Johnny F Railey

(57) ABSTRACT

The present invention features compositions and related methods for treating IBS and other gastrointestinal disorders and conditions (e.g., gastrointestinal motility disorders, functional gastrointestinal disorders, gastroesophageal reflux disease (GERD), Crohn's disease, ulcerative colitis, Inflammatory bowel disease, functional heartburn, dyspepsia (including functional dyspepsia or nonulcer dyspepsia), gastroparesis, chronic intestinal pseudo-obstruction (or colonic pseudo-obstruction), and disorders and conditions associated with constipation, e.g., constipation associated with use of opiate pain killers, post-surgical constipation, and constipation associated with neuropathic disorders as well as other conditions and disorders using peptides and other agents that activate the guanylate cyclase C (GC-C) receptor.

INTER PARTES REEXAMINATION CERTIFICATE ISSUED UNDER 35 U.S.C. 316

NO AMENDMENTS HAVE BEEN MADE TO THE PATENT

AS A RESULT OF REEXAMINATION, IT HAS BEEN DETERMINED THAT:

The patentability of claims 1-16 is confirmed.

\* \* \* \* \*